(12) United States Patent
Styczynski et al.

(10) Patent No.: US 11,624,702 B2
(45) Date of Patent: Apr. 11, 2023

(54) SYSTEMS AND METHODS FOR QUANTIFYING ANALYTES WITH MINIMAL INTER-SAMPLE VARIABILITY

(71) Applicant: Georgia Tech Research Corporation, Atlanta, GA (US)

(72) Inventors: Mark Styczynski, Atlanta, GA (US); Monica P. McNerney, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 149 days.

(21) Appl. No.: 17/273,728

(22) PCT Filed: Sep. 5, 2019

(86) PCT No.: PCT/US2019/049640
§ 371 (c)(1),
(2) Date: Mar. 4, 2021

(87) PCT Pub. No.: WO2020/051268
PCT Pub. Date: Mar. 12, 2020

(65) Prior Publication Data
US 2021/0349012 A1   Nov. 11, 2021

Related U.S. Application Data

(60) Provisional application No. 62/727,022, filed on Sep. 5, 2018.

(51) Int. Cl.
G01N 21/27  (2006.01)
G01N 21/78  (2006.01)
(Continued)

(52) U.S. Cl.
CPC ........... *G01N 21/272* (2013.01); *G01N 21/78* (2013.01); *G01N 33/52* (2013.01); *G01N 33/58* (2013.01)

(58) Field of Classification Search
CPC ...... G01N 21/272; G01N 21/78; G01N 33/52; G01N 33/58; C12Q 1/68; C12Q 1/6897
See application file for complete search history.

(56) References Cited

U.S. PATENT DOCUMENTS

2012/0214154 A1  8/2012  Franciskovich et al.
2012/0244637 A1  9/2012  Karlsson et al.
(Continued)

FOREIGN PATENT DOCUMENTS

WO   2014027964   2/2014
WO   2015/134820  9/2015
(Continued)

OTHER PUBLICATIONS

Search Report and Written Opinion from Application No. PCT/US2019/049640 dated Nov. 20, 2019 (48 pages).
(Continued)

*Primary Examiner* — Jennifer Wecker
*Assistant Examiner* — Oyeleye Alexander Alabi
(74) *Attorney, Agent, or Firm* — Troutman Pepper Hamilton Sanders LLP; Ryan A. Schneider; Chris N. Davis

(57) ABSTRACT

Disclosed herein are systems and methods for quantifying analytes in a desired complex solution with minimal inter-sample variability. The invention includes methods and diagnostic tools for quantifying analytes in aqueous solutions or biological fluid samples with sample-specific calibration and colorimetric or detectable output.

25 Claims, 30 Drawing Sheets

(51) Int. Cl.
*G01N 33/52* (2006.01)
*G01N 33/58* (2006.01)

(56) References Cited

U.S. PATENT DOCUMENTS

| | | |
|---|---|---|
| 2013/0171626 A1 | 7/2013 | Adler et al. |
| 2016/0258938 A1 | 9/2016 | Arenas et al. |
| 2017/0175111 A1 | 6/2017 | Green et al. |
| 2018/0214154 A1 | 8/2018 | Bakos et al. |

FOREIGN PATENT DOCUMENTS

| | | |
|---|---|---|
| WO | 2016/205308 | 12/2016 |
| WO | WO-2016205308 A1 * | 12/2016 |

OTHER PUBLICATIONS

Watstein, et al. "Development of a Pigment-Based Whole-Cell Zinc Biosensor for Human Serum," ACS Synthetic Biology, vol. 7, No. 1 pp. 267-275.

* cited by examiner

SYSTEMS AND METHODS FOR QUANTIFYING ANALYTES WITH MINIMAL INTER-SAMPLE VARIABILITY

CROSS-REFERENCE TO RELATED APPLICATIONS

This application claims priority to U.S. Provisional Application No. 62/727,022, filed on 5 Sep. 2018, the disclosure of which is herein incorporated by reference in its entirety.

GOVERNMENT SPONSORSHIP

This invention was made with government support under Grant Nos. MCB-1254382 and DGE-1650044 awarded by the National Science Foundation; and Grant Nos. R01-EB022592 and R35-GM119701 awarded by the National Institutes of Health. The government has certain rights in the invention.

BACKGROUND OF THE INVENTION

1. Field of the Invention

Embodiments of the present invention relate generally to systems and methods for quantifying analytes in a desired complex solution with minimal inter-sample variability, and more specifically to methods and diagnostic tools for quantifying analytes in aqueous solutions or biological fluid samples with sample-specific calibration and colorimetric or detectable output.

2. Background

Most diagnostics, particularly those adapted for blood analytics, are complex assays that require highly-trained staff and sophisticated analytical equipment, resulting in high per-sample costs and long waiting times for results. Simple, low-cost diagnostics from small blood sample volumes are needed to avoid these issues. Cell-free expression systems, comprising cell extracts supplemented with additional chemical resources, can be a particularly promising approach to fulfill this potential. In particular, their low cost, ease of use, small reaction volumes, and ability to be stably stored and shipped in a lyophilized, freeze-dried format make cell-free expression systems appealing for use in almost any setting (from field studies to at-home use), with minimal or no equipment required. To date, however, equipment-free cell-free expression-based diagnostics have been limited only to presence/absence detection (not quantification), and only to diseases with nucleic acid biomarkers. Importantly, the overwhelming majority of clinically relevant biomarkers for conditions beyond infectious disease are not nucleic acids, and for these biomarkers, quantification of their concentrations is important.

Quantitative measurement of biomarkers and other analytes in complex samples is inherently difficult to do robustly, and even more so when constrained to a minimal-equipment framework. Variability in the components of complex samples like biological fluids or water can affect the readouts of even sophisticated analytical instrumentation, a phenomenon known as "matrix effects" that can yield inaccurate results. In a system with minimal equipment and no mechanisms to compensate for sample-to-sample variability, these matrix effects may be substantial and could preclude the use of standard quantification approaches like calibration curves made from chemical standards, thus hindering development of quantitative diagnostics.

What is needed, therefore, is a quantitative diagnostic system and method that reduces or eliminates inter-sample variability in measuring analytes with complex samples such as biological fluids and water. The diagnostic system and method should enable sample-specific calibration to reduce or eliminate such variability and provide a generalizable parallel calibration strategy. It is to such a system and method that embodiments of the present invention are directed.

BRIEF SUMMARY OF THE INVENTION

As specified in the Background Section, there is a great need in the art to identify technologies for quantitative diagnostic systems and tools for use in complex solutions and use this understanding to develop novel quantitative diagnostic systems and methods for reducing or eliminating inter-sample variability in measuring analytes with complex samples such as biological fluids and water by providing a generalizable parallel calibration strategy. The present invention satisfies this and other needs.

In one aspect, the disclosure is directed to a method of generating a diagnostic tool for measuring an unknown amount of an analyte in a biological sample using a cell-free extract (CFE), the diagnostic tool comprising a plurality of reference points, each reference point being a distinct color and corresponding to a different amount of the analyte, the method comprising: determining a desired amount of a regulator of a reporter; determining a saturating amount of the analyte; and determining a desired reaction time, wherein the desired amount of the regulator of the reporter, the saturating amount of the analyte, and the desired reaction time are determined such that when the unknown amount of the analyte in the biological sample is combined with the CFE and the desired amount of the regulator of the reporter for the desired reaction time, a colorimetric gene product is generated having a color corresponding to a color of a first reference point in the plurality of reference points containing the biological sample, the CFE, the saturating amount of analyte, and the desired amount of the regulator of the reporter, the first reference point associated with a known amount of the analyte about equal to the unknown amount of analyte. The method can be configured to reduce or eliminate inter-sample variability.

In another aspect, the disclosure is directed to a method for generating a range of visible colors in serum samples with unknown amounts of an analyte by addition of a small molecule, wherein the small molecule displaces an interfering molecule from one or more of a regulator, a reporter, and a molecule acted on by the reporter, the method comprising: determining a desired amount of a regulator of a reporter; determining a saturating amount of the analyte; and determining a desired reaction time, wherein the desired amount of the regulator of the reporter, the saturating amount of the analyte, and the desired reaction time are determined such that when the unknown amount of the analyte is combined with the serum, and the desired amount of the regulator of the reporter for the desired reaction time, a colorimetric gene product is generated having a color corresponding to a color of a first reference point in the plurality of reference points containing the serum, the saturating amount of analyte, and the desired amount of the regulator of the reporter, the first reference point associated with a known amount of the analyte about equal to the unknown amount of analyte. The method can be configured to reduce or eliminate inter-sample variability.

In another aspect, the disclosure is directed to a method of measuring an unknown amount of an analyte in a biological sample using a cell-free extract (CFE), the method comprising: providing a diagnostic tool, the tool comprising a plurality of reference points, each reference point in the plurality of reference points being a distinct color and corresponding to a predetermined different amount of the analyte; combining the biological sample, the CFE, a predetermined saturating amount of the analyte, and a predetermined amount of a regulator of a reporter; reacting the regulator of the reporter with the analyte for a predetermined reaction time to generate a colorimetric gene product; determining a first reference point in the plurality of reference points having a color corresponding to the generated colorimetric gene product, wherein the predetermined different amount of the analyte corresponding to the first reference point is equal to the unknown amount of the analyte in the biological sample added to the CFE. The method can be configured to reduce or eliminate inter-sample variability.

In another aspect, the disclosure is directed to a method of generating a diagnostic tool for measuring an unknown amount of an analyte in an aqueous solution, the diagnostic tool comprising a plurality of reference points, each reference point being a distinct color and corresponding to a different amount of the analyte, the method comprising: determining a desired amount of a regulator of a reporter; determining a saturating amount of the analyte; and determining a desired reaction time, wherein the desired amount of the regulator of the reporter, the saturating amount of the analyte, and the desired reaction time are determined such that when the unknown amount of the analyte is combined with the aqueous solution, and the desired amount of the regulator of the reporter for the desired reaction time, a colorimetric gene product is generated having a color corresponding to a color of a first reference point in the plurality of reference points containing the aqueous solution, the saturating amount of analyte, and the desired amount of the regulator of the reporter, the first reference point associated with an amount of the analyte about equal to the unknown amount of analyte, and wherein the method is configured to reduce or eliminate inter-sample variability.

In another aspect, the disclosure provides a method for generating a range of visible colors in aqueous samples with unknown amounts of an analyte by addition of a small molecule, wherein the small molecule displaces an interfering molecule from one or more of a regulator, a reporter, and a molecule acted on by the reporter, the method comprising: determining a desired amount of a regulator of a reporter; determining a saturating amount of the analyte; and determining a desired reaction time, wherein the desired amount of the regulator of the reporter, the saturating amount of the analyte, and the desired reaction time are determined such that when the unknown amount of the analyte is combined with the aqueous solution, and the desired amount of the regulator of the reporter for the desired reaction time, a colorimetric gene product is generated having a color corresponding to a color of a first reference point in the plurality of reference points containing the aqueous solution, the saturating amount of analyte, and the desired amount of the regulator of the reporter, the first reference point associated with an amount of the analyte about equal to the unknown amount of analyte, and wherein the method is configured to reduce or eliminate inter-sample variability.

In another aspect, the disclosure provides a method of measuring an unknown amount of an analyte in an aqueous solution, the method comprising: providing a diagnostic tool, the tool comprising a plurality of reference points, each reference point in the plurality of reference points being a distinct color and corresponding to a predetermined different amount of the analyte; combining the aqueous solution, a predetermined saturating amount of the analyte, and a predetermined amount of a regulator of a reporter; reacting the regulator of the reporter with the analyte for a predetermined reaction time to generate a colorimetric gene product; determining a first reference point in the plurality of reference points having a color corresponding to the generated colorimetric gene product, wherein the predetermined different amount of the analyte corresponding to the first reference point is equal to the unknown amount of the analyte in the aqueous solution, and wherein the method is configured to reduce or eliminate inter-sample variability.

In one aspect, the disclosure provides a diagnostic tool for measuring an unknown amount of an analyte in a biological sample with a cell-free extract (CFE), the tool comprising: a first reference point having a first distinct color corresponding to a first amount of the analyte; a second reference point having a second distinct color corresponding to a second amount of the analyte; and a third reference point having a third distinct color corresponding to a third amount of the analyte, wherein the first distinct color is substantially similar to a colorimetric gene product generated when the biological sample with the first amount of the analyte is combined with the CFE, a predetermined amount of a regulator of a reporter and a predetermined saturation amount of the analyte for a predetermined reaction time, wherein the second distinct color is substantially similar to a colorimetric gene product generated when the biological sample with the second amount of the analyte is combined with the CFE, the predetermined amount of the regulator of a reporter and the predetermined saturation amount of the analyte for the predetermined reaction time, wherein the third distinct color is substantially similar to a colorimetric gene product generated when the biological sample with the third amount of the analyte is combined with the CFE, the predetermined amount of the regulator of a reporter and the predetermined saturation amount of the analyte for the predetermined reaction time. The diagnostic tool can be configured to reduce or eliminate inter-sample variability.

In another aspect, the disclosure provides a diagnostic tool for measuring an unknown amount of an analyte in an aqueous solution, the tool comprising: a first reference point having a first distinct color corresponding to a first amount of the analyte; a second reference point having a second distinct color corresponding to a second amount of the analyte; and a third reference point having a third distinct color corresponding to a third amount of the analyte, wherein the first distinct color is substantially similar to a colorimetric gene product generated when an aqueous solution with the first amount of the analyte is combined with a predetermined amount of a regulator of a reporter and a predetermined saturation amount of the analyte for a predetermined reaction time, wherein the second distinct color is substantially similar to a colorimetric gene product generated when an aqueous solution with the second amount of the analyte is combined with the predetermined amount of the regulator of a reporter and the predetermined saturation amount of the analyte for the predetermined reaction time, wherein the third distinct color is substantially similar to a colorimetric gene product generated when an aqueous solution with the third amount of the analyte is combined with the predetermined amount of the regulator of a reporter and the predetermined saturation amount of the analyte for the predetermined reaction time. The diagnostic tool can be configured to reduce or eliminate inter-sample variability.

These and other objects, features and advantages of the present invention will become more apparent upon reading the following specification in conjunction with the accompanying description, claims and drawings.

BRIEF DESCRIPTION OF THE DRAWINGS

The accompanying Figures, which are incorporated in and constitute a part of this specification, illustrate several aspects described below.

FIG. 21A-20B show simulated trigger RNA and switch plasmid mapping. (21A) The switch concentrations for standard reactions necessary to in silico recapitulate the in silico simulated circuit responses to seven trigger concentrations were calculated. For all standard reactions, the trigger RNA inputs were set to a saturating level and only the transcription rate of switch (β) was estimated to match simulated test reactions. The estimated values of β were then mapped back to plasmid concentrations. (21B) The inventors' model is able to qualitatively recapitulate the trend of trigger RNA concentrations in test reactions and switch plasmid in standard reactions. However, possibly due to the limitations of the model's assumptions, there may be systematic bias in the absolute quantitative values of simulated switch plasmid concentrations (FIG. 19).

DETAILED DESCRIPTION OF THE INVENTION

Figure 1A:
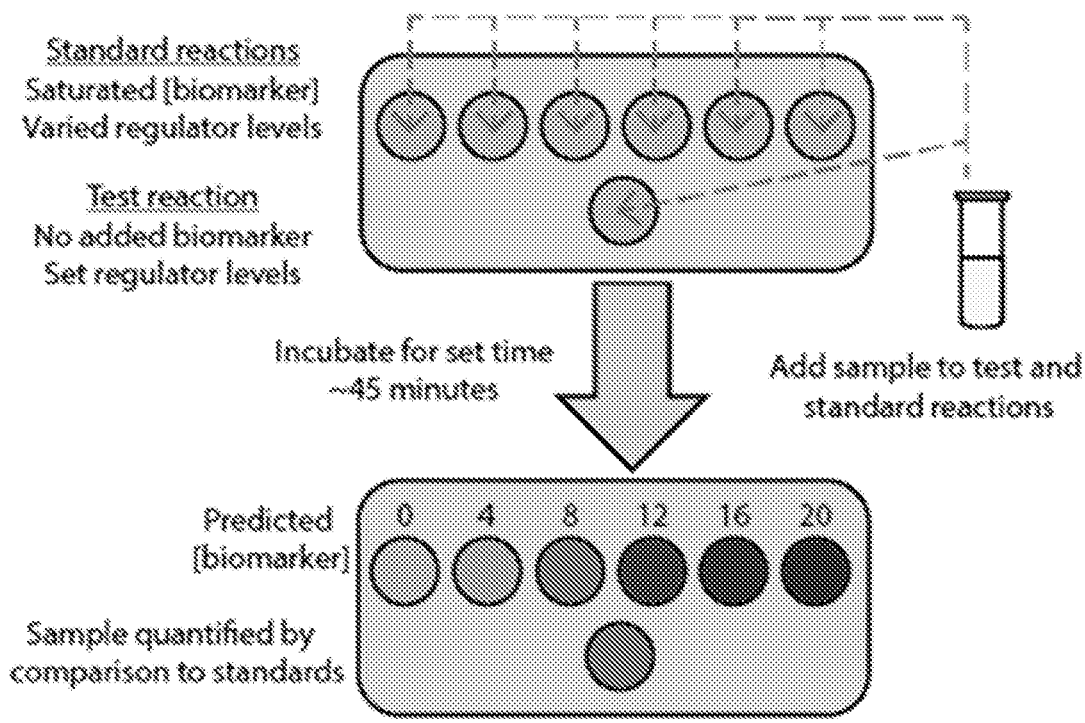
FIG. 1A-1F depicts the proposal and development of parallel calibration approach for matrix-specific biomarker quantification. (1A) Schematic of standardization method to account for matrix effects. An array of standard reactions had saturated biomarker concentrations and varied regulator concentrations. The test reaction had a set regulator concentration and no added biomarker. The sample to be analyzed was added to both the standard and test reactions so that all reactions run in the same sample matrix. After a set incubation time, the color of the test reaction can be matched to the color of the standard reactions to determine biomarker concentration in the test reaction. (1B) Schematic of an exemplary zinc-responsive circuit used to control β-galactosidase production. On one plasmid, ZntR is expressed from a T7 promoter, and on a second plasmid, β-galactosidase is expressed from the ZntR-activated promoter PzntA. (1C) Pictures of visible colors from reactions corresponding with different absorbance measurements. The lowest A580 readings correspond with yellow reactions (the color of CPRG), and as the A580 increases, and the reaction color turns different shades of orange, red, and purple (the color of CPR). (1D) Quantitative colorimetric response to added zinc. At early time points, there was no detectable absorbance of the purple substrate CPR at tested [$Zn^{2+}$], and reactions appeared yellow (the color of CPRG). As the reactions proceeded, they produced CPR at different rates based on the concentration of $Zn^{2+}$ in the reaction, with the maximal differences visible between 60 and 70 minutes. An ideal assay readout time would yield outputs spanning a wide range of absorbances across as much of the [$Zn^{2+}$] range as possible. (1E) Fluorescent response to zinc in 25% human serum, demonstrating substantial matrix effects in serum. (1F) Selected time-course readings of test and standard reactions run in 25% serum, demonstrating the mapping between the two reaction designs.

As specified in the Background Section, there is a great need in the art to identify technologies for quantitative diagnostic systems and tools for use in complex solutions and use this understanding to develop novel quantitative diagnostic systems and methods for reducing or eliminating inter-sample variability in measuring analytes with complex samples such as biological fluids and water by providing a generalizable parallel calibration strategy.

To facilitate an understanding of the principles and features of the various embodiments of the invention, various illustrative embodiments are explained below. Although exemplary embodiments of the invention are explained in detail, it is to be understood that other embodiments are contemplated. Accordingly, it is not intended that the invention is limited in its scope to the details of construction and arrangement of components set forth in the following description or examples. The invention is capable of other embodiments and of being practiced or carried out in various ways. Also, in describing the exemplary embodiments, specific terminology will be resorted to for the sake of clarity.

It must also be noted that, as used in the specification and the appended claims, the singular forms "a," "an" and "the" include plural references unless the context clearly dictates otherwise. For example, reference to a component is intended also to include composition of a plurality of components. References to a composition containing "a" constituent is intended to include other constituents in addition to the one named. In other words, the terms "a," "an," and "the" do not denote a limitation of quantity, but rather denote the presence of "at least one" of the referenced item.

As used herein, the term "and/or" may mean "and," it may mean "or," it may mean "exclusive-or," it may mean "one," it may mean "some, but not all," it may mean "neither," and/or it may mean "both." The term "or" is intended to mean an inclusive "or."

Also, in describing the exemplary embodiments, terminology will be resorted to for the sake of clarity. It is intended that each term contemplates its broadest meaning as understood by those skilled in the art and includes all technical equivalents which operate in a similar manner to accomplish a similar purpose. It is to be understood that embodiments of the disclosed technology may be practiced without these specific details. In other instances, well-known methods, structures, and techniques have not been shown in detail in order not to obscure an understanding of this description. References to "one embodiment," "an embodiment," "example embodiment," "some embodiments," "certain embodiments," "various embodiments," etc., indicate that the embodiment(s) of the disclosed technology so described may include a particular feature, structure, or characteristic, but not every embodiment necessarily includes the particular feature, structure, or characteristic. Further, repeated use of the phrase "in one embodiment" does not necessarily refer to the same embodiment, although it may.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range. Ranges may be expressed herein as from "about" or "approximately" or "substantially" one particular value and/or to "about" or "approximately" or "substantially" another particular value. When such a range is expressed, other exemplary embodiments include from the one particular value and/or to the other particular value.

The term "about" means within an acceptable error range for the particular value as determined by one of ordinary skill in the art, which will depend in part on how the value is measured or determined, i.e., the limitations of the measurement system. For example, "about" can mean within an acceptable standard deviation, per the practice in the art. Alternatively, "about" can mean a range of up to ±20%, preferably up to ±10%, more preferably up to ±5%, and more preferably still up to ±1% of a given value. Alternatively, particularly with respect to biological systems or processes, the term can mean within an order of magnitude, preferably within 2-fold, of a value. Where particular values are described in the application and claims, unless otherwise stated, the term "about" is implicit and in this context means within an acceptable error range for the particular value.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

Throughout this description, various components may be identified having specific values or parameters, however, these items are provided as exemplary embodiments. Indeed, the exemplary embodiments do not limit the various aspects and concepts of the present invention as many comparable parameters, sizes, ranges, and/or values may be implemented. The terms "first," "second," and the like, "primary," "secondary," and the like, do not denote any order, quantity, or importance, but rather are used to distinguish one element from another.

It is noted that terms like "specifically," "preferably," "typically," "generally," and "often" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention. It is also noted that terms like "substantially" and "about" are utilized herein to represent the inherent degree of uncertainty that may be attributed to any quantitative comparison, value, measurement, or other representation.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "50 mm" is intended to mean "about 50 mm."

It is also to be understood that the mention of one or more method steps does not preclude the presence of additional method steps or intervening method steps between those steps expressly identified. Similarly, it is also to be understood that the mention of one or more components in a composition does not preclude the presence of additional components than those expressly identified.

The materials described hereinafter as making up the various elements of the present invention are intended to be illustrative and not restrictive. Many suitable materials that would perform the same or a similar function as the materials described herein are intended to be embraced within the scope of the invention. Such other materials not described herein can include, but are not limited to, materials that are developed after the time of the development of the invention, for example. Any dimensions listed in the various drawings are for illustrative purposes only and are not intended to be limiting. Other dimensions and proportions are contemplated and intended to be included within the scope of the invention.

Definitions

The term "expression" as used herein is defined as the transcription and/or translation of a particular nucleotide sequence driven by its promoter. The amount of expression may be measured by using any method known to those of skill in the art to be suitable. For example, mRNA expression of the protein of interest may be detected using northern blots or their polypeptide products may be identified using immunoassays. Alternatively, transcription based assays using reporter genes may be used as described in U.S. Pat. No. 5,436,128, herein incorporated by reference.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide. In cell-free systems, PCR products may be used in a similar manner as expression vectors and may contain the same expression control systems and cis-acting expression elements.

The term "reporter" as used herein includes a reporter gene that is attached to a genetic element that is regulated, directly or indirectly, by a regulator. The reporter gene is operatively connected to the genetic element such that the expression of the reporter gene serves as an indication of the regulator's activity.

Non-limiting examples of the genetic element include a promoter (e.g., an inducible promoter), a binding site for a repressor, a binding site for an activator, a binding site for a regulatory molecule, a binding site for a transcription factor, a binding site for a ribosome, and translation regulatory elements (such as for example and without limitation, hairpin RNA sequences and small regulatory RNAs such as siRNA and microRNA). The genetic element can also include enhancer sequences that modulate the activity of the promoter, or control sequences that modulate the activity or efficiency of the RNA polymerase that recognizes the promoter, or control sequences that are recognized by effector molecules. The genetic element can also include sequences that modulate the activity or efficacy of the ribosome, or control sequences that are recognized by effector molecules, or control sequences that modulate protein levels post-translationally (such as, for example, tags that induce degradation by proteases).

The reporter gene produces a measurable or quantifiable gene product, such as a colorimetric gene product. As used herein, a colorimetric gene product includes, e.g., a fluorescent gene product, a luminescent gene product, a colored gene product that is visible to the naked eye, and a gene product that is optically detectable at a certain wavelength. The colorimetric gene product may be directly produced by the reporter gene (e.g., green fluorescent protein, GFP) or the colorimetric gene product may be indirectly produced by the reporter gene, such as by enzymatic activity (e.g., β-galactosidase cleaves the yellow substrate chlorophenol red-β-D-galactopyranoside (CPRG) to produce a purple product chlorophenol red (CPR); gradations of the purple color can be produced by increasing activity of the β-galactosidase).

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* (B. D. Hames & S. J. Higgins eds. (1985); *Transcription and Translation* (B. D. Hames & S. J. Higgins, eds. (1984); *Animal Cell Culture* (RI. Freshney, ed. (1986); *Immobilized Cells and Enzymes* (IRL Press, (1986); B. Perbal, *A Practical Guide To Molecular Cloning* (1984); F. M. Ausubel et al. (eds.), *Current Protocols in Molecular Biology*, John Wiley & Sons, Inc. (1994); among others.

Methods of the Disclosure

In one aspect, the disclosure is directed to a method of generating a diagnostic tool for measuring an unknown amount of an analyte in a biological sample using a cell-free extract (CFE), the diagnostic tool comprising a plurality of reference points, each reference point being a distinct color and corresponding to a different amount of the analyte, the method comprising: determining a desired amount of a regulator of a reporter; determining a saturating amount of the analyte; and determining a desired reaction time, wherein the desired amount of the regulator of the reporter, the saturating amount of the analyte, and the desired reaction time are determined such that when the unknown amount of the analyte is combined with the biological sample, the CFE and the desired amount of the regulator of the reporter for the desired reaction time, a colorimetric gene product is generated having a color corresponding to a color of a first reference point in the plurality of reference points containing the biological sample, the CFE, the saturating amount of analyte, and the desired amount of the regulator of the reporter, the first reference point associated with a known amount of the analyte about equal to the unknown amount of analyte. The method can be configured to reduce or eliminate inter-sample variability.

In another aspect, the disclosure is directed to a method for generating a range of visible colors in serum samples with unknown amounts of an analyte by addition of a small molecule, wherein the small molecule displaces an interfering molecule from one or more of a regulator, a reporter, and a molecule acted on by the reporter, the method comprising: determining a desired amount of a regulator of a reporter; determining a saturating amount of the analyte; and determining a desired reaction time, wherein the desired amount of the regulator of the reporter, the saturating amount of the analyte, and the desired reaction time are determined such that when the unknown amount of the analyte is combined with the serum, and the desired amount of the regulator of the reporter for the desired reaction time, a colorimetric gene product is generated having a color corresponding to a color of a first reference point in the plurality of reference points containing the serum, the saturating amount of analyte, and the desired amount of the regulator of the reporter, the first reference point associated with a known amount of the analyte about equal to the unknown amount of analyte. The method can be configured to reduce or eliminate inter-sample variability.

In another aspect, the disclosure is directed to a method of measuring an unknown amount of an analyte in a biological sample using a cell-free extract (CFE), the method comprising: providing a diagnostic tool, the tool comprising a plurality of reference points, each reference point in the plurality of reference points being a distinct color and corresponding to a predetermined different amount of the analyte; combining the biological sample, the CFE, a predetermined saturating amount of the analyte, and a predetermined amount of a regulator of a reporter; reacting the regulator of the reporter with the analyte for a predetermined reaction time to generate a colorimetric gene product; determining a first reference point in the plurality of reference points having a color corresponding to the generated colorimetric gene product, wherein the predetermined different amount of the analyte corresponding to the first reference point is equal to the unknown amount of the analyte in the biological sample added to the CFE. The method can be configured to reduce or eliminate inter-sample variability.

In another aspect, the disclosure is directed to a method of generating a diagnostic tool for measuring an unknown amount of an analyte in an aqueous solution, the diagnostic tool comprising a plurality of reference points, each reference point being a distinct color and corresponding to a different amount of the analyte, the method comprising: determining a desired amount of a regulator of a reporter; determining a saturating amount of the analyte; and determining a desired reaction time, wherein the desired amount of the regulator of the reporter, the saturating amount of the analyte, and the desired reaction time are determined such that when the unknown amount of the analyte is combined with the aqueous solution, and the desired amount of the regulator of the reporter for the desired reaction time, a colorimetric gene product is generated having a color corresponding to a color of a first reference point in the plurality of reference points containing the aqueous solution, the saturating amount of analyte, and the desired amount of the regulator of the reporter, the first reference point associated with an amount of the analyte about equal to the unknown amount of analyte, and wherein the method is configured to reduce or eliminate inter-sample variability.

In another aspect, the disclosure provides a method for generating a range of visible colors in aqueous samples with unknown amounts of an analyte by addition of a small molecule, wherein the small molecule displaces an interfering molecule from one or more of a regulator, a reporter, and a molecule acted on by the reporter, the method comprising: determining a desired amount of a regulator of a reporter; determining a saturating amount of the analyte; and determining a desired reaction time, wherein the desired amount of the regulator of the reporter, the saturating amount of the analyte, and the desired reaction time are determined such that when the unknown amount of the analyte is combined with the aqueous solution, and the desired amount of the regulator of the reporter for the desired reaction time, a colorimetric gene product is generated having a color corresponding to a color of a first reference point in the plurality of reference points containing the aqueous solution, the saturating amount of analyte, and the desired amount of the regulator of the reporter, the first reference point associated with an amount of the analyte about equal to the unknown amount of analyte, and wherein the method is configured to reduce or eliminate inter-sample variability.

In another aspect, the disclosure provides a method of measuring an unknown amount of an analyte in an aqueous solution, the method comprising: providing a diagnostic tool, the tool comprising a plurality of reference points, each reference point in the plurality of reference points being a distinct color and corresponding to a predetermined different amount of the analyte; combining the aqueous solution, a predetermined saturating amount of the analyte, and a predetermined amount of a regulator of a reporter; reacting the regulator of the reporter with the analyte for a predetermined reaction time to generate a colorimetric gene product; determining a first reference point in the plurality of reference points having a color corresponding to the generated colorimetric gene product, wherein the predetermined different amount of the analyte corresponding to the first reference point is equal to the unknown amount of the analyte in the aqueous solution, and wherein the method is configured to reduce or eliminate inter-sample variability.

In any of the foregoing aspects, the method can further comprise one or more of the following embodiments. Each combination is specifically contemplated herein.

In any of the embodiments disclosed herein, the inter-sample variability is reduced or eliminated. This reduction or elimination can be accomplished by addressing the impacts of the sample matrix on accuracy and robustness of quantification by using the biological sample or aqueous solution itself as the sample matrix for the parallel calibration standards. The parallel calibration measurements in the reference points are subject to the same matrix effects as the measurement of the unknown amount in the sample, and so any impacts of those matrix effects should be similar between the reference points and the test samples. Thus, the reference points constitute a sample-specific calibration curve that includes and/or accounts for and/or controls for matrix effects inherent to the test sample. While the raw value of the reporter (colorimetric or detectable output such as fluorescence or absorbance) may vary between samples with identical concentrations due to sample matrix effects, its relative position within the calibration curve should not change drastically, thus reducing and/or eliminating the inter-sample variability for the final readout.

In any of the embodiments disclosed herein, the method can further comprise providing the plurality of reference points. In some embodiments, the plurality of reference points is arranged in the form of a matrix, e.g., having multiple rows and/or columns. In some embodiments, the plurality of reference points is established according to a linear gradient.

In any of the embodiments disclosed herein, the step of determining the desired reaction time can further comprise: adding certain concentrations of the analyte to a plurality of reaction points, each of the plurality of reaction points containing the same amount of the regulator of the reporter and the CFE and the biological sample and or aqueous solution; analyzing color and/or absorbance of the plurality of reaction points over time; plotting the color and/or absorbance of the plurality of reaction points over time versus the concentrations of the analyte; and determining which time point yields a color and/or absorbance output spanning a desired range of absorbances across the analyte concentration range.

In any of the embodiments disclosed herein, the step of determining the desired reaction time can further comprise calculating the total difference in color and/or absorbance output between the plurality of reaction points and one or more test reactions and choosing which pairs have the lowest total error.

In any of the embodiments disclosed herein, the step of determining the saturating amount of the analyte can further comprise: adding certain amounts of the analyte to a plurality of reaction points containing the same amount of the regulator of the reporter and the CFE and the biological sample and or aqueous solution; analyzing color and/or absorbance of the plurality of reaction points over a time course; plotting the color and/or absorbance of the plurality of reaction points versus the reaction time; and determining which amounts of the analyte yield substantially similar color and/or absorbance output throughout the time course.

In any of the embodiments disclosed herein, the step of determining the amounts of the regulator of the reporter can further comprise: adding certain amounts of the regulator to a plurality of reaction points containing a certain amount of the analyte and the CFE and the biological sample and or aqueous solution; analyzing color and/or absorbance of the plurality of reaction points over a time course; plotting the color and/or absorbance of the plurality of reaction points versus the reaction time; and determining which amounts of the regulator of the reporter yield color and/or absorbance outputs throughout the time course that are substantially similar to the color and/or absorbance outputs throughout a time course of different amounts of analyte.

In any of the embodiments disclosed herein, the step of determining the amount of the regulator of the reporter can further comprise calculating the best-fit reaction for each amount of the regulator of the reporter to include in the series of the standard reference reactions, the calculating step comprising: calculating the sum of squared error (SSE) minimization between each standard and test reaction at a series of time points spanning the determined reaction time, wherein the standard reaction that has the lowest SSE is determined to be the best-fit reaction for that amount of the regulator of the reporter.

In any of the embodiments disclosed herein, the biological sample can be a biological fluid sample. In some embodiments, the biological fluid sample can be selected from the group consisting of blood, serum, plasma, urine, saliva, tears, mucus, lymph, interstitial fluid, cerebrospinal fluid, pus, breast milk, and amniotic fluid.

In any of the embodiments disclosed herein, the aqueous solution can be water. In some embodiments, the water is taken from a lake, an ocean, a river, a source of potable water, wastewater, rainwater runoff, or an industrial discharge, effluent, or waste stream.

In any of the embodiments disclosed herein, the reporter can be plasmid-based or can be present on a linear fragment of DNA. In any of the embodiments disclosed herein, the plasmid-based reporter can comprise the regulator and a reporter gene operatively linked to a genetic element that is regulated by the regulator. In any of the embodiments disclosed herein, the linear fragment of DNA can comprise the regulator and a reporter gene operatively linked to a genetic element that is regulated by the regulator. In any of the embodiments disclosed herein, the regulator can comprise a transcription factor, a repressor, and an activator. In any of the embodiments disclosed herein, the genetic element can comprise a promoter, one or more regulatory protein binding sites, one or more repressor binding sites, and one or more transcription factor binding sites.

In any of the embodiments disclosed herein, the reporter gene can produce a quantifiable or detectable gene product. In any of the embodiments disclosed herein, the quantifiable or detectable gene product can be a colorimetric gene product. In any of the embodiments disclosed herein, the colorimetric gene product can comprise a fluorescent protein, a luminescent protein, a colored protein, a protein that produces a detectable and quantifiable product, and a protein that can be quantified by measuring its absorbance at a wavelength. In any of the embodiments disclosed herein, the quantifiable or detectable gene product can be produced directly by the reporter gene. In any of the embodiments disclosed herein, the quantifiable or detectable gene product can be produced indirectly by the reporter gene, e.g., by enzymatic activity of the reporter gene.

In any of the embodiments disclosed herein, the analyte being measured in the biological sample with the CFE can be zinc. In any of the embodiments disclosed herein, the reporter can comprise a first plasmid containing a transcriptional regulator ZntR and a second plasmid containing a reporter gene operatively linked to a ZntA promoter, wherein expression from the ZntA promoter is controlled by the amount of the transcriptional regulator ZntR.

In any of the embodiments disclosed herein, the analyte being measured in the biological sample with the CFE can be RNA. In any of the embodiments disclosed herein, the plasmid-based reporter can comprise a first plasmid containing a toehold switch activated by a trigger RNA sequence that is operatively linked to a reporter gene, wherein expression of the reporter gene is controlled by the amount of the trigger RNA sequence.

In any of the embodiments disclosed herein, the analyte in the aqueous solution can be lead, mercury, or other heavy metal in an aqueous solution such as potable water. Suitable detection systems are described in, e.g., Alam et al., Rapid, Low-Cost Detection of Water Contaminants Using Regulated In Vitro Transcription (2019) bioRxiv 619296; doi: https://doi.org/10.1101/619296.

In any of the embodiments disclosed herein, a small molecule can be added to the CFE or aqueous solution to displace an interfering molecule (e.g., protein, DNA, RNA) from one or more of the regulator, the reporter, and a molecule acted on by the reporter. In some embodiments, the small molecule can be a colorless compound that tightly interacts with the interfering molecule, such as serum albumin, including but not limited to a variety of antibiotics. In any of the embodiments disclosed herein, the small molecule can be naproxen.

Diagnostic Tools of the Disclosure

In one aspect, the disclosure provides a diagnostic tool for measuring an unknown amount of an analyte in a biological sample with a cell-free extract (CFE), the tool comprising: a first reference point having a first distinct color corresponding to a first amount of the analyte; a second reference point having a second distinct color corresponding to a second amount of the analyte; and a third reference point having a third distinct color corresponding to a third amount of the analyte, wherein the first distinct color is substantially similar to a colorimetric gene product generated when a biological sample with the first amount of the analyte is combined with the CFE, a predetermined amount of a regulator of a reporter and a predetermined saturation amount of the analyte for a predetermined reaction time, wherein the second distinct color is substantially similar to a colorimetric gene product generated when a biological sample with the second amount of the analyte is combined with the CFE, the predetermined amount of the regulator of a reporter and the predetermined saturation amount of the analyte for the predetermined reaction time, wherein the third distinct color is substantially similar to a colorimetric gene product generated when a biological sample with the third amount of the analyte is combined with the CFE, the predetermined amount of the regulator of a reporter and the predetermined saturation amount of the analyte for the predetermined reaction time. The diagnostic tool can be configured to reduce or eliminate inter-sample variability.

In another aspect, the disclosure provides a diagnostic tool for measuring an unknown amount of an analyte in an aqueous solution, the tool comprising: a first reference point having a first distinct color corresponding to a first amount of the analyte; a second reference point having a second distinct color corresponding to a second amount of the analyte; and a third reference point having a third distinct color corresponding to a third amount of the analyte, wherein the first distinct color is substantially similar to a colorimetric gene product generated when an aqueous solution with the first amount of the analyte is combined with a predetermined amount of a regulator of a reporter and a predetermined saturation amount of the analyte for a predetermined reaction time, wherein the second distinct color is substantially similar to a colorimetric gene product generated when an aqueous solution with the second amount of the analyte is combined with the predetermined amount of the regulator of a reporter and the predetermined saturation amount of the analyte for the predetermined reaction time, wherein the third distinct color is substantially similar to a colorimetric gene product generated when an aqueous solution with the third amount of the analyte is combined with the predetermined amount of the regulator of a reporter and the predetermined saturation amount of the analyte for the predetermined reaction time. The diagnostic tool can be configured to reduce or eliminate inter-sample variability.

In any of the foregoing aspects, the diagnostic tool can further comprise one or more of the following embodiments. Each combination is specifically contemplated herein.

In any of the embodiments disclosed herein, the inter-sample variability is reduced or eliminated. This reduction or elimination can be accomplished by addressing the impacts of the sample matrix on accuracy and robustness of quantification by using the biological sample or aqueous solution itself as the sample matrix for the parallel calibration standards. The parallel calibration measurements in the reference points are subject to the same matrix effects as the measurement of the unknown amount in the sample, and so any impacts of those matrix effects should be similar between the reference points and the test samples. Thus, the reference points constitute a sample-specific calibration curve that includes and/or accounts for and/or controls for matrix effects inherent to the test sample. While the raw value of the reporter (colorimetric or detectable output such as fluorescence or absorbance) may vary between samples with identical concentrations due to sample matrix effects, its relative position within the calibration curve should not change drastically, thus reducing and/or eliminating the inter-sample variability for the final readout.

In any of the embodiments disclosed herein, the diagnostic tool further can comprise providing the plurality of reference points. In some embodiments, the plurality of reference points is arranged in the form of a matrix, e.g., with multiple rows and/or columns. In some embodiments, the plurality of reference points is established according to a linear gradient.

In any of the embodiments disclosed herein, the step of determining the predetermined reaction time can comprise: adding certain concentrations of the analyte to a plurality of reaction points, each of the plurality of reaction points containing the same amount of the regulator of the reporter and the CFE and the biological sample and or aqueous solution; analyzing color and/or absorbance of the plurality of reaction points over time; plotting the color and/or absorbance of the plurality of reaction points over time versus the concentrations of the analyte; and determining which time point yields a color and/or absorbance output spanning a desired range of absorbances across the analyte concentration range.

In any of the embodiments disclosed herein, the step of determining the predetermined reaction time can further comprise calculating the total difference in color and/or absorbance output between the plurality of reaction points and one or more test reactions and choosing which pairs have the lowest total error.

In any of the embodiments disclosed herein, the step of determining the predetermined saturating amount of the analyte can further comprise: adding certain amounts of the analyte to a plurality of reaction points containing the same amount of the regulator of the reporter and the CFE and the biological sample and or aqueous solution; analyzing color and/or absorbance of the plurality of reaction points over a time course; plotting the color and/or absorbance of the plurality of reaction points versus the reaction time; and determining which amounts of the analyte yield substantially similar color and/or absorbance output throughout the time course.

In any of the embodiments disclosed herein, the step of determining the predetermined amounts of the regulator of the reporter can further comprise: adding certain amounts of the regulator to a plurality of reaction points containing a certain amount of the analyte and the CFE and the biological sample and or aqueous solution; analyzing color and/or absorbance of the plurality of reaction points over a time course; plotting the color and/or absorbance of the plurality of reaction points versus the reaction time; and determining which amounts of the regulator of the reporter yield color and/or absorbance outputs throughout the time course that are substantially similar to the color and/or absorbance outputs throughout a time course of different amounts of analyte.

In any of the embodiments disclosed herein, the step of determining the predetermined amount of the regulator of the reporter can further comprise calculating the best-fit reaction for each amount of the regulator of the reporter to include in the series of the standard reference reactions, the calculating step comprising: calculating the sum of squared error (SSE) minimization between each standard and test reaction at a series of time points spanning the determined reaction time, wherein the standard reaction that has the lowest SSE is determined to be the best-fit reaction for that amount of the regulator of the reporter.

In any of the embodiments disclosed herein, the biological sample can be a biological fluid sample. In any of the embodiments disclosed herein, the biological fluid sample can be selected from the group consisting of blood, serum, plasma, urine, saliva, tears, mucus, lymph, interstitial fluid, cerebrospinal fluid, pus, breast milk, and amniotic fluid.

In any of the embodiments disclosed herein, the aqueous solution can be water. In any of the embodiments disclosed herein, the water can be taken from a lake, an ocean, a river, a source of potable water, wastewater, rainwater runoff, or an industrial discharge, effluent, or waste stream.

In any of the embodiments disclosed herein, the reporter can be plasmid-based or can be present on a linear fragment of DNA. In any of the embodiments disclosed herein, the plasmid-based reporter can comprise the regulator and a reporter gene operatively linked to a genetic element that is regulated by the regulator. In any of the embodiments disclosed herein, the linear fragment of DNA can comprise the regulator and a reporter gene operatively linked to a genetic element that is regulated by the regulator. In any of the embodiments disclosed herein, the regulator can comprise a transcription factor, a repressor, and an activator. In any of the embodiments disclosed herein, the genetic element can comprise a promoter, one or more regulatory protein binding sites, one or more repressor binding sites, and one or more transcription factor binding sites.

In any of the embodiments disclosed herein, the reporter gene can produce a quantifiable or detectable gene product. In any of the embodiments disclosed herein, the quantifiable or detectable gene product can be a colorimetric gene product. In any of the embodiments disclosed herein, the colorimetric gene product can comprise a fluorescent protein, a luminescent protein, a colored protein, a protein that produces a detectable and quantifiable product, and a protein that can be quantified by measuring its absorbance at a wavelength. In any of the embodiments disclosed herein, the quantifiable or detectable gene product can be produced directly by the reporter gene. In any of the embodiments disclosed herein, the quantifiable or detectable gene product can be produced indirectly by the reporter gene, e.g., by enzymatic activity of the reporter gene.

In any of the embodiments disclosed herein, the analyte being measured in the biological sample with the CFE can be zinc. In any of the embodiments disclosed herein, the reporter can comprise a first plasmid containing a transcriptional regulator ZntR and a second plasmid containing a reporter gene operatively linked to a ZntA promoter, wherein expression from the ZntA promoter is controlled by the amount of the transcriptional regulator ZntR.

In any of the embodiments disclosed herein, the analyte being measured in the biological sample with the CFE can be RNA. In any of the embodiments disclosed herein, the plasmid-based reporter can comprise a first plasmid containing a toehold switch activated by a trigger RNA sequence that is operatively linked to a reporter gene, wherein expression of the reporter gene is controlled by the amount of the trigger RNA sequence.

In any of the embodiments disclosed herein, the analyte in the aqueous solution can be lead, mercury, or other heavy metal in an aqueous solution such as potable water. Suitable detection systems are described in, e.g., Alam et al., Rapid, Low-Cost Detection of Water Contaminants Using Regulated In Vitro Transcription (2019) bioRxiv 619296; doi: https://doi.org/10.1101/619296.

In any of the embodiments disclosed herein, a small molecule can be added to the CFE or aqueous solution to displace an interfering molecule (e.g., protein, DNA, RNA) from one or more of the regulator, the reporter, and a molecule acted on by the reporter. In any of the embodiments disclosed herein, the small molecule can be a colorless compound that tightly interacts with the interfering molecule, such as serum albumin, including but not limited to a variety of antibiotics. In any of the embodiments disclosed herein, the small molecule can be naproxen.

EXAMPLES

The present invention is also described and demonstrated by way of the following examples. However, the use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

Example 1: Development of a Cell Free Expression-Based Assay for a Biomarker This Example describes the development of a cell-free expression diagnostic platform that accurately quantifies biomarkers in human serum, including diluted and undiluted human serum.

Materials and Methods

Construction of Zinc-Responsive Circuit

Three plasmids were assembled through Gibson assembly: one in which the transcription factor ZntR was under the control of a standard T7 promoter, one in which $P_{zntA}$ controlled sfGFP production, and one in which $P_{zntA}$ controlled β-galactosidase production. ZntR and $P_{zntA}$ were amplified from a previously described circuit. β-galactosidase was amplified from BL21(DE3) genomic DNA, and sfGFP was amplified from the plasmid pJL1. All operons were cloned into a plasmid containing a ColE1 origin and a kanamycin resistance cassette. All primers and plasmid sequences can be found in the Supplementary Information. All plasmids were purified with EZNA midiprep columns and sequence confirmed.

Construction of Knockout Strains

Lambda red recombination was used to make all knockout strains. The kanamycin resistance cassette was amplified from the plasmid pKD4 using primers that contained the P1 and P2 priming sequences specified in Datsenko and Wanner and an additional 50 nucleotides of the appropriate upstream (P1) or downstream (P2) homologous sequence for the specific knockout. The PCR product was gel-purified and transformed via electroporation into cells that contained the plasmid pDK46, which expresses the lambda red recombinase under control of the $P_{Bad}$ promoter. Two knockout strains were constructed: a strain with the full Lac operon deleted was constructed to make BL21(DE3) ΔlacIZYA, and a dual knockout strain with zntR deleted was also constructed to make BL21(DE3) ΔlacIZYA ΔzntR. Successful knockouts were selected for on kanamycin plates, and replacement of the target gene with the kanamycin cassette was confirmed via PCR. The kanamycin selection marker was not excised. For the dual knockout strain, zntR was first knocked out and selected for via antibiotic resistance. Then, lacIZYA was knocked out, and blue-white screening and PCR were used to confirm successful knockouts.

Preparation of Cellular Lysate

Cellular lysate for all experiments, excluding toehold switch experiments, was prepared. BL21(DE3) ΔlacIZYA ΔzntR cells were grown in 2×YTPG medium at 37° C. and 180 rpm to an OD of 2.0, which corresponded with the mid-exponential growth phase. Cells were then centrifuged at 2700 rcf and washed three times with S30 buffer. S30 buffer contains 10 mM Tris-acetate (pH 8.2), 14 mM magnesium acetate, 60 mM potassium acetate, and 2 mM dithiothreitol. After the final centrifugation, the wet cell mass was determined, and cells were resuspended in 1 mL of S30 buffer per 1 g of wet cell mass. The cellular resuspension was divided into 1 mL aliquots. Cells were lysed using a Q125 Sonicator (Qsonica, Newton, Conn.) at a frequency of 20 kHz, and at 50% of amplitude. Cells were sonicated on ice with three cycles of 10 seconds on, 10 seconds off, delivering approximately 180 J, at which point the cells appeared visibly lysed. An additional 4 mM of dithiothreitol was added to each tube, and the sonicated mixture was then centrifuged at 12,000 rcf and 4° C. for 10 minutes. The supernatant was removed, aliquoted, and stored at −80° C. for future use.

Cell-Free Reactions: Constitutive Expression and Zinc-Sensing

Cell-free reactions for all experiments, excluding toehold switch reactions, were run. Each cell-free reactions contained 0.85 mM each of GTP, UTP, and CTP, in addition to 1.2 mM ATP, 34 μg/mL of folinic acid, 170 μg/mL E. coli tRNA mixture, 130 mM potassium glutamate, 10 mM ammonium glutamate, 12 mM magnesium glutamate, 2 mM each of the 20 standard amino acids, 0.33 mM nicotine adenine dinucleotide (NAD), 0.27 mM coenzyme-A (CoA), 1.5 mM spermidine, 1 mM putrescine, 4 mM sodium oxalate, 33 mM phosphoenol pyruvate (PEP), 27% cell extract, and the specified concentration of plasmids. In all reactions producing β-galactosidase, CPRG was added to a final concentration of 0.6 mg/ml. All chemicals were purchased from Sigma Aldrich. In reactions containing human serum, RNase inhibitor (NEB) was added to a concentration of 0.6 U/μl.

In all reactions producing GFP, plasmids were added to reactions at a final concentration of 20 ng/μL. Plasmid dosage of β-galactosidase and ZntR expression plasmids (pLacZ and pZntR) was optimized so that color change would be observable at approximately 60 minutes. In reactions without serum, pLacZ was added at a concentration of 1.0 ng/μL when ZntR was pre-expressed, and at a concentration of 1.5 ng/μL when ZntR was co-expressed. When ZntR was co-expressed in reactions without serum, pZntR was added to reactions at a concentration of 0.5 ng/μL. In all reactions with serum, pLacZ was added at a concentration of 15 ng/μL, and pZntR was added at a concentration of 2.5 ng/ul.

In experiments in which ZntR was pre-expressed and added to the reaction (FIGS. S11 and S12), ZntR was first produced overnight in a cell-free reaction. Reactions were carried out in 1.5 mL microcentrifuge tubes, and the reaction volume in each tube was 50 μL. A plasmid expressing ZntR (pZntR) was added at 20 ng/μl, and a plasmid expressing a ZntR-GFP fusion protein was added at 1 ng/μl as a way to assess the output of the reaction. Reactions were incubated at 30° C. for 16 hours. Reactions were then centrifuged at 12,000 rcf and 4° C. for 10 minutes, and the supernatant was removed and subsequently used. Based on the assumptions that the transcriptional rates of both ZntR and the ZntR-GFP fusion protein are identical (since they have the same promoter) and that the translational rates of both proteins are identical (since they have the same 5' UTR and initial coding sequence), fluorescence was used as a proxy measurement for total ZntR production. Though these fluorescent measurements give an arbitrary approximation of final ZntR production and not an absolute concentration, they enable easy and fast comparison across different cell-free expression reactions. To measure fluorescence, each reaction was diluted by a factor of 10 in nuclease-free ultrapure water. 10 μL was added to a well of a 384 well plate, and the fluorescence was measured with a plate reader (Synergy4, BioTek). Excitation and emission for sfGFP were 485 and 528 nm, respectively. Fluorescence values were used to account for batch-to-batch variations so that a constant amount of ZntR was added to each reaction. Unless otherwise specified, the overnight ZntR reaction was added to fresh reactions at a concentration of 1% (+/− variations of less than 0.05% determined through fluorescent quantification measurements).

Cell-free expression reactions were run in 8 μl volumes in 384 well small volume plates (Greiner Bio-One), and a clear adhesive film was used to cover the plate and prevent evaporation. Fluorescence of GFP was quantified as described above. β-galactosidase activity was monitored by measuring absorbance at 580 nm. For time course experiments, plates were incubated at 37° C., and either fluorescence or absorbance was measured every two minutes. For end-point experiments, plates were incubated at 37° C., and fluorescence was measured after 22 hours.

Determination of Best-Fit Reactions and Predictive Standard Reactions

In determining which standard reference reaction best fit each zinc concentration, sum of squared error (SSE) minimization was used. The difference between each standard and test reaction was calculated at all time points between 30 and 90 minutes. The SSE was calculated over this time frame, and the standard reaction that had the lowest SSE was determined to be the best-fit reaction and thus the optimal regulator for that experimental run. When choosing what regulator concentration best predicts each potential biomarker concentration, we determined the overall optimal regulator concentration as the one closest to the average of the optimal matching regulator concentration across three runs.

Preparation of Human Serum

Pooled human serum was purchased from Corning. Chelex 100 (BioRad) was used to deplete zinc from the serum. 1 g of resin was added to 100 ml of serum, and serum was stirred for 2 hours. Resin was removed from serum through filtration.

In single donor experiments, blood was collected from donors as approved in IRB protocol number H17489. Venous blood was collected in 6 ml BD Vacutainer collection tubes for trace element testing, and tubes were left on ice for 30 minutes to clot. Blood was then transferred to a 50 ml conical tube and centrifuged at 2700 rcf, 4° C. for 30 minutes. The serum was removed and either immediately frozen or treated with Chelex-100 resin. 80 mg of resin was added to 8 ml of serum, and the mixture was vigorously stirred for 2 hours. Resin was isolated from the samples through centrifugation, and serum was syringe filtered. All serum samples were aliquoted to minimize freeze-thaw cycles and stored at −20° C.

Zinc Measurements

Zinc concentration of pooled serum was analyzed using an X-Ray Fluorescence spectrometer. 2 µl of serum was spiked with 1 ppm of a gallium internal standard, pipetted onto a quartz disc, and atomic fluorescence emission spectra were collected. Zinc concentration in individual donor serum samples was measured at the University of Georgia Laboratory for Environmental Analysis. Samples were digested with concentrated acid and analyzed on an ICP-MS according to EPA method 3052.

Spectra Analysis

To analyze the spectrum of chlorophenol red and reaction intermediates, a large batch of concentrated chlorophenol red was made by adding CPRG to a small amount of extract made from standard BL21(DE3) cells (which have high baseline β-galactosidase activity). The spectrum of CPR was analyzed to ensure that all CPRG reacted to CPR by screening for absence of a detectable peak at 410 nm. Different combinations of CPRG and CPR were then added to solutions containing 27% bacterial cell extract (made from BL21(DE3) ΔlacIZYA cells), with or without serum. The final concentration of dye in each solution analyzed was 1.02 µM, which corresponds with addition of 0.6 mg/ml of CPRG.

When adding small molecules to the reaction, 10× stocks of each molecule were made. Penicillin, dicloxacillin, and naproxen were dissolved in water, ibuprofen was dissolved in ethanol, and sulfisoxazole was dissolved in chloroform. 3 µL of each stock was added to PCR tubes, and tubes were left open in a fume hood overnight so that solvents could evaporate. A 30 µL solution containing the specified amount of dye, protein extract, and serum was used to re-dissolve the small molecule. Concentrations reported are the final concentration of small molecule in the analyzed solutions.

The spectra of all solutions reported were measured in triplicate with a Nanodrop 2000. When analyzing reaction intermediates, spectrum height was normalized to a peak at 280 nm. When further analyzing the peak corresponding with CPR, each spectrum was first height-normalized so that the maximum of the peak corresponding with chlorophenol red was the same for all spectra. Then, the wavelengths that correspond with 4 different absorbance intensities were determined and subtracted from the values of the control spectrum. The four differences were averaged to compute the overall wavelength shift. Reported averages are the average of the overall wavelength shift of the three initial replicates.

Color Imaging and Processing

All pictures were taken with a Panasonic Lumix camera in a light-controlled setting. All pictures in figures showing color results are of 8 µL reactions in 384 well plates. The centers of selected reaction wells were cropped using Adobe Photoshop and combined to make color arrays. A brightness filter was uniformly applied to photos to make them better resemble actual appearance.

Lyophilization

30 µL reactions containing all components of the cell-free reaction (including lysate, small molecule mix, DNA templates, and CPRG) at a 1× concentration were prepared in PCR tubes and flash frozen in liquid nitrogen. Frozen samples were removed from liquid nitrogen and added to a Labconco Fast-freeze flask that contained a small amount of liquid nitrogen. Care was taken to transfer samples quickly and keep samples cold throughout the transfer process. Flasks were connected to a LabConco benchtop freeze-drier and lyophilized at −50° C. and 0.05 mbar for 3 hours. Samples were then removed and rehydrated on ice.

Results

Matrix Effects in Cell-Free Diagnostics

With the ultimate goal of developing quantitative equipment-free diagnostics (regardless of matrix effects), the inventors first sought to develop a clinically relevant testbed to demonstrate the potential of cell-free expression to accomplish this goal. The inventors chose to use zinc as the model analyte because of its global health relevance (zinc deficiency kills 100,000 children under the age of five every year), the inventors' previous experience in developing whole-cell zinc biosensors, and the lack of field-deployable zinc diagnostics. Current clinical assessment of zinc levels requires high-pressure acid digestion and analysis with a mass spectrometer, a process that is costly and equipment-intensive.

To begin, the inventors tested whether zinc-responsive elements could properly control output in a cell-free expression reaction. A regulator plasmid (pZntR) that constitutively expressed the zinc-responsive activator ZntR and a reporter plasmid (pGFP) that contains GFP under control of ZntR's cognate promoter $P_{zntA}$ was constructed. When both plasmids were added to a cell-free expression reaction, the system showed a dose-dependent zinc response between 0 and 8 µM, demonstrating that zinc can be detected in a cell-free system. Notably, the system also shows a dramatic decrease in protein production at higher zinc concentrations. This trend was attributed to decreased expression from native *E. coli* σ$_{70}$ promoters at high zinc concentrations, based on similar observations for constitutive *E. coli* σ$_{70}$ promoters.

Figure 1B:
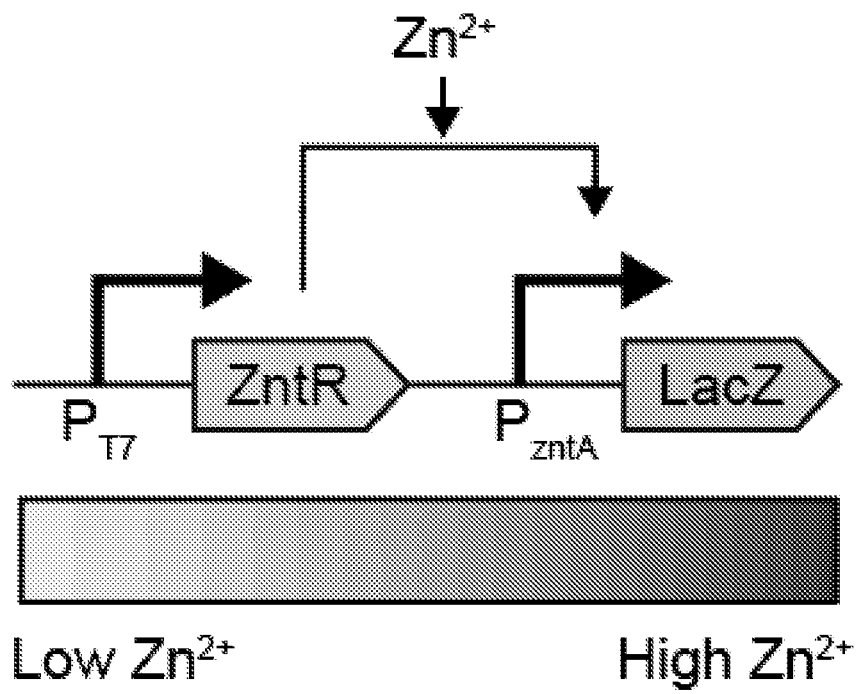
Figure 1C:
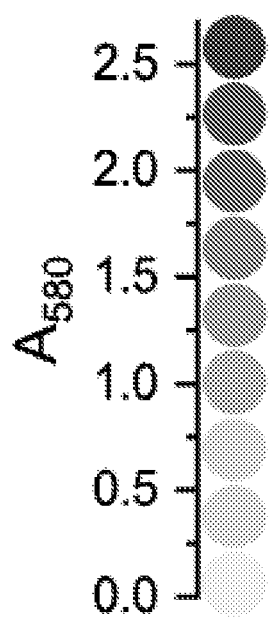
Figure 1D:
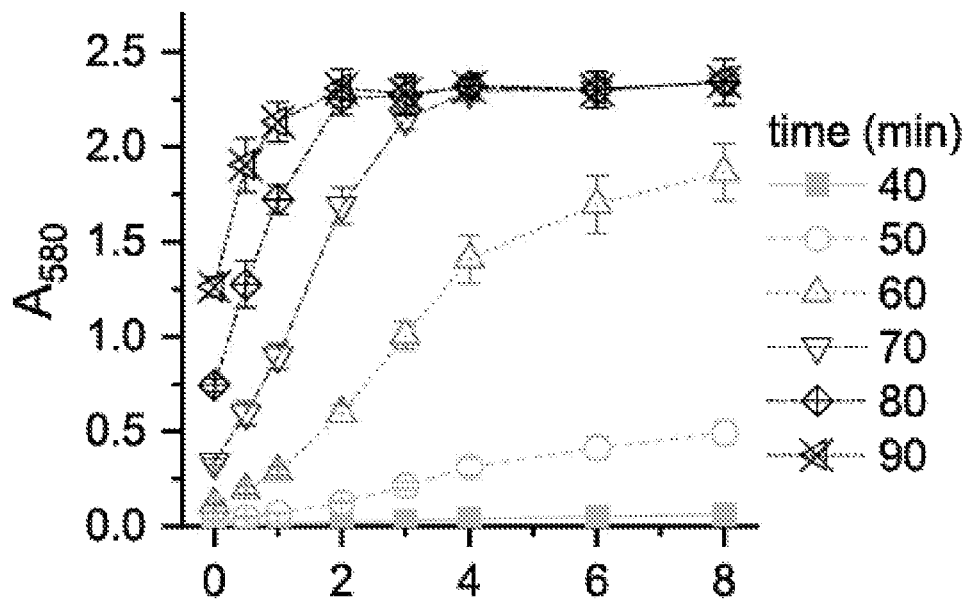
Figure 5:
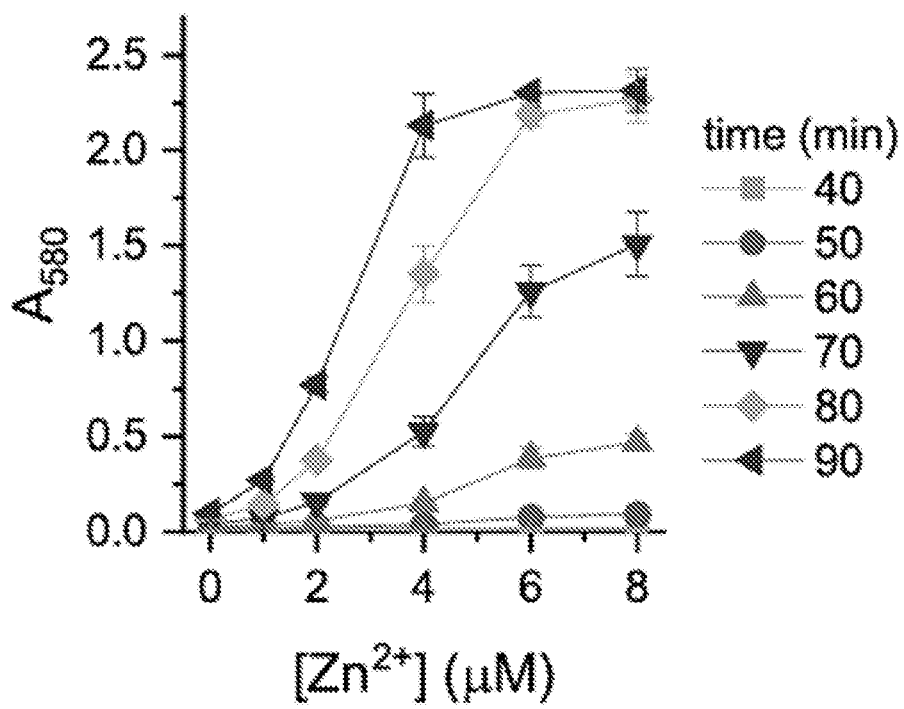
FIG. 5 shows zinc response in lyophilized reactions. The quantitative colorimetric response to zinc of lyophilized reactions that were rehydrated in different zinc concentrations is shown. Though the response was slightly slower than fresh reactions, the system showed a zinc response similar to that of reactions run without lyophilization.

To better enable equipment-free testing, the inventors replaced the GFP reporter with β-galactosidase to create a plasmid (pLacZ) that can mediate a colorimetric output (FIG. 1B). β-galactosidase cleaves the yellow substrate chlorophenol red-β-D-galactopyranoside (CPRG) to the purple product chlorophenol red (CPR); this enzyme/substrate pair has previously been used in the development of low-resource diagnostic tools. Colorimetric output was quantified by measuring absorbance at 580 nm or assessed qualitatively by looking at reaction color (FIG. 1C). The inventors characterized the system's behavior in a bacterial extract with no β-galactosidase or ZntR background activity. All reactions were initially yellow (the color of CPRG), and at intermediate time points, tests were varying shades of yellow, orange, red, and purple based on zinc concentrations (FIG. 1D). Lyophilized systems showed a similar colorimetric response to zinc, a critical requirement for field-friendly deployment (FIG. 5).

Figure 6:
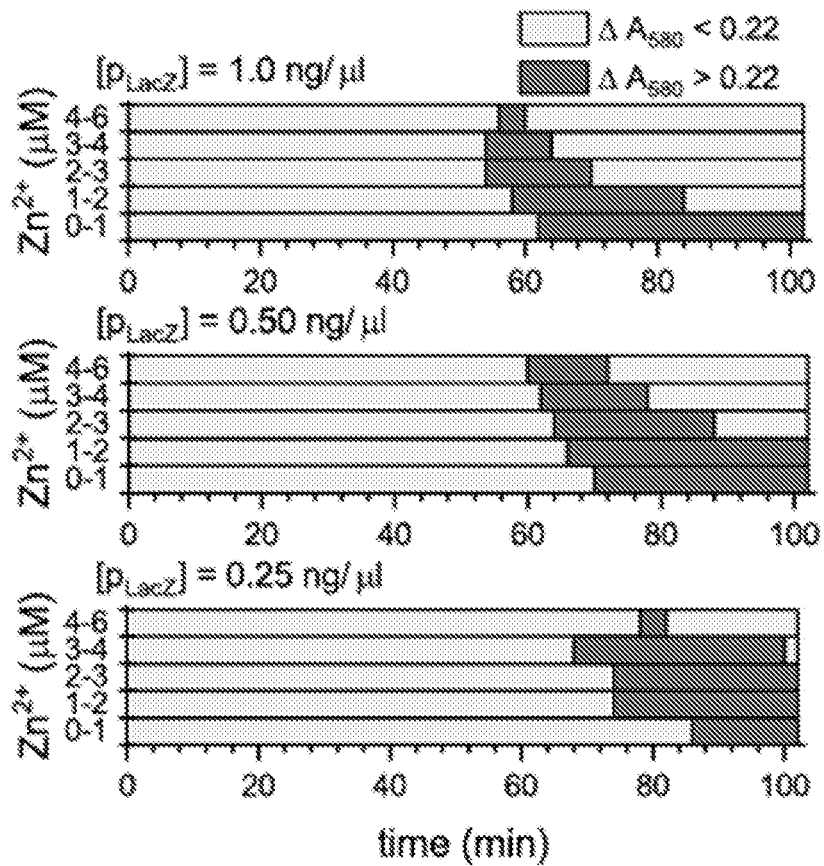
FIG. 6 shows the effect of reporter plasmid concentration on ability to distinguish between different zinc concentrations. Zinc concentrations were considered indistinguishable if the difference in A580 readings between two concentrations was less than 0.22 (which corresponded with less than 10% of the range of A580 values, and thus of the total visible spectrum). Times highlighted in dark grey indicate that the absorbance difference between the two concentrations on the y-axis was above this threshold and thus the user can visually detect colorimetric differences between the two concentrations. Higher plasmid concentrations enabled faster time to visible differences, but the differences are visible for shorter periods of time.

To tune reaction timing for detection purposes, the inventors modulated the concentration of reporter plasmid in the reaction. As expected, higher concentrations of the reporter plasmid (pLacZ) decreased the incubation time required for visible color, though they also decreased the time interval over which a dose-dependent zinc response (color difference) is detectable (FIG. 6). Thus, plasmid dosage can be used to create tests that meet the necessary time parameters for a given application. For most experiments, the inventors selected reporter plasmid concentrations that allowed readouts in less than an hour but maximized the time interval over which dose-dependent color differences were evident.

Figure 1E:
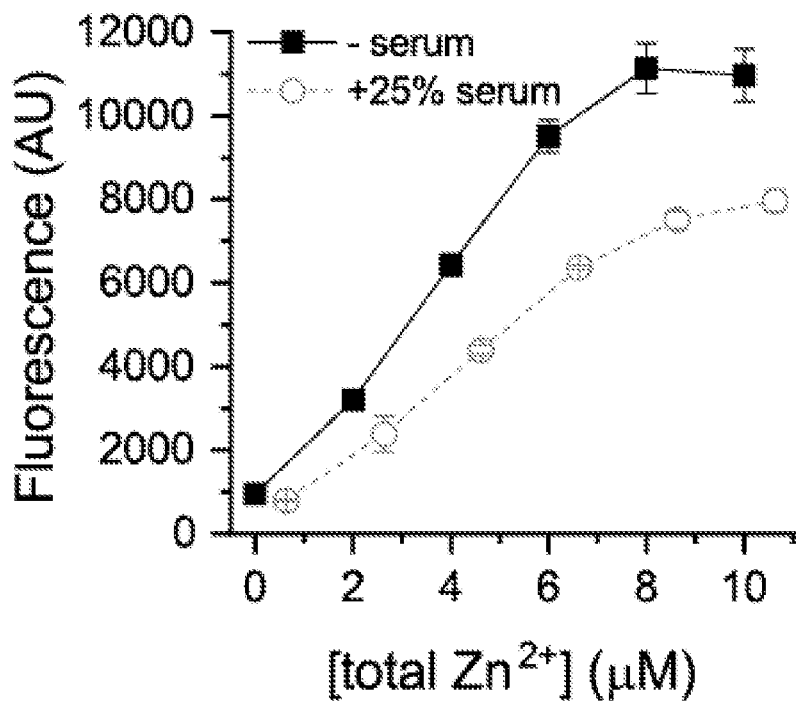
Figure 7A:
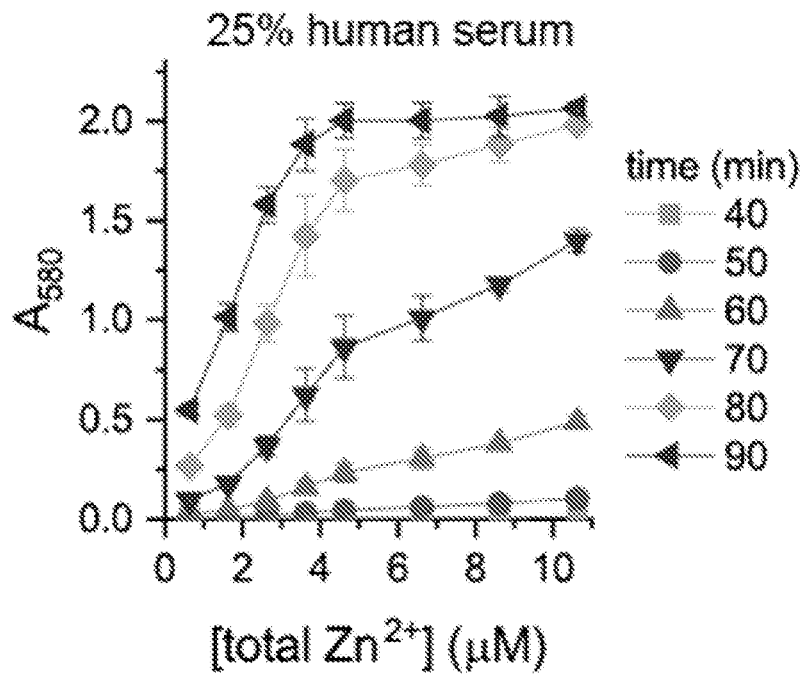
FIG. 7A-7B show quantitative colorimetric responses to reactions run in serum. (7A) Quantitative colorimetric response to zinc in 25% serum. A higher concentration of the plasmid pLacZ was added compared to experiments without serum so that color differences are visible between 60 and 80 minutes. (7B) Quantitative colorimetric response to zinc in lyophilized reactions rehydrated in commercially purchased human serum that contains different amounts of zinc.
Figure 7B:
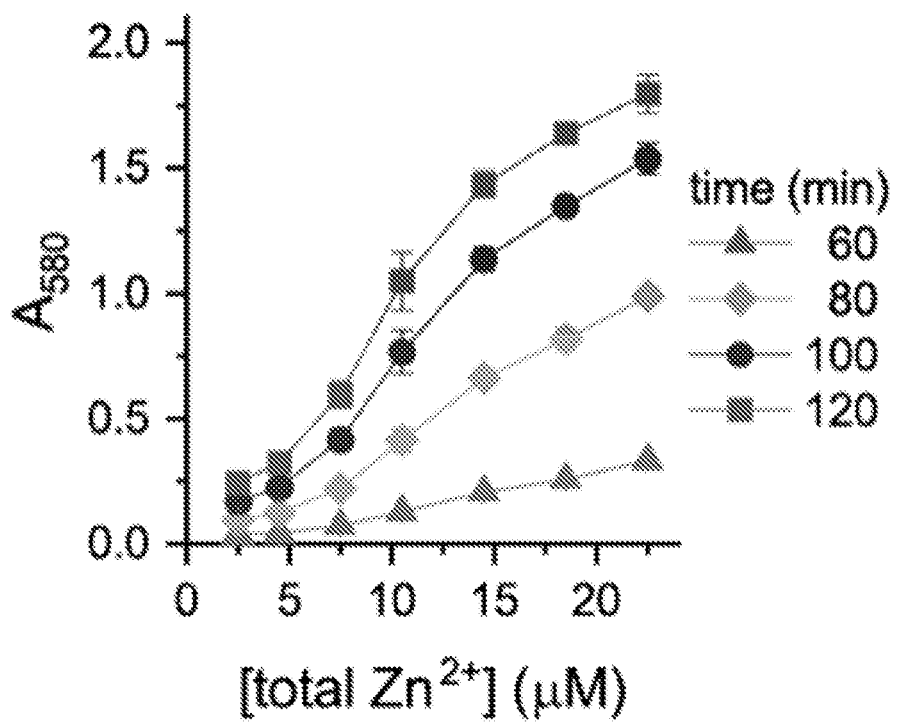

With a cell-free expression zinc sensor in hand, the inventors then sought to test the hypothesis that cell-free expression is prone to substantial matrix effects. While cell-free expression reactions responded to zinc in high concentrations (25%) of serum, the serum matrix dramatically affects test output, reducing protein expression by 25-50% (FIG. 1E). Addition of higher reporter plasmid concentrations enables reactions run in 25% serum and lyophilized reactions that are run in 100% serum to still produce a spectrum of colors across a large range of zinc concentrations (FIG. 7A-7B). However, the dramatically different expression levels of reactions run in serum (compared to reactions run without serum) precluded the use of chemical calibration standards, as they would not exhibit the same matrix effects. Since standards are required for a cell-free expression quantitative diagnostic, a more sophisticated approach to quantification is necessary.

Test Standardization in Complex Matrices

Since an ideal diagnostic would allow the user to match the test's color output to a set of reference colors, accounting for all matrix effects caused by serum samples is important. In addition, since the assay outputs change with time, those reference colors should also change over the course of the test. The inventors next developed a standardization method that addresses both of these issues, so that the color of the test reaction can be matched to an array of standard reactions run in the exact same sample matrix as the test reaction (FIG. 1A).

Figure 1F:
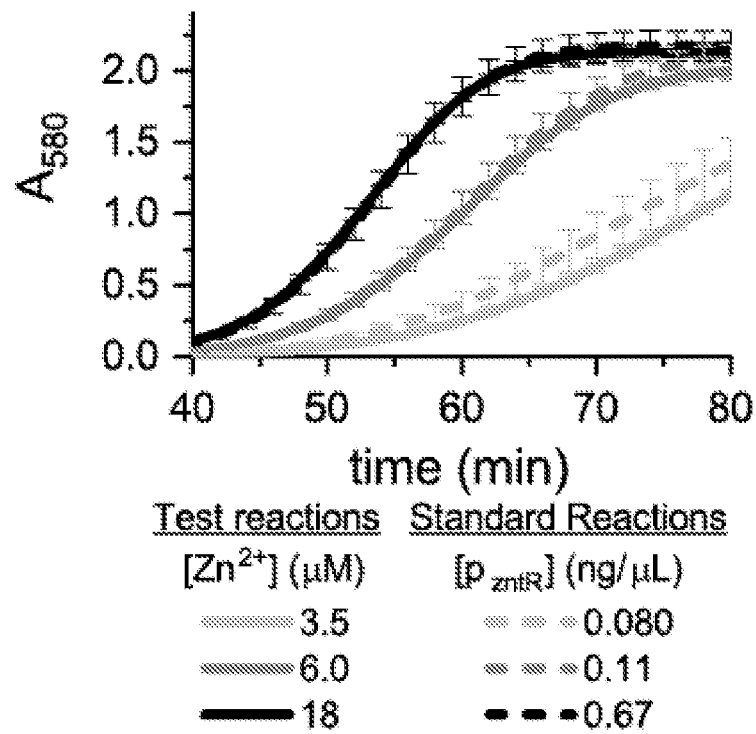

To create such a matrix-specific standardization approach, the inventors designed standard reference reactions so that they have saturated biomarker concentrations and a variable, predetermined amount of the response regulator. The inventors found that the zinc response for a given concentration of the regulator plasmid pZntR saturated above a certain concentration of zinc (FIG. 8), such that additional zinc did not affect colorimetric output. Instead, colorimetric output was solely dependent on the concentration of the transcriptional regulator ZntR, and ZntR levels were controlled by varying the concentration of the regulator plasmid pZntR. This means that reference reactions can be created that have saturated concentrations of zinc and that are thus insensitive to the (unknown) zinc concentrations of whatever sample is added to the reference reactions. A sample to be tested can thus be added to both the test and reference reactions, and any matrix effects of serum on cell-free expression machinery will be identical in both the sample and the reference standards. The output of each reference reaction can then be set by changing the level of ZntR to reproduce the output that the test reaction would yield (at its fixed level of ZntR) for any given zinc concentration (FIG. 1F). Taken together, this allowed for sample-specific calibration for the test reaction.

Figure 8:
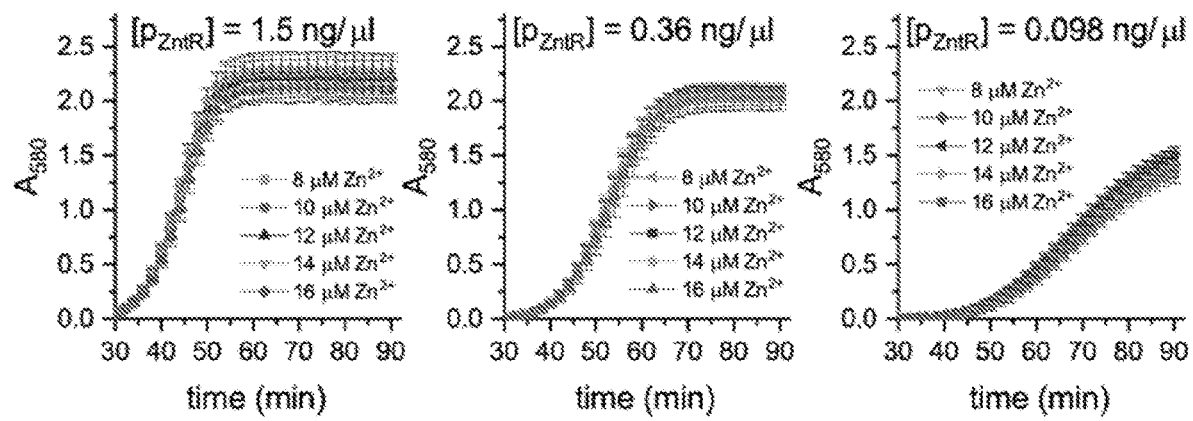
FIG. 8 shows the response to zinc saturates in 25% serum. Colorimetric response was identical across a range of zinc concentrations. Reactions with different regulator concentrations were run in 25% serum that contained a range of zinc concentrations. In all tests run in 25% serum, colorimetric output was the same across the raw range of 8 to 16 μM zinc, which corresponds with 32 to 64 μM zinc in the serum sample.

Specifically, the inventors found that in a 25% serum matrix, colorimetric output is identical across a raw concentration range of 8 to 16 μM added zinc (FIG. 8). If each standard reaction started with 8 μM zinc, and each raw sample added to a standard reaction had no more than 8 μM zinc, then the final standard reactions will have between 8 and 16 μM zinc, and thus have constant output. This enabled tests run in 25% serum to differentiate between 0 and 8 μM raw zinc, corresponding to a clinically relevant serum zinc range of 0 to 32 μM.

Figure 9:
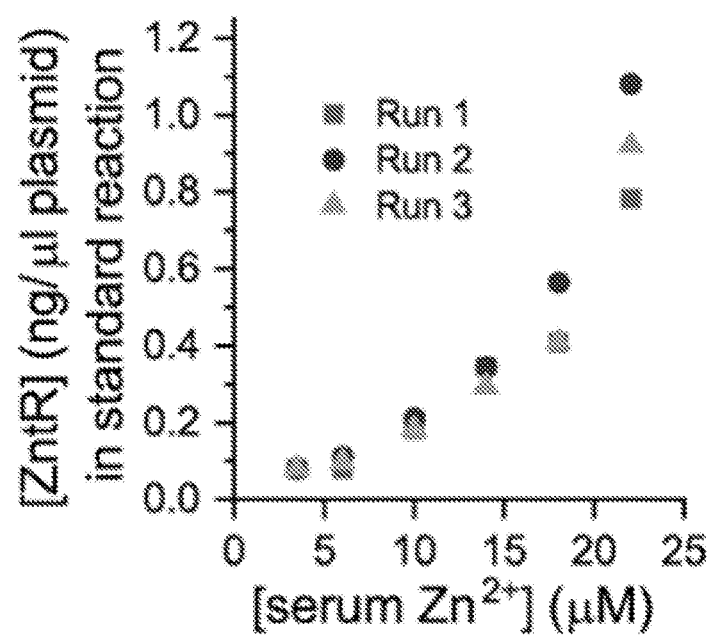
FIG. 9 shows the relationship between regulator in standard reactions and zinc in test reactions. Scatter plot of zinc concentrations and the corresponding regulator concentrations that yielded similar output in 25% human serum. Runs 1-3 represent experiments performed separately and in different batches of cell extract. Zinc values reported are the equivalent of those in the pure serum samples, translated from the raw values measured by the reactions. The inventors chose the optimal regulator concentration to correspond with each potential test result as the one closest to the average of the optimal matching regulator concentration across three runs.
Figure 10A:
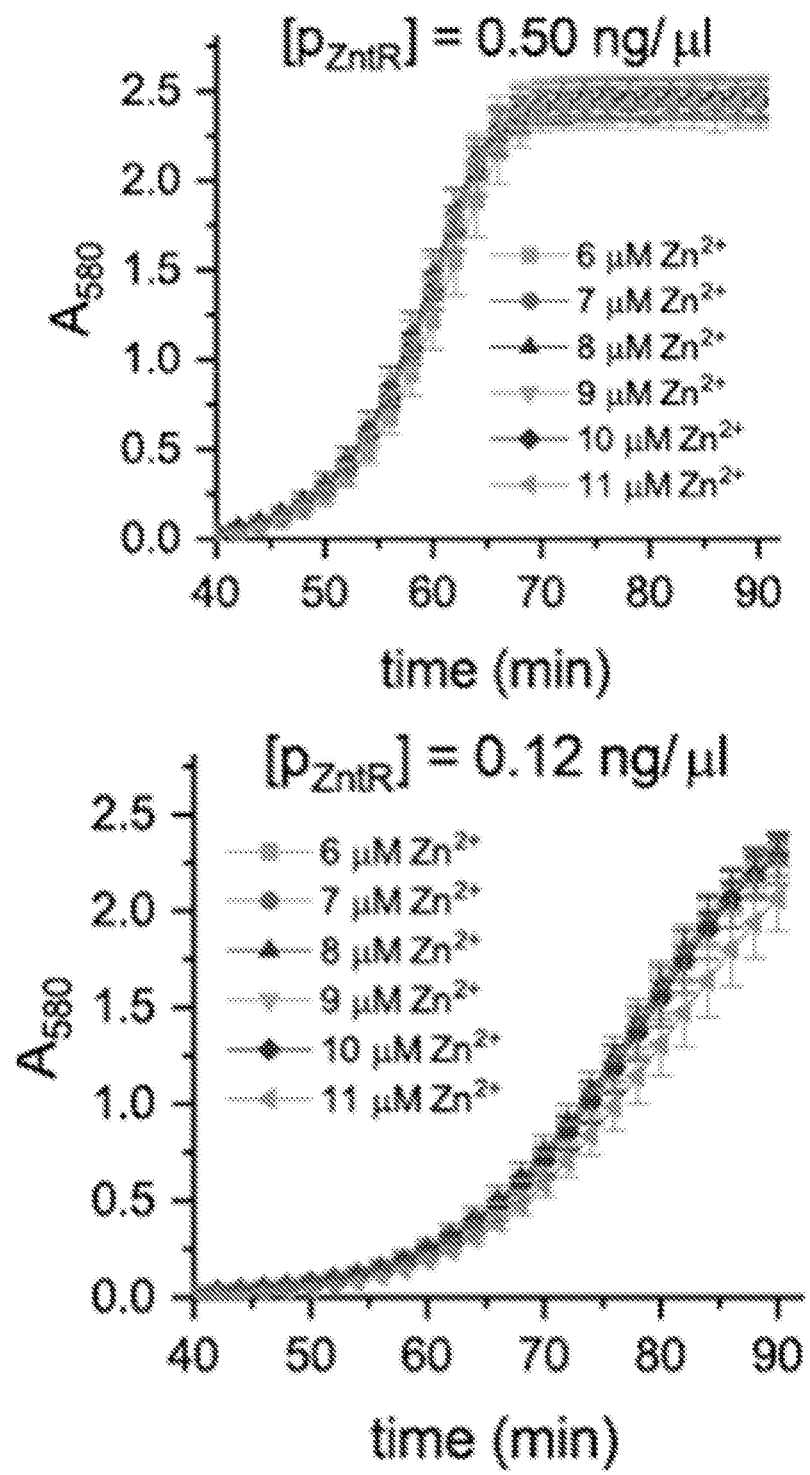
FIG. 10A-10E shows the validation of zinc quantification without added serum. (10A) In reactions without serum, the zinc response saturates. In all tests, colorimetric output was the same across the range of 7 to 11 µM zinc. This enabled the test to differentiate raw zinc concentrations between 0 and 4 µM. (10B) Selected time course readings of test and standard reactions run without serum. A large array of standard reactions with 8 µM zinc and a range of regulator concentrations was run in parallel with test reactions that had set regulator concentration and a range of zinc concentrations. For each concentration of zinc tested, a standard reaction showed nearly identical colorimetric output to a test reaction. (10C) Relationship between zinc concentration in the test reaction and the ZntR concentration in the standard reaction that most closely matched the test reaction. Correlations were consistent across experiments run on different days and in different batches of cell extract. The inventors determined the optimal set of regulator concentrations to correspond to each zinc concentration by choosing the regulator concentration closest to the average regulator concentration across three runs. (10D) Quantification of zinc concentrations in reactions without added serum for all four test runs, at 70 minutes. Runs 1-3 were used in initial calibration, and Run 4 was only used in test validation. Symbols falling inside the horizontal bars that correspond with the binned prediction ranges for each y-axis level indicated accurate predictions. (10E) Quantification error metrics for tests run without serum. In all runs, the QEM of the main diagonals was far below the threshold, and the QEM of the off diagonals was above the threshold between 70 and 90 minutes. Notably, tests were evaluated for detection of differences of 0.5 µM.
Figure 10A:
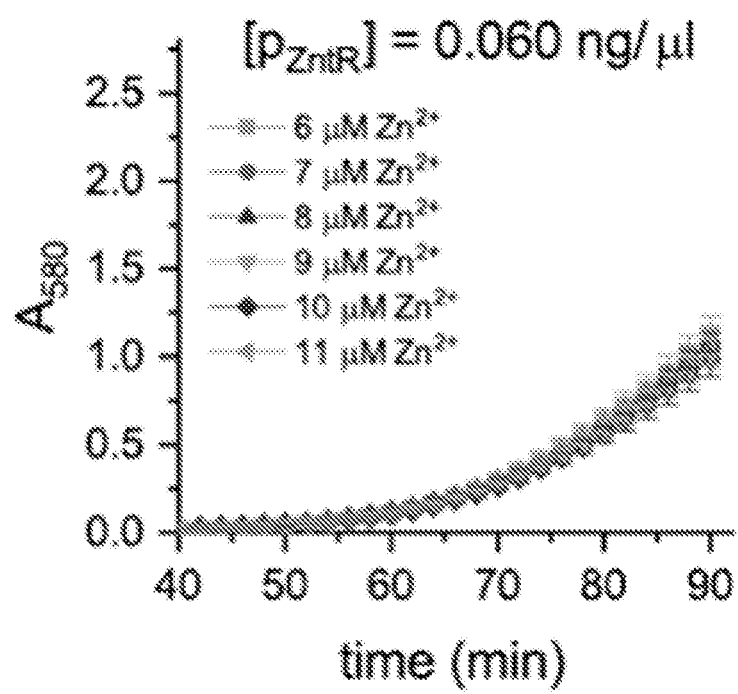
Figure 10B:
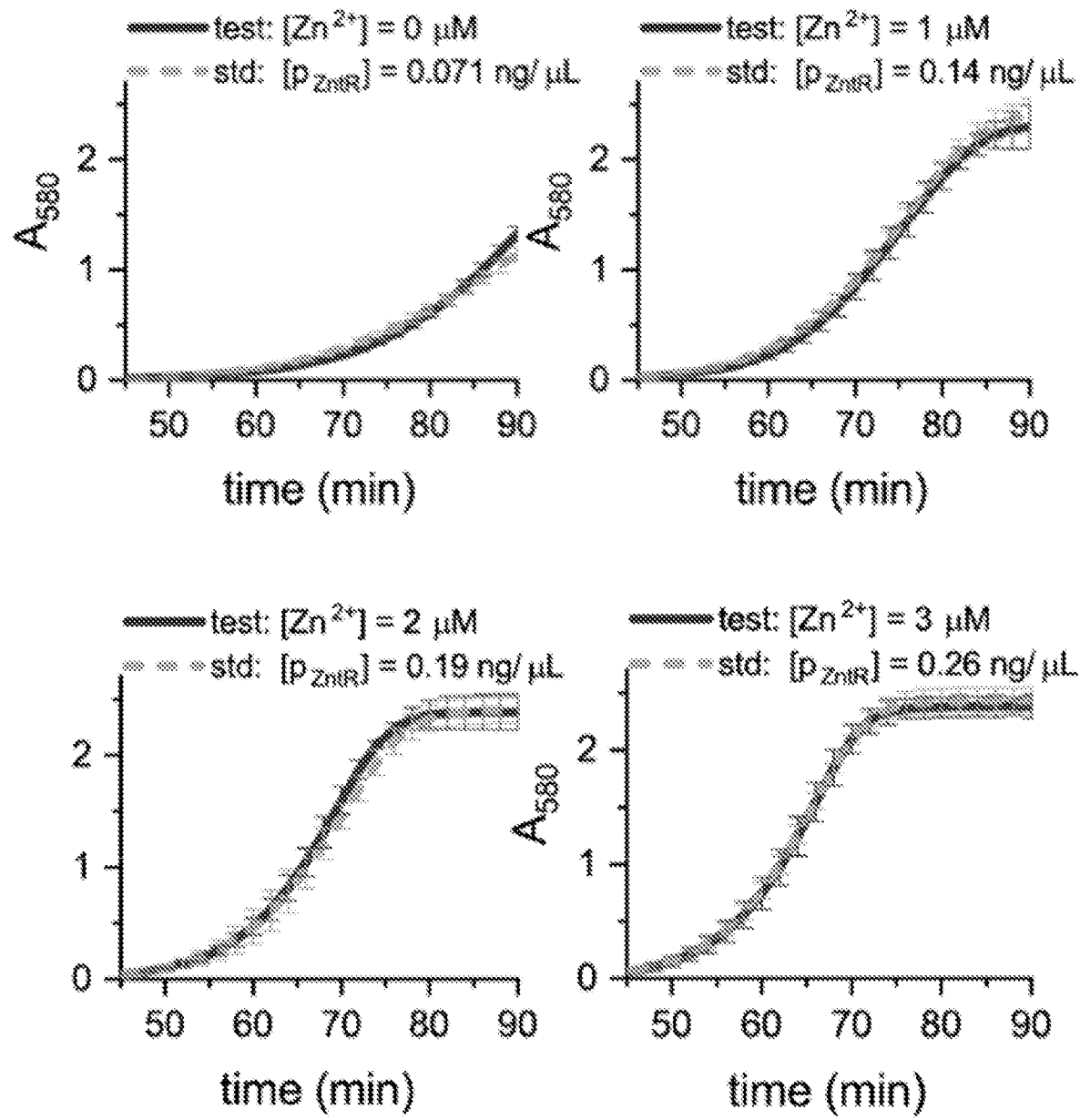
Figure 10C:
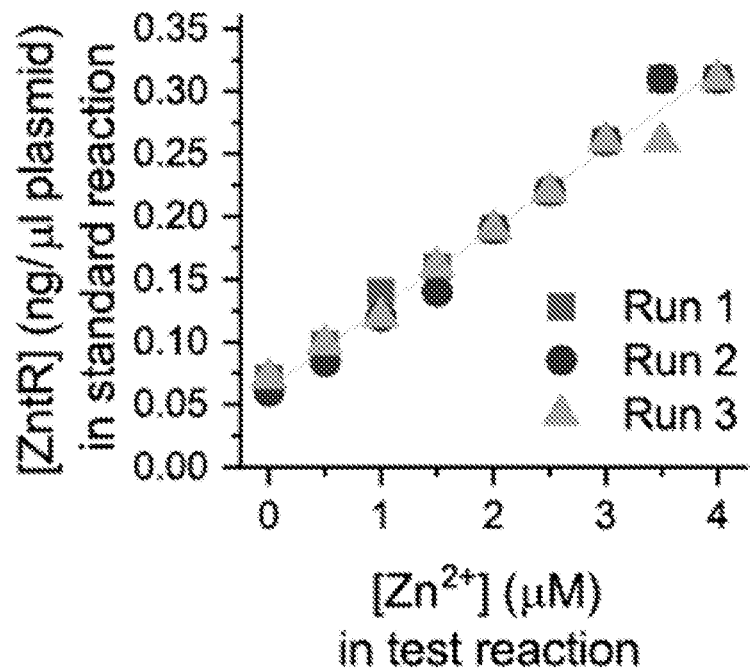
Figure 10D:
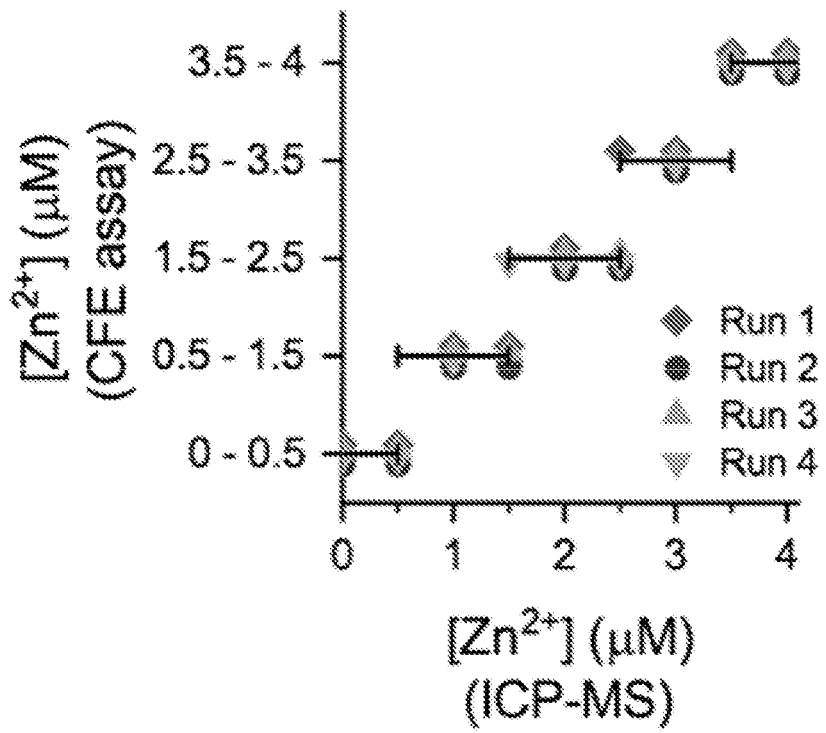
Figure 10E:
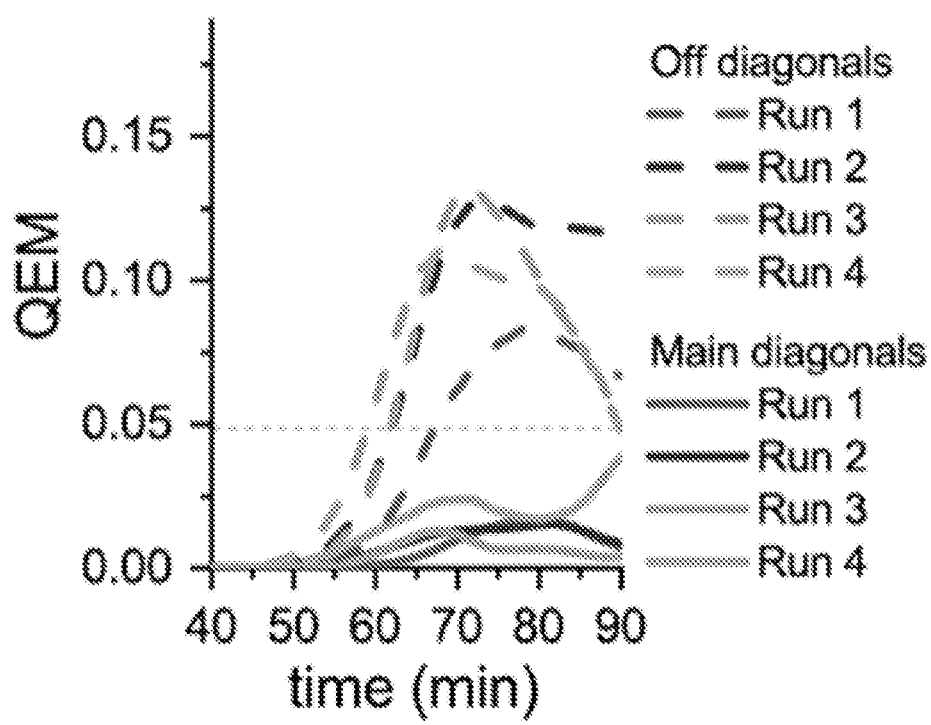
Figure 11:
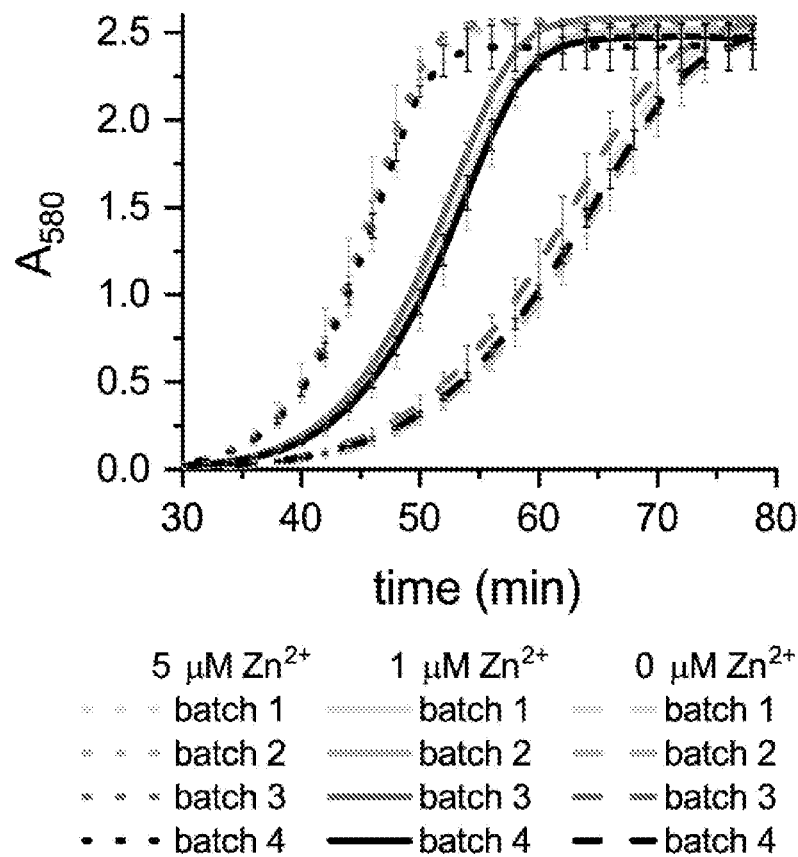
FIG. 11 shows the validation of direct protein addition to modulate zinc response. ZntR was expressed in 4 different batches, on different days and in different batches of cellular extract. A small amount of the completed reaction with overexpressed ZntR was added to a fresh reaction (comprising 1% of the fresh reaction volume). Each batch of ZntR mediated a nearly identical response to different concentrations of zinc.
Figure 12A:
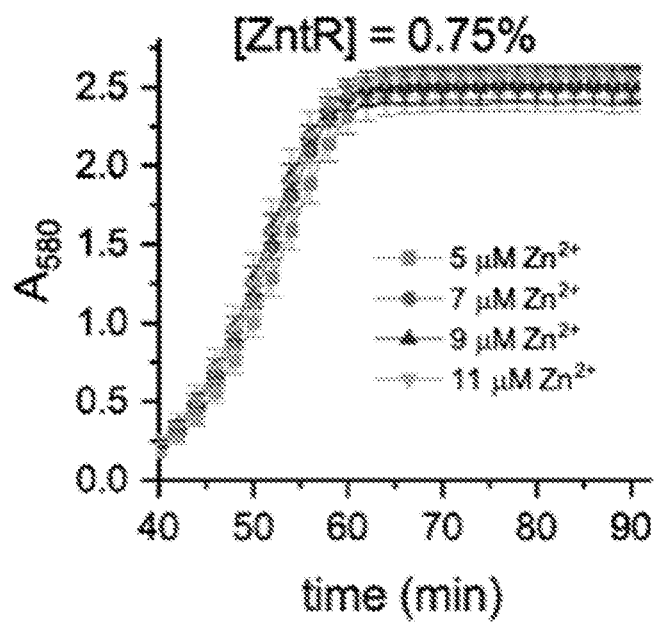
FIG. 12A-12E show the validation of zinc quantification with direct protein addition. (12A) When ZntR protein was added directly to the reaction, the zinc response saturates. In all tests, colorimetric output was the same across the range of 7 to 11 µM zinc. This enabled the test to differentiate raw zinc concentrations between 0 and 4 µM. (12B) Selected time course readings of test and standard reactions run with direct protein addition. A large array of standard reactions with 8 µM zinc and a range of regulator concentrations was run in parallel with test reactions that had set regulator concentration and a range of zinc concentrations. For each concentration of zinc tested, a standard reaction showed nearly identical colorimetric output to a test reaction. (12C) Relationship between zinc concentration in the test reaction and the ZntR concentration in the standard reaction that most closely matched the test reaction for tests run with direct protein addition. Correlations were consistent across experiments run on different days and in different batches of cell extract. The inventors determined the optimal set of regulator concentrations to correspond to each zinc concentration by choosing the regulator concentration closest to the average regulator concentration across three runs. (12D) Quantification of zinc concentrations in reactions with direct protein addition for all four test runs, at 70 minutes. Symbols falling inside the horizontal bars that correspond with the binned prediction ranges for each y-axis level indicated accurate predictions. (12E) Quantification error metrics for tests run with direct protein addition. In all runs, the QEM of the main diagonals was far below the threshold, and the QEM of the off diagonals was above the threshold between 70 and 90 minutes. Notably, tests were evaluated for detection of differences of 0.5 µM.
Figure 12A:
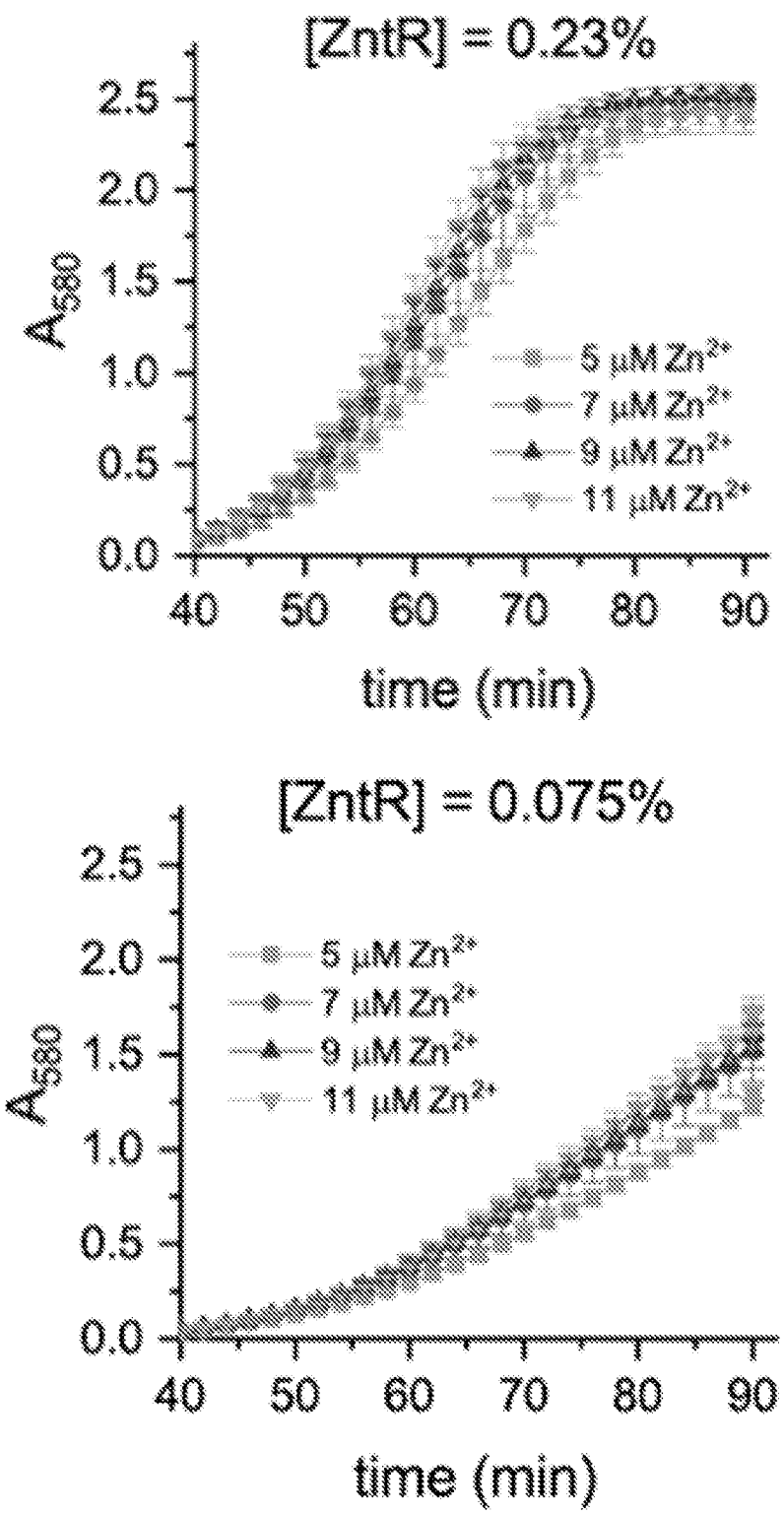
Figure 12B:
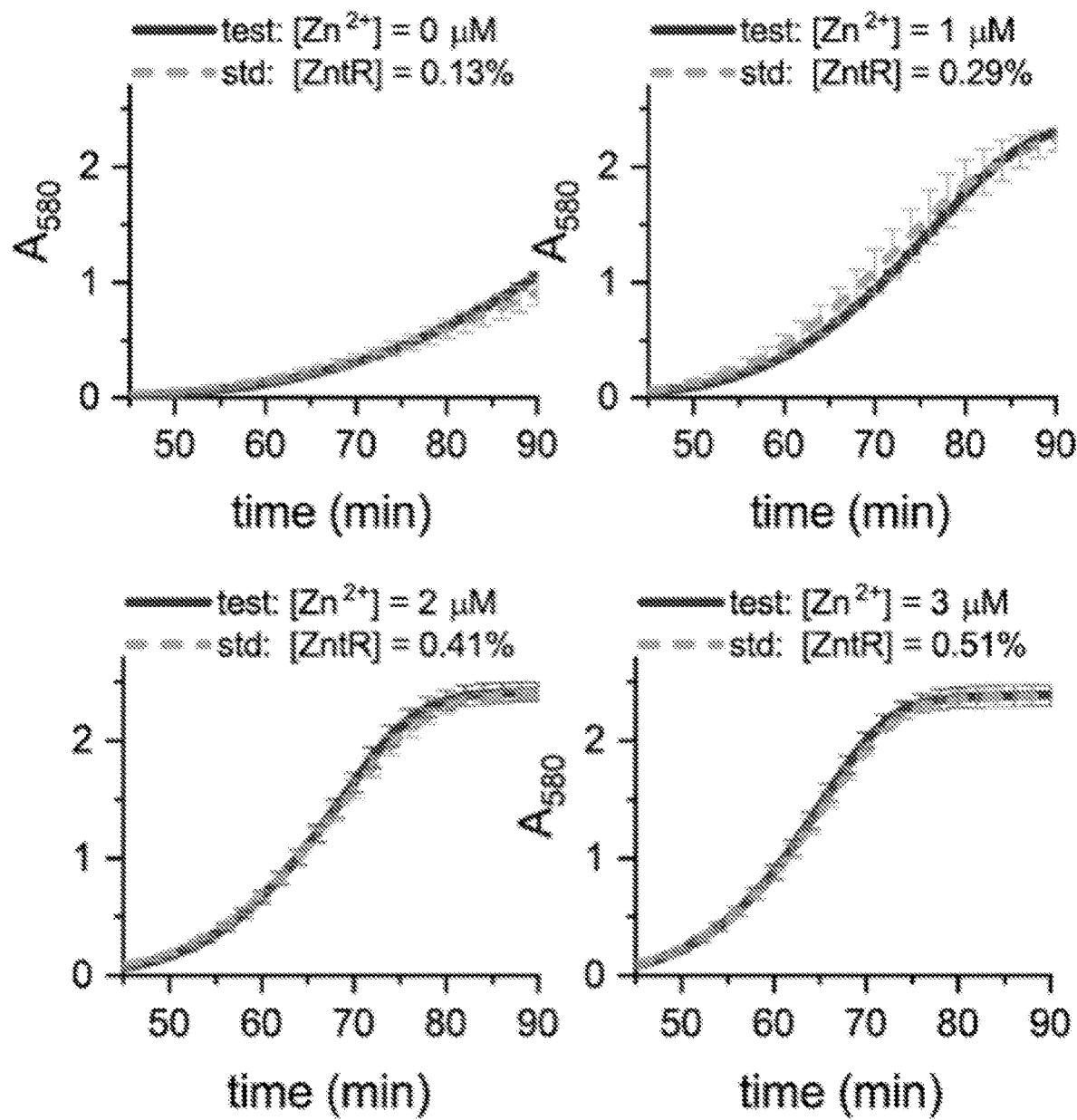
Figure 12C:
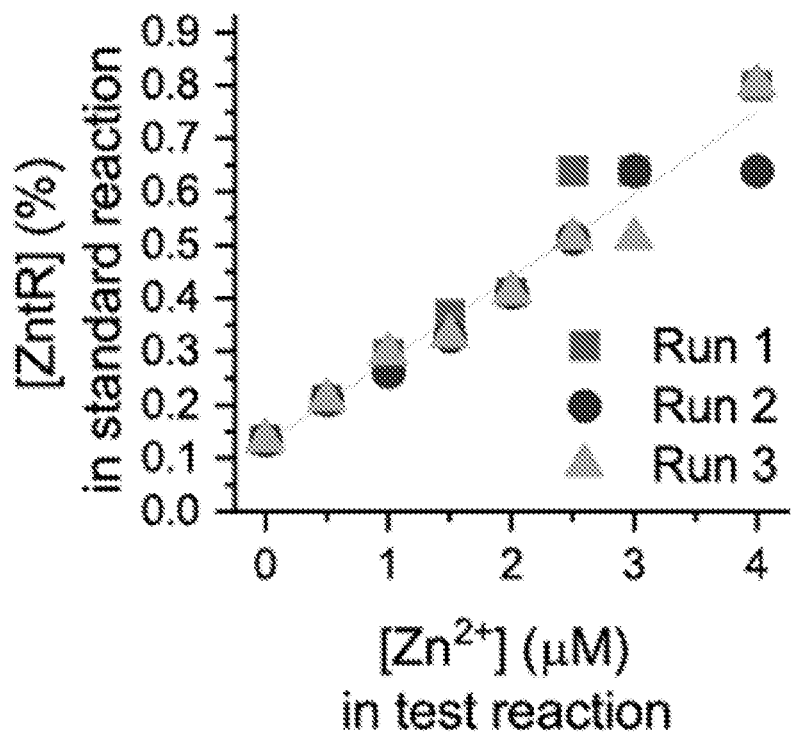
Figure 12D:
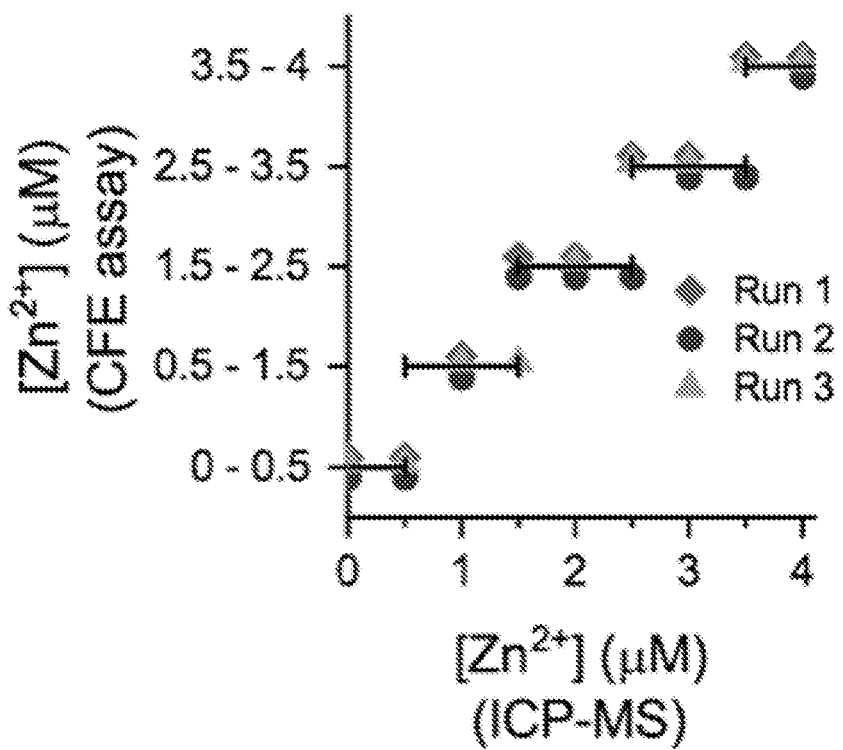
Figure 12E:
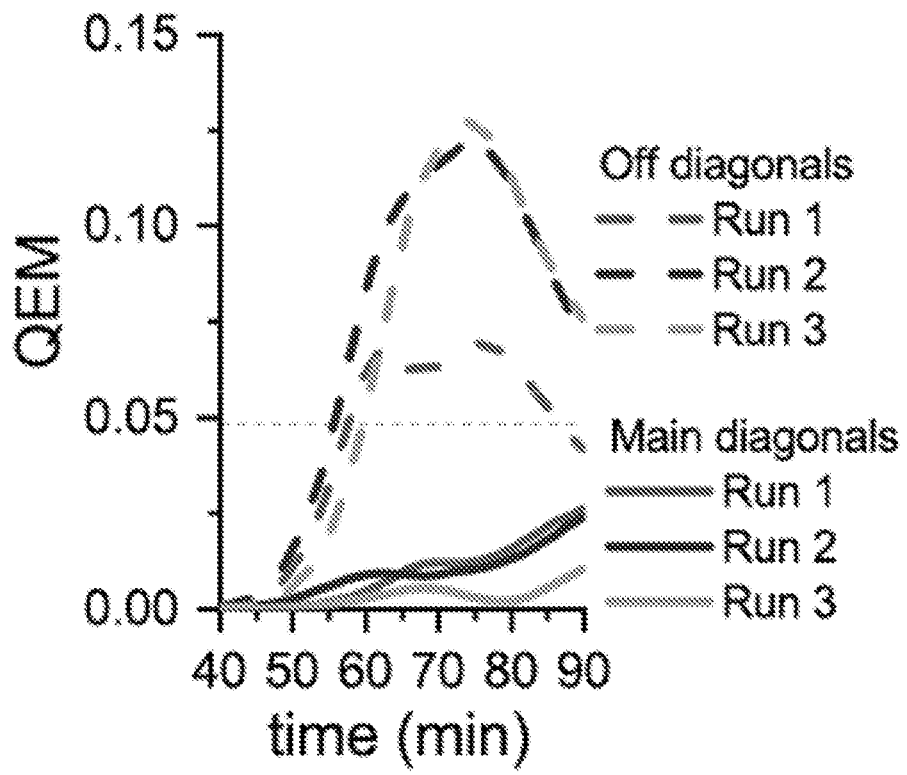

To determine what concentrations of the regulator plasmid pZntR to use in predictive standards, the inventors ran a large set of standard reactions (with saturated zinc and varied pZntR concentrations) and hypothetical test reactions (with a set pZntR concentration and varied zinc) in pooled serum that was collected from three individual donors. For each concentration of zinc in the hypothetical test reactions, the inventors identified a standard reaction with nearly identical colorimetric output (FIG. 1F). The relationship between regulator and zinc concentrations was consistent across experiments run on different days and in different batches of cell extract (FIG. 9). From these runs, the inventors determined the optimal regulator plasmid concentration to put in each reference reaction to create standards that correspond with different potential test results.

Accurate Biomarker Quantification in Serum

Figure 2A:
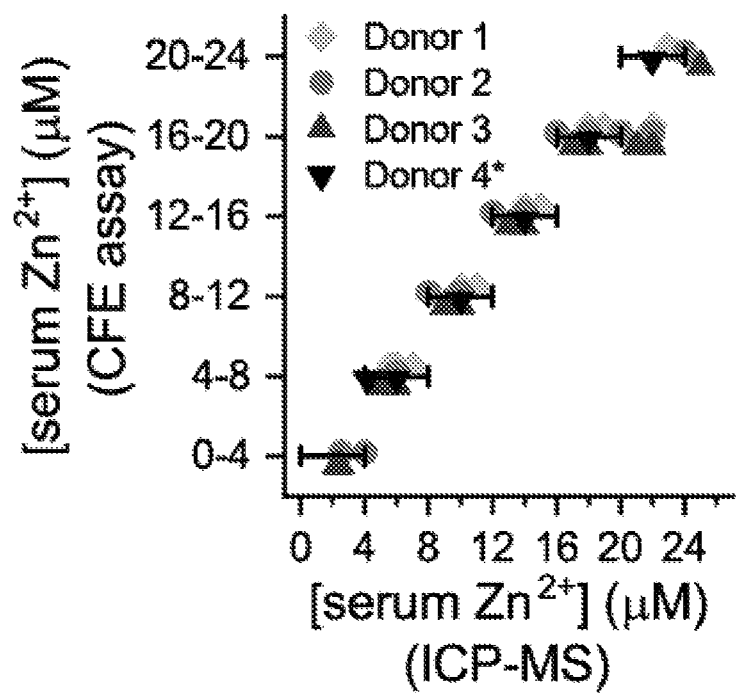
FIG. 2A-2C show that the described quantification approach provides high prediction accuracy at micromolar resolution of raw sample concentrations. (2A) Quantification of serum zinc concentrations for all four single-donor samples tested, evaluated at 56 minutes. Zinc concentration in chelex-treated samples was measured on an ICP-MS, and defined zinc standards were added to each sample to achieve a range of concentrations. Serum from Donors 1-3 was used in initial calibration, and serum from Donor 4 was only used in test validation, indicated by the asterisk. Symbols falling inside the horizontal bars that correspond with the binned prediction ranges for each y-axis level indicate that the CFE test accurately quantified zinc in the serum sample. (2B) Error quantification of all individual donor samples via the Quantification Error Metric (QEM). Low QEM for correct predictions and high QEM for incorrect predictions indicates unambiguously interpretable test results for a given time. (2C) Error quantification in non-ideal reaction conditions with serum from Donor 4.

The inventors next used these optimal regulator plasmid concentrations to quantify zinc in single-donor serum samples. Different concentrations of zinc were spiked into individual (zinc-depleted) serum samples, and each of these serum samples was then added to (1) a test reaction containing a defined concentration of the pZntR plasmid with no added zinc and (2) a set of standard reference reactions containing saturated zinc with the predetermined pZntR concentrations. Evaluation at a single time point within the one hour target time frame (56 minutes) showed accurate test results: the colorimetric output of each test reaction matched the appropriate reference reaction for all samples tested (including serum excluded from the pooled sample used for test calibration). The test accurately classified all serum zinc concentrations below 20 μM into concentration bins with a width of 4 μM (FIG. 2A). Though the test inaccurately classified some of the zinc concentrations above 20 μM (far above the deficiency threshold), the range of accurate predictions covered all clinically relevant serum zinc concentrations.

Figure 2B:
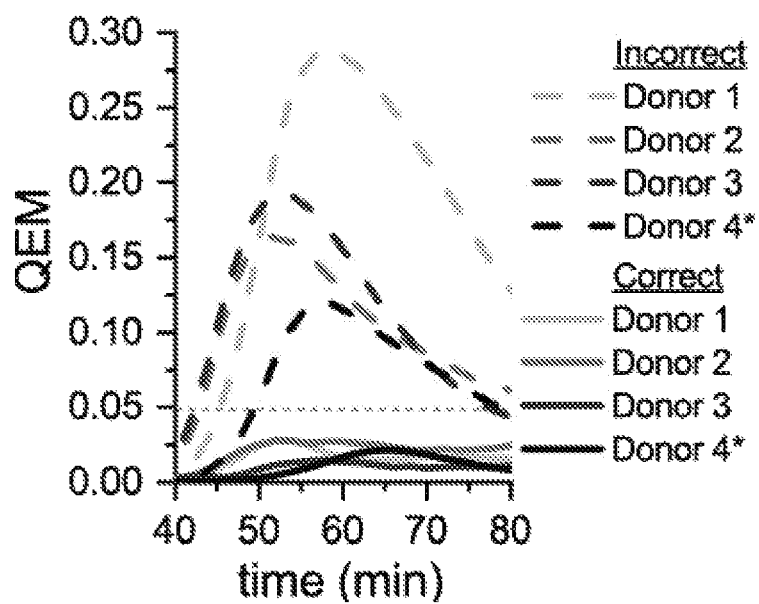

To quantitatively assess test prediction accuracy and specificity at all time points, the inventors defined a quantification error metric (QEM) that captured the differences in absorbance, across all zinc levels, between test reactions and predictive standards (Supplementary Text). Ideally, the QEM of the correct predictions should be zero, and the QEM of the incorrect predictions should be high. The inventors set a QEM threshold that corresponds with the ability to differentiate between one-tenth increments of the color spectrum (FIG. 1C). In all serum samples, the QEM of the correct predictions was substantially lower than the set threshold, and the QEM of the closest incorrect predictions was substantially higher than the threshold (FIG. 2B), indicating unambiguous interpretability of test results.

Figure 2C:
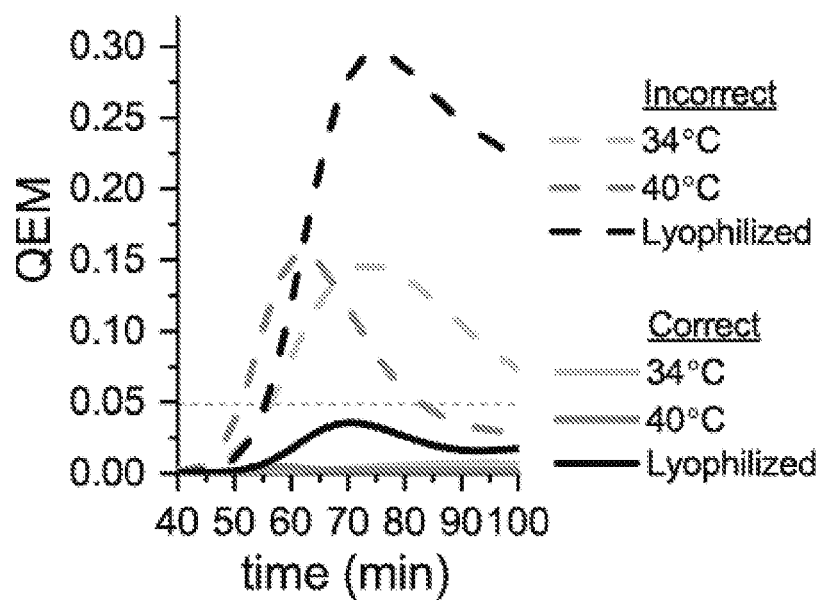

The parallelized calibration approach was robust to both assay conditions and multiple assay design parameters. Though optimal standards were chosen by correlations determined in freshly assembled reactions run at 37° C., the test accurately quantified zinc when run at both 34° C. and 40° C. and following lyophilization (FIG. 2C). Moreover, the method can reliably quantify zinc in samples without serum (FIG. 10A-10E) and in assay designs where the transcriptional regulator is added to the reaction rather than being expressed during the reaction (FIGS. 11, 12A-12E).

Figure 13:
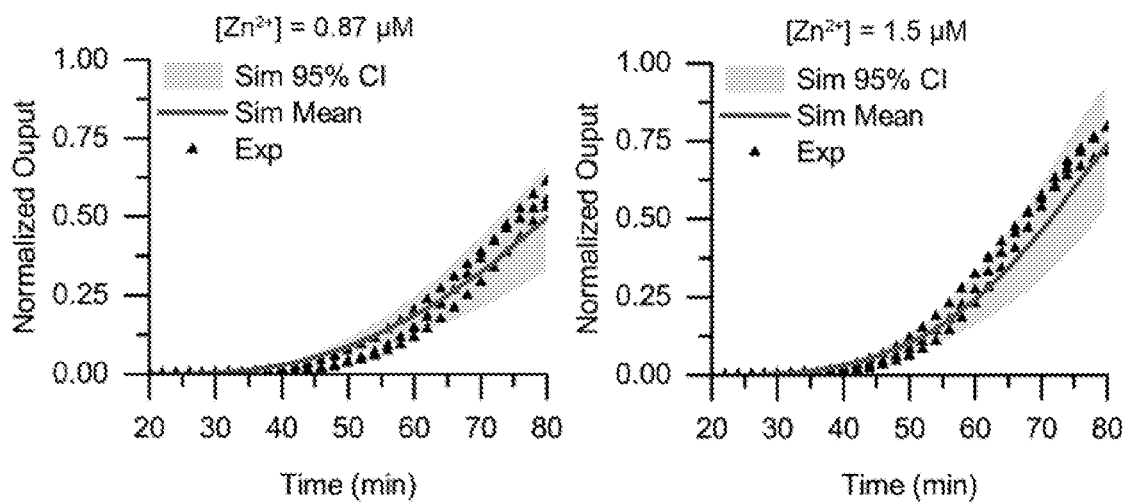
FIG. 13 shows a comparison of parameterized model and experimental data in the zinc-response circuit. Experimental and model trajectories were normalized by the maximum theoretical CPR concentration (1000 µM). The mean simulated trajectories (dark gray line) are shown within the 95% confidence interval (light gray region) from the range of simulated trajectories; they closely predict experimental data (black triangles).
Figure 13:
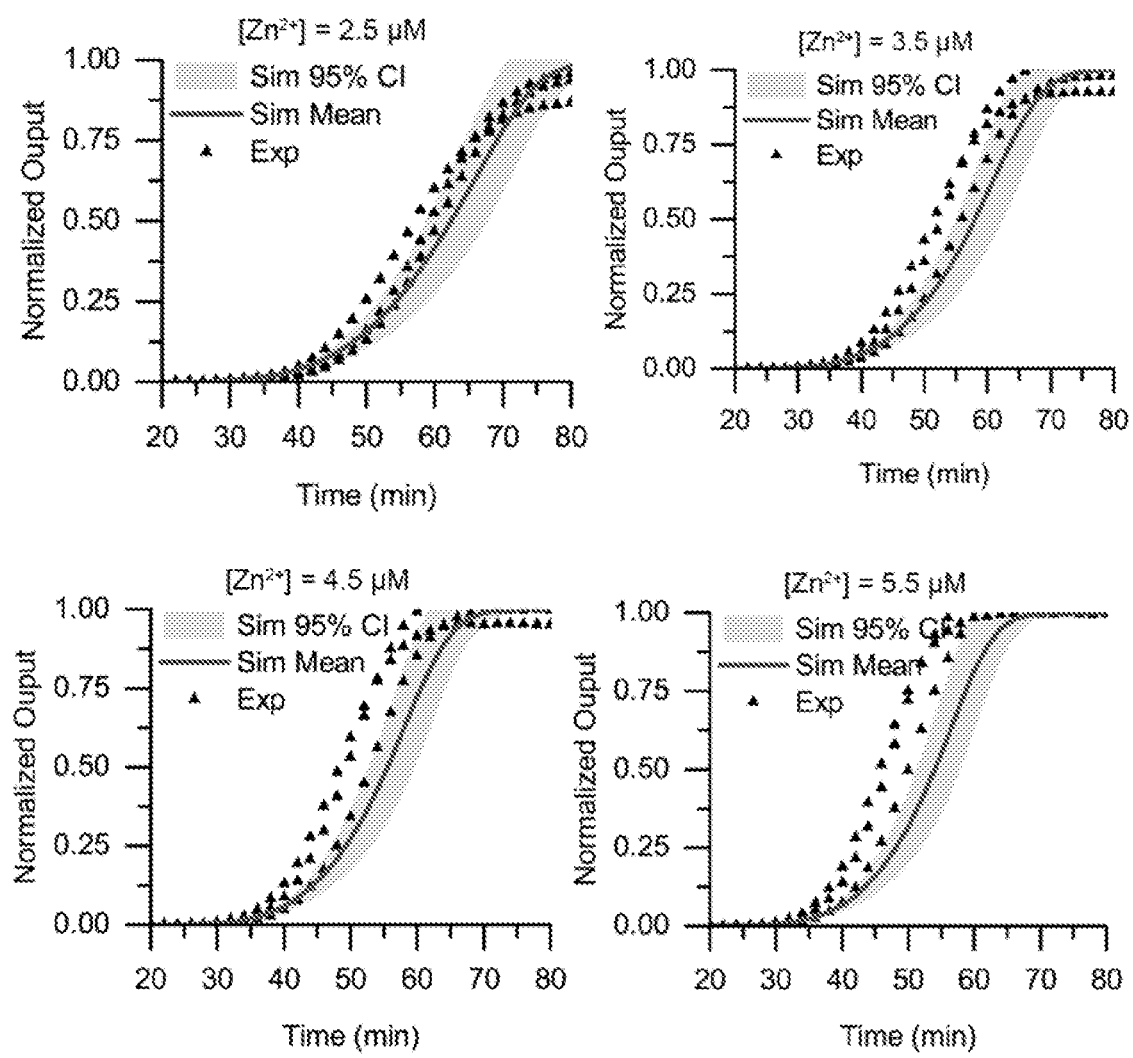
Figure 14A:
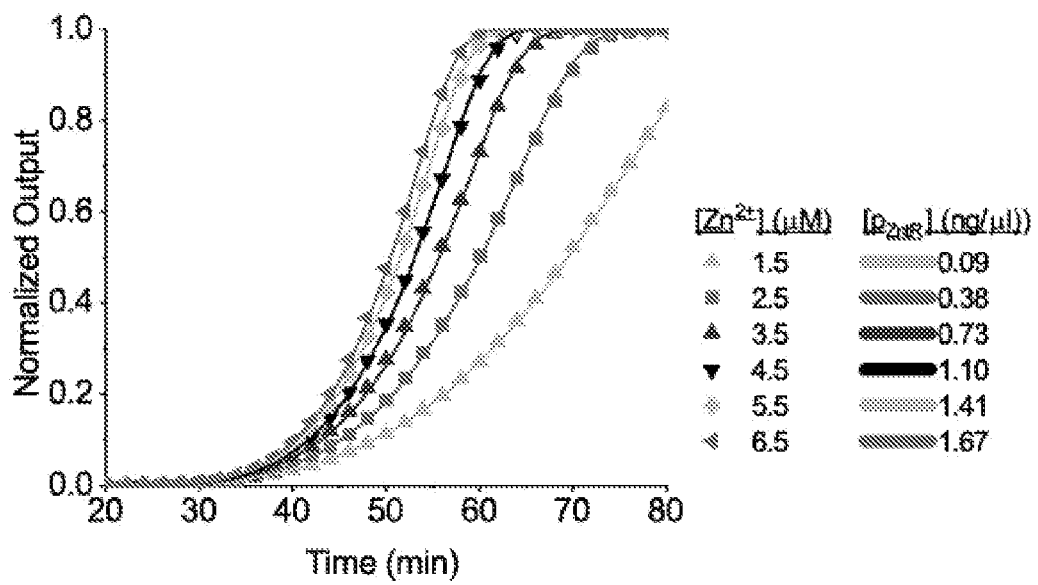
FIG. 14A-14C shows simulated zinc and regulator mapping. (14A) The pZntR concentrations for standard reactions necessary to in silico recapitulate the in silico simulated circuit responses to six zinc concentrations were calculated. For all standard reactions, the zinc levels were set to a saturating level and only the transcription rate of ZntR, $\beta\_1$, was estimated to match simulated test reactions. The estimated values of $\beta\_1$ were then mapped back to plasmid concentrations. (14B) The inventors' model was able to qualitatively recapitulate the linear relationship at low zinc concentrations in test reactions and the order of magnitude of the plasmid concentrations needed. However, perhaps due to the limitations of the model's assumptions, there may be systematic bias in the absolute quantitative values of simulated ZntR plasmid concentrations (FIG. 9). (14C) Normalized QEM over time.
Figure 14B:
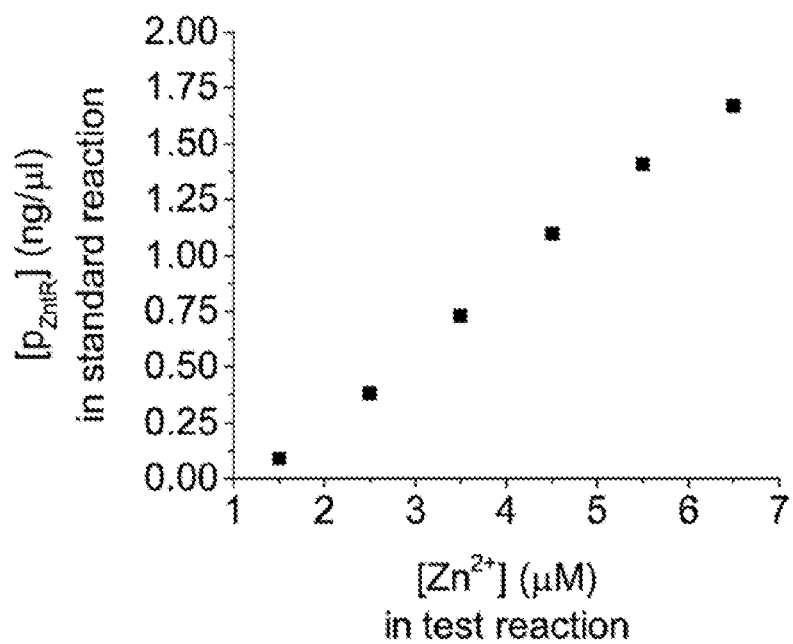
Figure 14C:
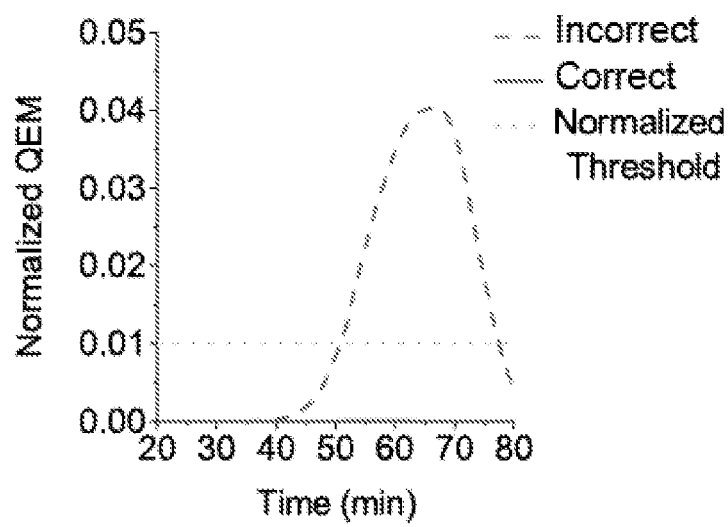
Figure 15:
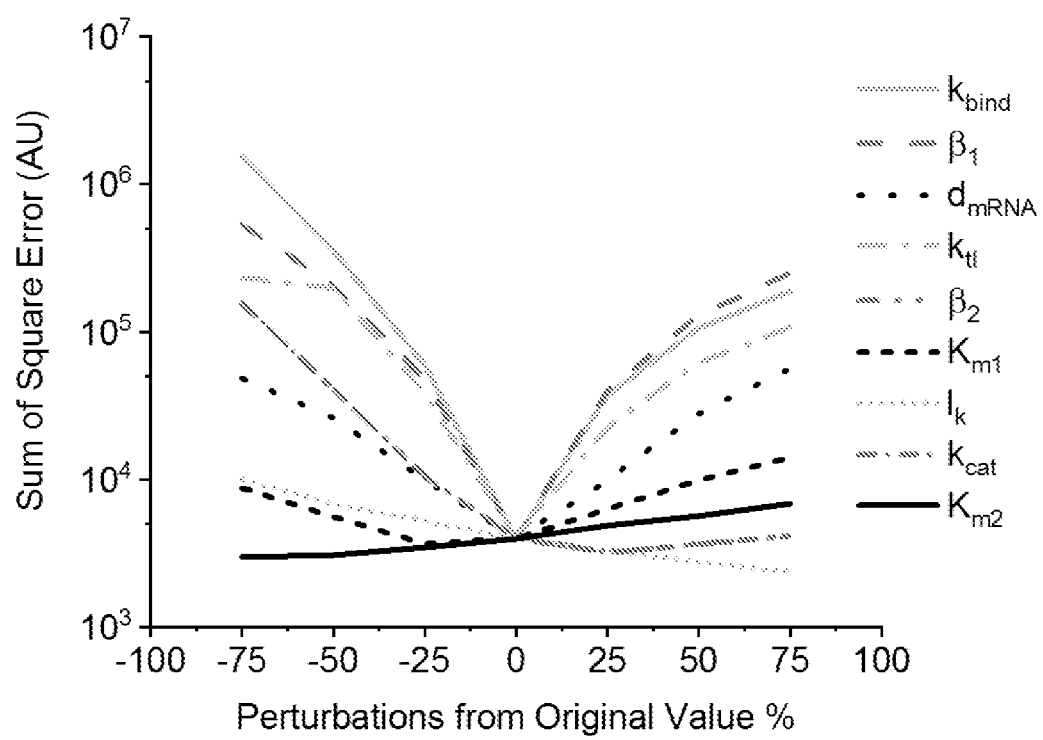
FIG. 15 shows the perturbation of parameter values to identify the most sensitive parameters in the zinc model. To determine which estimated parameters are the most sensitive, the inventors perturbed each parameter up to ±75% of its optimized value and calculated the sum of squared errors between the simulated test and standard reactions. The inventors found the binding rate constant of zinc to ZntR ($k_{bind}$) to be the most sensitive throughout the range of zinc levels tested. Other sensitive parameters include the transcriptional rate of ZntR ($\beta_1$), degradation rate of mRNA ($d_{mRNA}$), translation rate of protein ($k_{tl}$) and the cleavage rate of CPRG to CPR ($k_{cat}$).

To further characterize the standardization approach, the inventors created an ordinary differential equation model that qualitatively recapitulates some experimental results. Based on previously published approaches, sensitivity analysis was used to guide an iterative parameter fitting method that minimized the error between computational predictions and data collected from reactions run in 25% serum with a range of zinc concentrations (FIG. 13); this approach provided improved parameter estimates compared to simultaneous optimization of all parameter values against all experimental data. When using these optimal parameter estimates, the model qualitatively reproduced the trend in the relationship between low zinc concentrations in the test reactions and regulator concentrations in the standard reactions (FIG. 14A-14C). The predicted regulatory concentrations were usually within a factor of two of the experimentally observed results (FIG. 9), though there were differences in the exact quantitative values due to the limitations of the model's assumptions (including binding kinetics and parameter lumping). Of the identified relevant parameters, the predictive ability of the test is most sensitive to changes in the binding constant of zinc to ZntR, transcriptional rate of ZntR, degradation rate of RNA, the translational rate of proteins, and the cleavage rate of CPRG to CPR (FIG. 15).

Equipment-Free Test Interpretation in Serum

Figure 3A:
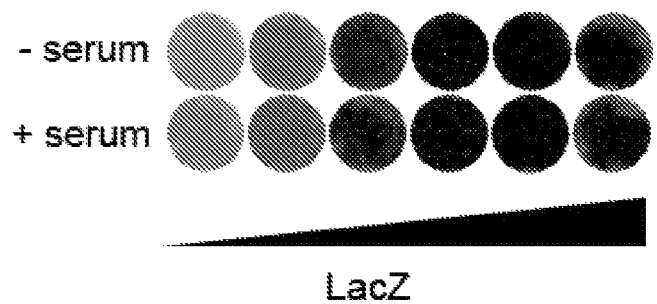
FIG. 3A-3B shows that addition of small molecules reverses color shifts due to serum albumin. (3A) Reactions run in serum appeared different from reactions run in the absence of serum. Reactions with complete conversion of CPRG to CPR appear more purple in a 25% serum matrix. More importantly, in 25% serum the colored orange and red reaction intermediates initially observed were no longer visible. (3B) While the presence of serum shifts the absorbance peak of CPR approximately 10 nm, the addition of small molecules that bind albumin reversed this spectrum shift.
Figure 16:
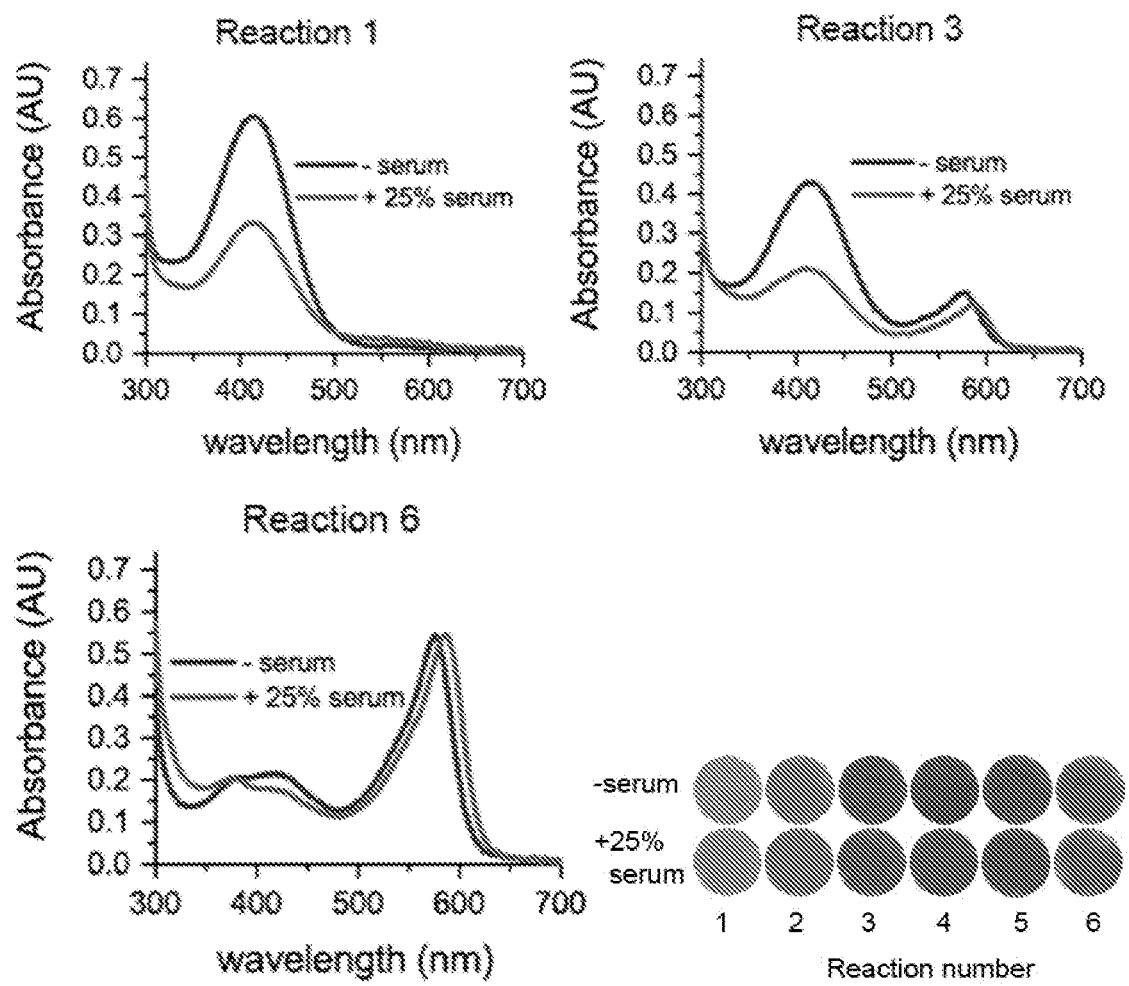
FIG. 16 shows that the color change caused by serum corresponded with a shift in the visible spectrum of chlorophenol red. The image in FIG. 3A was reproduced with reaction numbers added for identification of spectra. The absorption spectra from certain reactions are shown. In both water and serum, only two peaks were visible for different reaction stages. The peak at 400 nm decreases as the reaction proceeded, and the peak near 580 nm grew. There was a shift in the peak near 580 nm of about 10 nm when reactions were run in serum.

Ideally, for an equipment-free test, users could easily match the color of the test reaction to the color of standard reference reactions, similarly to how one reads pH strips. The diverse array of colors that correspond with intermediate reaction stages (FIG. 1C) readily enabled such interpretation. However, when the test was run in serum, the distinct colored intermediates (orange and red) are eliminated, and all intermediate reactions states are varying degrees of yellow and purple (FIG. 3A and FIG. 16). While this has minimal effect when quantifying test output via absorbance, lack of distinct intermediates made quantitation by eye much more challenging.

Figure 3B:
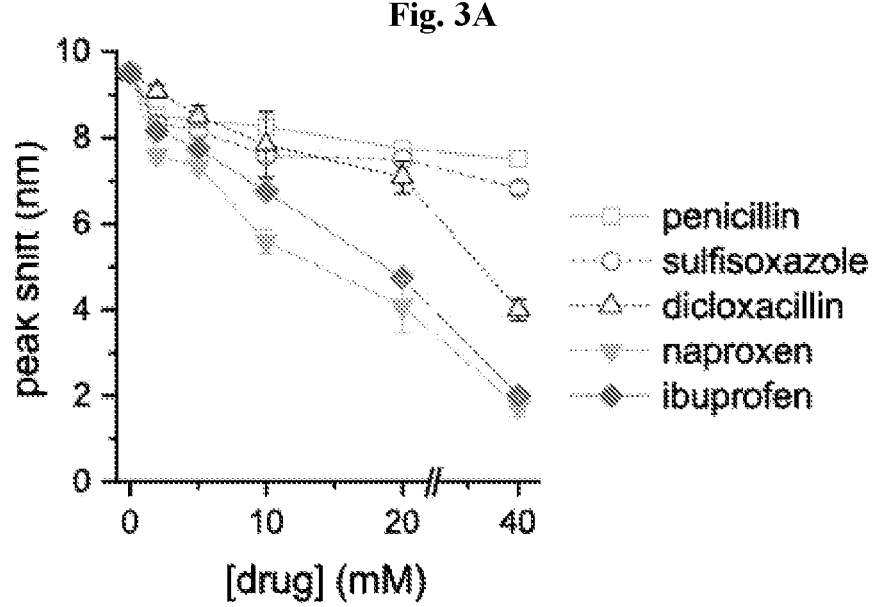

Elimination of colored intermediates corresponds with a 10 nm shift in the absorption spectrum of CPR (FIG. 16). Dyes with similar structures to CPR are known to change color upon interaction with serum albumin, and the inventors demonstrated that human serum albumin reproduces the color change seen in serum samples. To reverse this color change, the inventors added different compounds known to bind serum albumin, with the aim of displacing CPR from albumin. Naproxen addition elicited the most dramatic effects, nearly restoring reaction color to its appearance without added serum (FIG. 3B) and thus enabling equipment-free biomarker quantification (FIG. 16).

Discussion

Matrix-specific quantification is a critical step in enabling low-cost diagnostics with clinical impact. In this work, the inventors developed a versatile, cell-free diagnostic platform that allows for robust quantification of biomarker levels in different environmental conditions. The inventors specifically addressed the impacts of the sample matrix on accuracy and robustness of quantification by using the patient sample itself as the sample matrix for the parallel calibration standards. Further, this approach enabled test interpretation without any equipment by engineering an originally two-color readout to take advantage of the broad color spectrum that corresponds with different levels of β-galactosidase activity.

The specific zinc assay the inventors created is readily translatable to public health and clinical diagnostic applications. Of foremost importance, this test detects diagnostically relevant concentrations of serum zinc, the biomarker for a nutritional deficiency that kills 100,000 children under age five annually. Thresholds used for identifying zinc deficiency are typically no lower than 8.5 µM and no higher than 11.5 µM. This assay (in 25% serum) reliably distinguishes 4 µM increments between 0 and 20 µM serum zinc (FIG. 2A), which enabled identification of sufficient, borderline, and low serum zinc levels. This approach meets nearly all requirements for field-friendly testing in the developing world (where zinc deficiency is mostly found), as it requires no electricity or analytical equipment, minimal processing steps (just separation of red blood cells from serum, which can be accomplished with field-friendly approaches), and uses only a finger-stick volume of blood. Though zinc overdose is rare, the test could be slightly altered via incorporation of zinc chelators or addition of smaller serum volumes so that it could quantify serum zinc concentrations indicative of zinc overdose (>75 µM).

This matrix-specific quantification approach can be easily expanded to other biomarkers.

For example, the inventors showed that by simply replacing a transcription factor-based sensor with a toehold switch (a completely different information transduction mechanism), a minimal-equipment test that could quantify nucleic acids could be created. The platform described herein, therefore, is positioned to serve as an important foundation for cell-free biosensors, especially given the rise of efforts to use cell-free expression systems and purified in vitro platforms to quantify diverse types of analytes. Transcription factors that bind to a new target molecule can be seamlessly integrated into the developed framework, as could toehold switches for any nucleic acid sequence, or established riboswitches; this already gives a wide starting point for the number of quantitative diagnostics that could be created using this approach. Sensing systems such as aptamers and antibody fragments can be readily evolved to detect small molecules or proteins with user-defined sensitivity, potentially expanding the reach of this platform to essentially arbitrary biomarkers.

Though the inventors focused on equipment-free test interpretation, the matrix-specific quantification platform could also be incorporated into a minimal-equipment testing framework for automated, more precise quantification. A user could add a cartridge of lyophilized test and standard reactions for any desired biomarker to a low-cost absorbance reader and use serum from just a finger prick of blood to rehydrate and activate the tests. The reader would then report a more precise, matrix-normalized biomarker concentration.

These tests, whether interpreted visually or with equipment, could enable at-home health monitoring or could be used be used as rapid initial screens in clinics before ordering more expensive laboratory panels. Taken together, assays developed via the quantification platform described here could dramatically improve access to vital health information, potentially transforming health monitoring and analytics.

Example 2: Development of a Cell-Free Expression-Based Toehold Assay

In order to show generalizability of the method of reducing or eliminating inter-sample variability to other biomarkers besides small molecules, the inventors tested the method's ability to quantify a vastly different biomarker in cell-free expression systems, specifically RNA.
Materials and Methods
Preparation of Cellular Lysate Cellular lysate for toehold switch experiments was prepared. BL21 Star (DE3) ΔlacIZYA cells were grown in 2×YTP medium at 37° C. and 220 rpm to an OD of 2.0. Cells were centrifuged at 2700 rcf and washed three times with S30A buffer (50 mM of Tris, 14 mM magnesium glutamate, 60 mM potassium glutamate, 2 mM dithiothreitol, pH corrected to 7.7 with acetic acid). Wet cell mass was determined after the third centrifugation step, the cells were resuspended in 1 mL of S30A buffer per 1 g of wet cell mass and sonicated using the same method described above, though with a sonication output of approximately 400 J. Following the centrifugation of the sonicated cellular mixture, the supernatant was removed, divided into 0.5 mL aliquots, and incubated at 37° C. and 220 rpm for 80 minutes. After this runoff reaction, the cellular lysate was centrifuged at 12,000 rcf and 4° C. for 10 minutes. The supernatant was removed and loaded into a 10 kDa MWCO dialysis cassette (Thermo Fisher). Lysate was dialyzed in 1 L of S30B buffer (14 mM magnesium glutamate, 60 mM potassium glutamate, 1 mM dithiothreitol, pH-corrected to 8.2 with Tris) at 4° C. for 3 hours. Dialyzed lysate was removed and centrifuged at 12,000 rcf and 4° C. for 10 minutes. The supernatant was removed, aliquoted, flash frozen in liquid nitrogen, and stored at −80° C. for future use.
Cell-Free Reactions: Toehold Switches For experiments involving toehold switches, cell-free reactions were run according to established protocols. Each reaction contained 1.5 mM of ATP and GTP, 0.9 mM of CTP and UTP, 0.2 mg/mL E. coli tRNA mixture, 0.33 mM of NAD, 0.26 mM of CoA, 0.75 mM cyclic adenosine monophosphate (cAMP), 0.068 mM of folinic acid, 1 mM of spermidine, 30 mM of 3-phosphoglyceric acid (3-PGA), 50 mM of HEPES, 1.5 mM each of the 20 standard amino acids, 4 mM of magnesium glutamate, 100 mM of potassium glutamate, 2% PEG-8000, 33% cell extract, 0.6 mg/mL CPRG, and DNA expression plasmids. Toehold switch was expressed from the plasmid pSwitch. Unless otherwise specified, the concentration of pSwitch in reactions was 2.5 nM. Trigger RNA was produced from 40 ng/μL linear DNA template in an in vitro transcription reaction using T7 RNA Polymerase (NEB), following the manufacturer's protocol. Synthesized RNA was treated with DNase to remove the DNA template and then purified using a Zymo RNA Clean and Concentrator kit (R1014), according to the manufacturer's protocol. Time course reactions were run as described above.
Determination of Best-Fit Reactions and Predictive Standard Reactions In determining which standard reference reaction best fit each zinc concentration, sum of squared error (SSE) minimization was used. The difference between each standard and test reaction was calculated at all time points between 30 and 90 minutes. The SSE was calculated over this time frame, and the standard reaction that had the lowest SSE was determined to be the best-fit reaction and thus the optimal regulator for that experimental run. When choosing what regulator concentration best predicts each potential biomarker concentration, we determined the overall optimal regulator concentration as the one closest to the average of the optimal matching regulator concentration across three runs.
Spectra Analysis To analyze the spectrum of chlorophenol red and reaction intermediates, a large batch of concentrated chlorophenol red was made by adding CPRG to a small amount of extract made from standard BL21(DE3) cells (which have high baseline β-galactosidase activity). The spectrum of CPR was analyzed to ensure that all CPRG reacted to CPR by screening for absence of a detectable peak at 410 nm. Different combinations of CPRG and CPR were then added to solutions containing 27% bacterial cell extract (made from BL21(DE3) ΔlacIZYA cells), with or without serum. The final concentration of dye in each solution analyzed was 1.02 μM, which corresponds with addition of 0.6 mg/ml of CPRG.

When adding small molecules to the reaction, 10× stocks of each molecule were made. Penicillin, dicloxacillin, and naproxen were dissolved in water, ibuprofen was dissolved in ethanol, and sulfisoxazole was dissolved in chloroform. 3 μL of each stock was added to PCR tubes, and tubes were left open in a fume hood overnight so that solvents could evaporate. A 30 μL solution containing the specified amount of dye, protein extract, and serum was used to re-dissolve the small molecule. Concentrations reported are the final concentration of small molecule in the analyzed solutions.

Figure 4A:
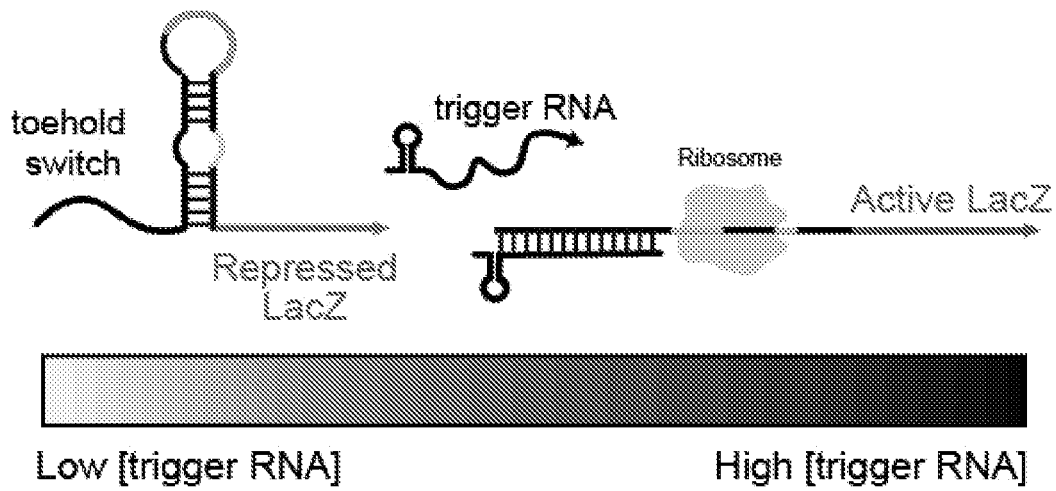
FIG. 4A-4D shows that the quantification approach described herein is generalizable to toehold switches. (4A) Schematic of toehold switch used to control β-galactosidase production. Trigger RNA unfolds the toehold switch and enables β-galactosidase translation. Increasing amounts of trigger RNA correspond with increased β-galactosidase translation. (4B) Test quantification of trigger concentrations, evaluated at 40 minutes. Purified RNA was added to each sample at different, known concentrations. Symbols falling inside the horizontal bars that correspond with the binned prediction ranges for each y-axis level indicate that the cell-free expression test accurately quantified RNA in the sample. (4C) Quantification error for toehold sensing. (4D) Visualization of test and standard reactions, evaluated at 40 minutes. The color of test reactions matches the color of the appropriate standard reference reaction.
Figure 17:
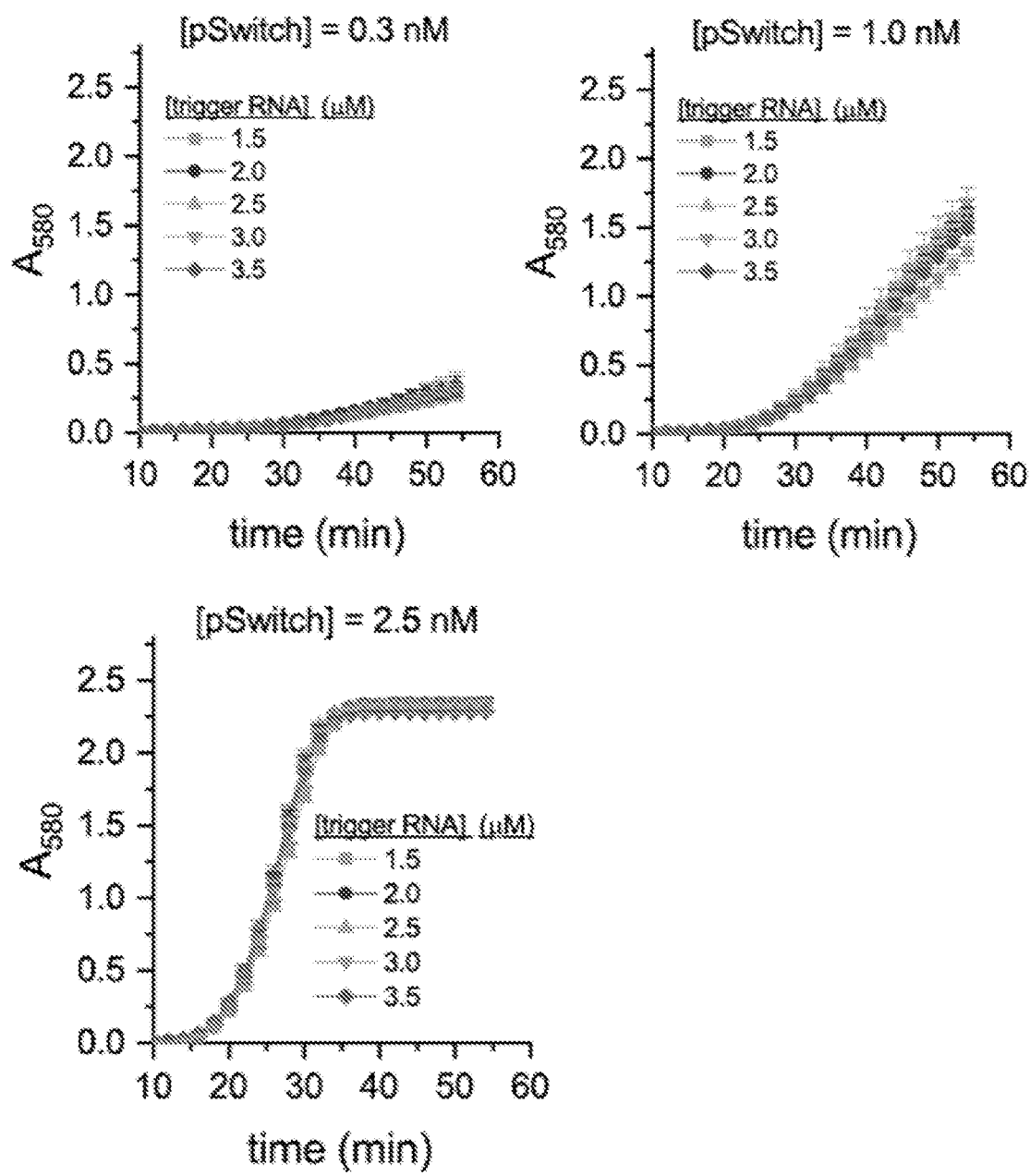
FIG. 17 shows the response to trigger RNA addition saturates. Colorimetric response from toehold switch was identical across a range of trigger RNA concentrations. Reactions with different switch concentrations were run in a range of trigger RNA concentrations. In all tests run, colorimetric output was the same across the range of 2 to 3.5 µM trigger plasmid. This enabled the test to differentiate trigger concentrations between 0 and 1.5 µM.
Figure 18:
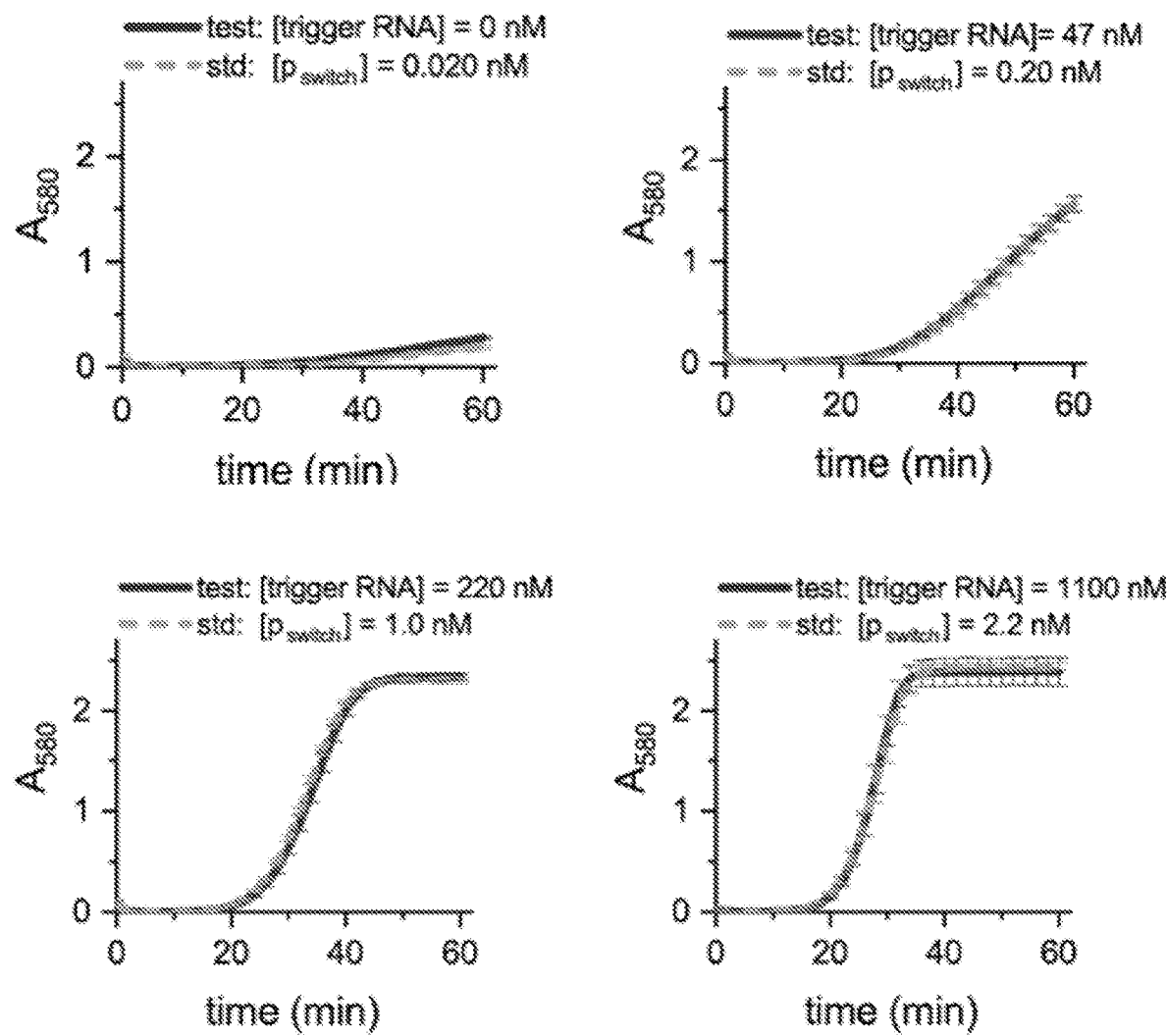
FIG. 18 shows selected time-course readings of test and standard reactions for a toehold sensor. A large array of standard reactions with saturated trigger RNA concentrations and a range of switch concentrations was run in parallel with test reactions that had set switch concentration and a range of trigger concentrations. For each concentration of trigger tested, a standard reaction showed nearly identical colorimetric output.
Figure 19:
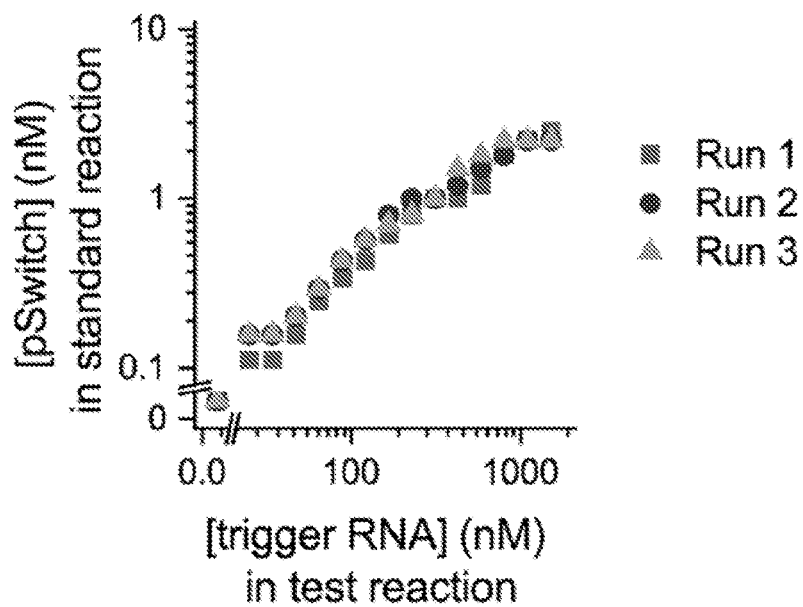
FIG. 19 shows the relationship between trigger concentration in the test reaction and the switch concentration in the calibration reaction. Correlations were consistent across all experiments. The inventors chose the optimal regulator concentration to correspond with each potential test result as the one closest to the average of the optimal matching regulator concentration across three runs.

The spectra of all solutions reported were measured in triplicate with a Nanodrop 2000. When analyzing reaction intermediates, spectrum height was normalized to a peak at 280 nm. When further analyzing the peak corresponding with CPR, each spectrum was first height-normalized so that the maximum of the peak corresponding with chlorophenol red was the same for all spectra. Then, the wavelengths that correspond with 4 different absorbance intensities were determined and subtracted from the values of the control spectrum. The four differences were averaged to compute the overall wavelength shift. Reported averages are the average of the overall wavelength shift of the three initial replicates.
Color Imaging and Processing All pictures were taken with a Panasonic Lumix camera in a light-controlled setting. All pictures in figures showing color results are of 8 μL reactions in 384 well plates. The centers of selected reaction wells were cropped using Adobe Photoshop and combined to make color arrays. A brightness filter was uniformly applied to photos to make them better resemble actual appearance.
Lyophilization 30 μL reactions containing all components of the cell-free reaction (including lysate, small molecule mix, DNA templates, and CPRG) at a 1× concentration were prepared in PCR tubes and flash frozen in liquid nitrogen. Frozen samples were removed from liquid nitrogen and added to a Labconco Fast-freeze flask that contained a small amount of liquid nitrogen. Care was taken to transfer samples quickly and keep samples cold throughout the transfer process. Flasks were connected to a LabConco benchtop freeze-drier and lyophilized at −50° C. and 0.05 mbar for 3 hours. Samples were then removed and rehydrated on ice.
Results
Generalizability of Quantification Approach To demonstrate that the approach described in Example 1 can be used to quantify multiple classes of biomarkers using various molecular-level sensing mechanisms, the inventors applied the same framework to quantification of RNA via an established toehold switch (FIG. 4A). The inventors constitutively expressed a toehold switch from the plasmid pSwitch in the cell-free expression reaction to measure trigger RNA that was directly added to cell-free expression reactions. In this nucleic acid sensing implementation of the calibration approach, the pSwitch plasmid served as the response regulator (analogous to the pZntR plasmid in the zinc sensing application), and the trigger RNA was the biomarker. Thus, the test reaction had a defined amount of the pSwitch plasmid with no initial trigger RNA, and standard reference reactions have saturated levels of trigger RNA (FIG. 17) and variable amounts of the pSwitch plasmid. Standard reference reactions should reproduce the response of test reactions with different measured levels of trigger RNA. For each trigger concentration tested, the inventors identified a standard reaction that shows a nearly identical colorimetric output (FIG. 18); the relationship between trigger concentration in the test reactions and switch concentration in standard reactions was consistent across experiments (FIG. 19). From these data, the inventors determined the optimal set of switch concentrations that match each desired trigger concentration for a calibration curve.

Figure 4B:
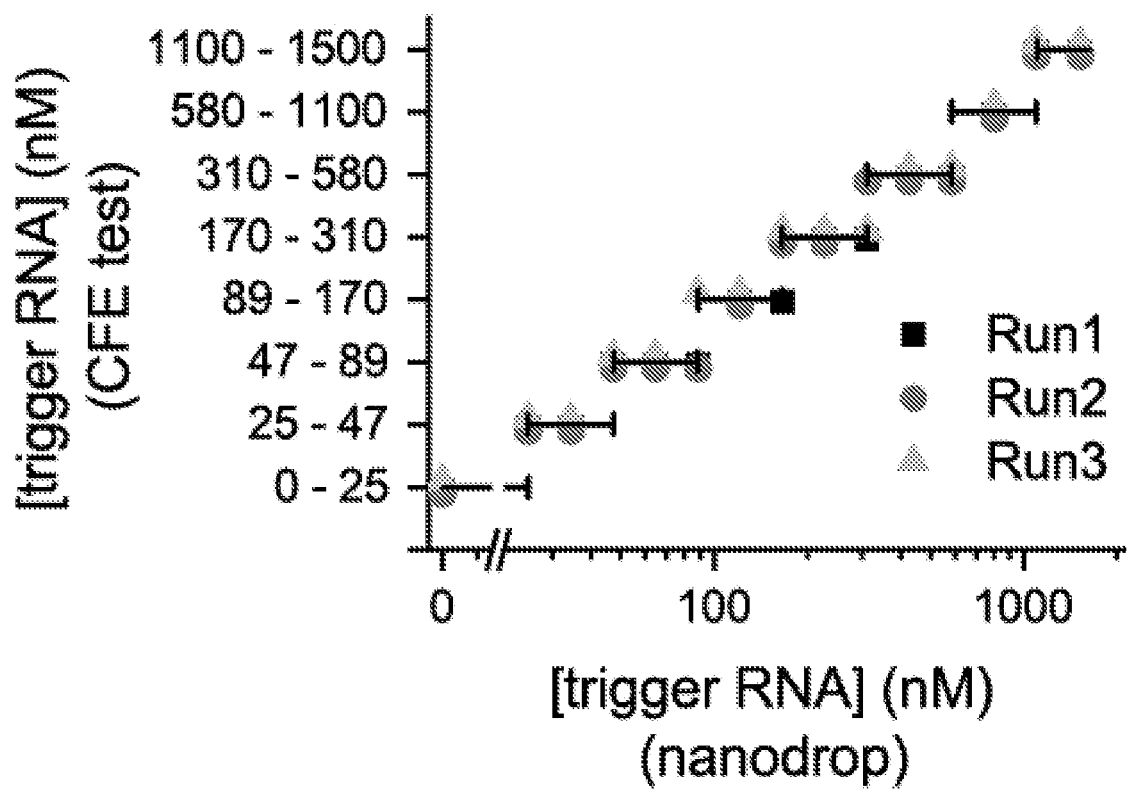
Figure 4C:
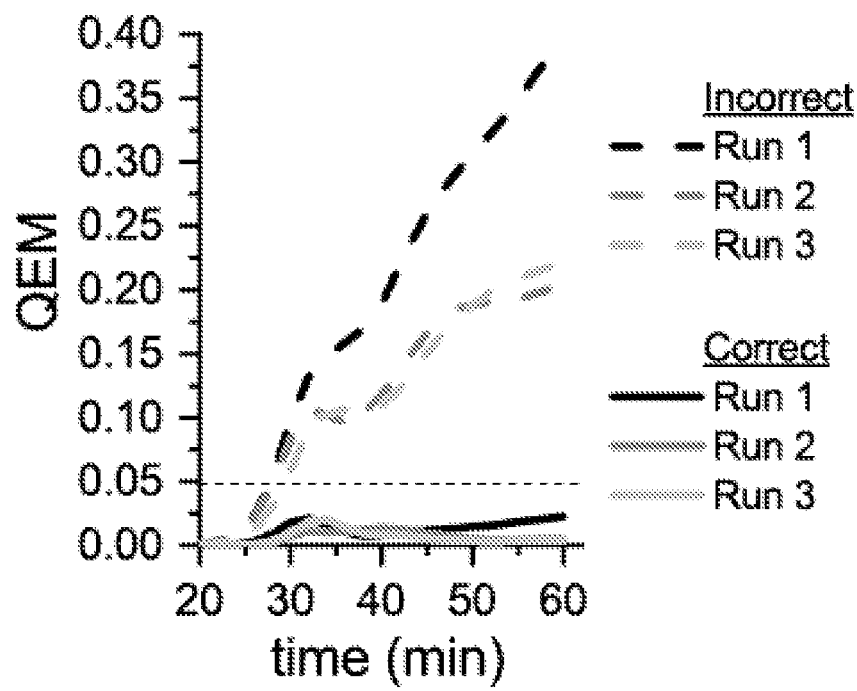
Figure 4D:
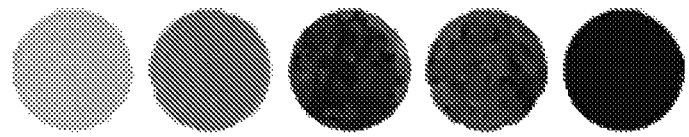
Figure 20:
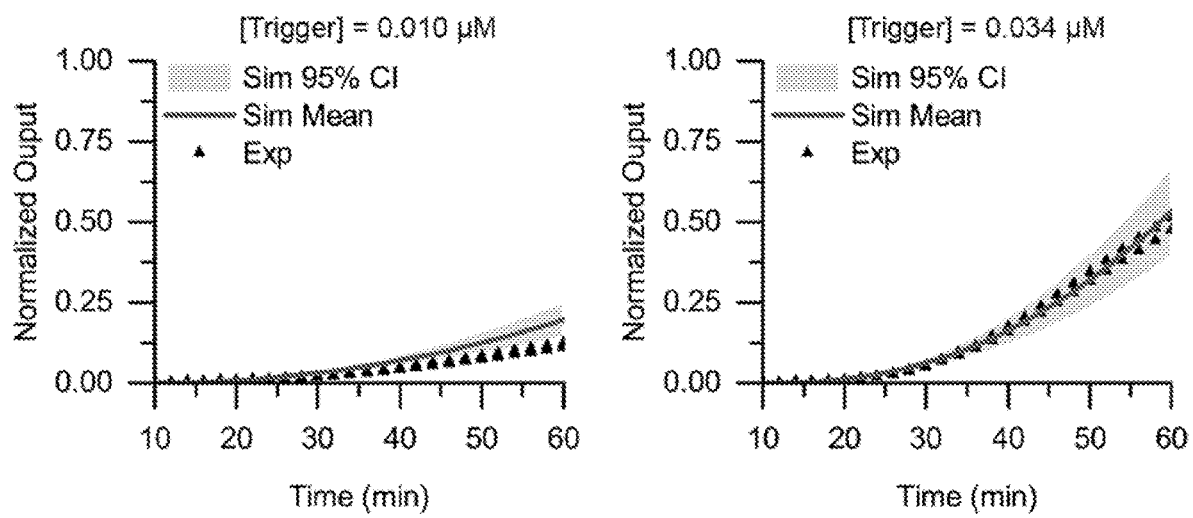
FIG. 20 shows the comparison of parameterized model to experimental data in toehold switch circuit. Experimental and model trajectories were normalized by the maximum theoretical CPR concentration (1000 µM). The mean simulated trajectories (dark gray line) are shown within the 95% confidence interval (light gray region) from the range of simulated trajectories; they closely predict the experimental data (black triangles).
Figure 20:
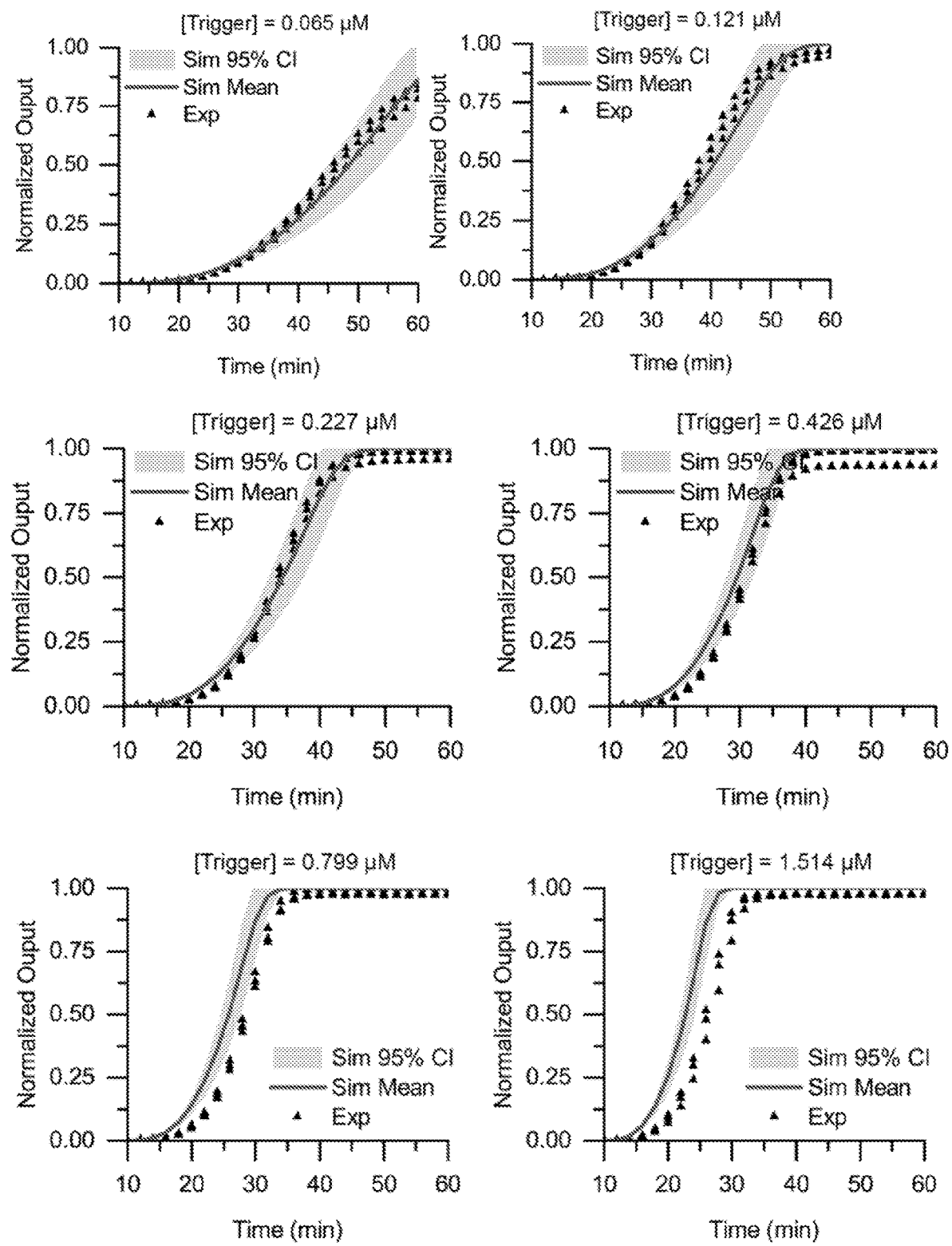
Figure 21A:
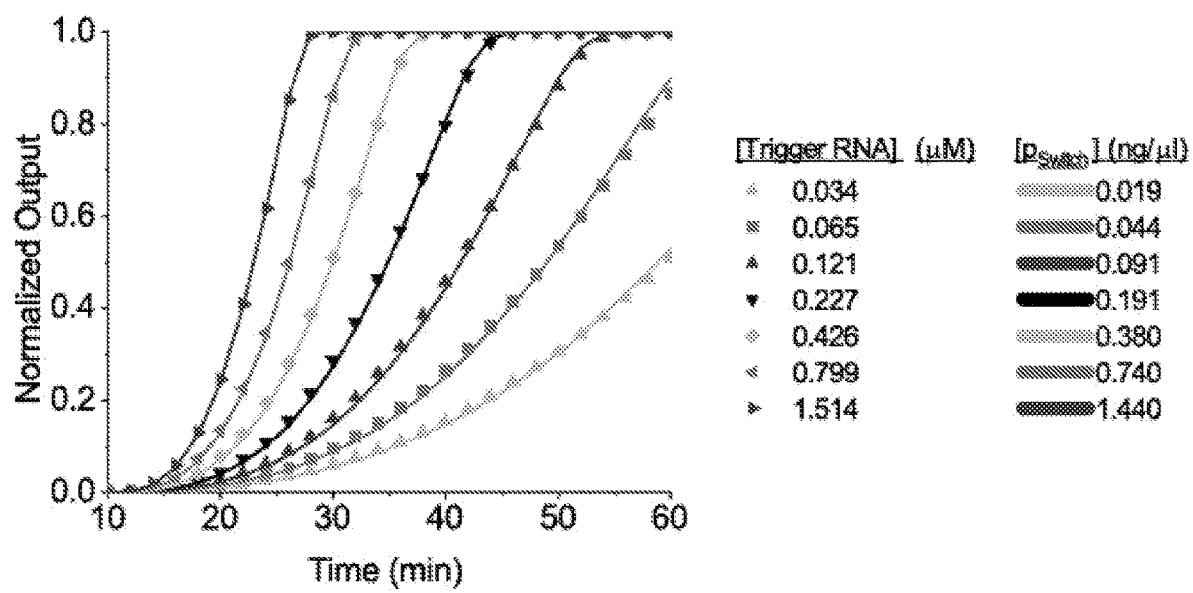
Figure 21B:
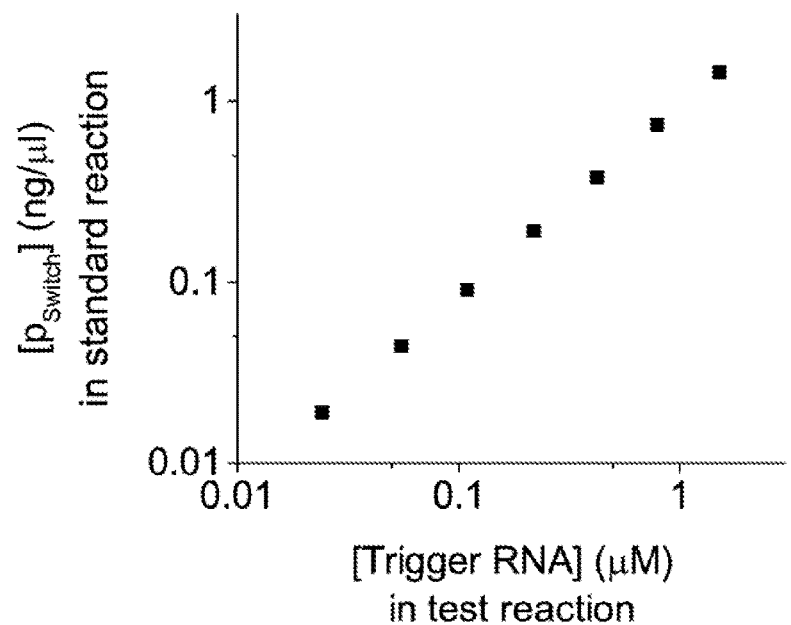
Figure 22:
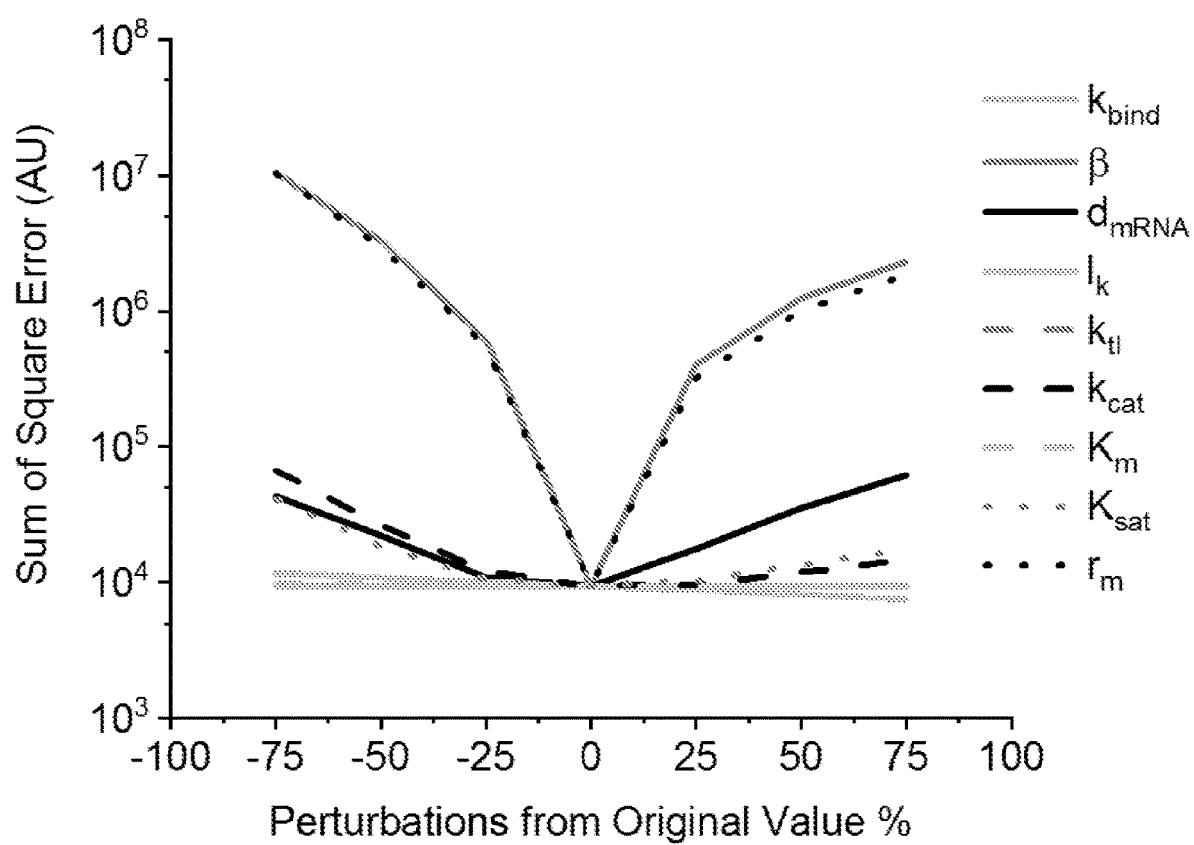
FIG. 22 shows the perturbation of parameter values to identify the most sensitive parameters in the toehold switch model. To determine which of the estimated parameters are the most sensitive, the inventors perturbed each parameter up to ±75% of its optimized value and calculated the sum of squared errors between the simulated test and standard reactions. We found the maturation rate of trigger RNA to its active form (r_m) and the transcription rate of switch (β) to be the most sensitive parameters.

Optimized standard reactions accurately quantified trigger concentrations in all test reactions (FIG. 4B). QEM quantification (FIG. 4C) showed nearly ideal test behavior across time points, and the colors of the test reactions accurately matched the color of the correct corresponding standard reactions (FIG. 4D). The inventors also created an ordinary differential equation model recapitulating toehold switch results from experiments (FIG. 20). Parameter values obtained from the estimation procedure mentioned before qualitatively reproduced the logarithmic relationship between trigger concentration in test reactions and switch concentration in standard reactions (FIG. 21A-21B). Of the identified parameters, the mapping of test and standard reaction was found to be most sensitive to changes in the maturation rate of trigger RNA to its active form and the transcriptional rate of the switch (FIG. 22).

The resulting RNA quantification platform could be used to directly quantify RNA in biological samples. It could also be used for more sensitive RNA assessment by processing samples through a pipeline that includes reverse transcription and transcription if the processing pipeline yields quantitatively reproducible amplification (the calibration approach can compensate for matrix effects, but not quantitative variation introduced by upstream processing).

Example 3: Detailed Statistical Analyses

The analyses described in this Example were used to develop the diagnostic assays described in Examples 1 and 2 above.
Definition of Quantification Error Metric The inventors defined a quantification error metric (QEM) to compare the absorbance readings of the test and standard reactions that should predict the test reaction. The inventors first calculated the difference between prediction and absorbance readings at each time point.

$$\Delta A(i, j) = | A_{580,predicted}(i) - A_{580,actual}(j) | \tag{1}$$

i=index of zinc prediction
j=index of zinc test evaluated

Then, the normalized sum of squared error for the correct prediction readings for each zinc concentration was calculated. The inventors defined this as the QEM of the correct predictions ($QEM_{correct}$). Ideally, the $QEM_{correct}$ should be zero to indicate identical absorbance curves between test reactions and the corresponding correct prediction.

$$QEM_{correct} = \frac{1}{n}\sum_{i=1}^{n} (\Delta A(i, i))^2 \tag{2}$$

n=number of zinc concentrations evaluated
i=index of zinc concentration evaluated The inventors next calculated the normalized sum of squared error for the closest incorrect predictions and defined this as the $QEM_{incorrect}$. Ideally, the $QEM_{incorrect}$ should be very high to indicate substantial absorbance differences corresponding with incorrect predictions.

$$QEM_{incorrect} = \frac{1}{2(n-1)}\sum_{i=1}^{n-1} (\Delta A(i, i+1))^2 + (\Delta A(i+1, i))^2 \tag{3}$$

n=number of zinc concentrations evaluated
i=index of zinc concentration evaluated In all evaluation of quantification error, the inventors set a threshold of 0.0484, which is $0.22^2$. Across all experiments, the average maximum $A_{580}$ value was approximately 2.2, so 0.22 corresponds with one-tenth of the spectrum. Values below the threshold indicate indistinguishable differences, and values above the threshold indicate distinguishable differences.
Computational Model of Parallel Calibration Approach
Model Equations and Assumptions The inventors created an ordinary differential equation model to recapitulate how the zinc-responsive circuit controls colorimetric output in a cell-free system, both in standard zinc-responsive reactions and in the reference reactions that are run at saturated zinc concentrations. Tables S1 and S2 list species and parameters represented in the model, and Table S3 lists the equations used to model the system.

TABLE S1

Species and their initial conditions in the model of zinc-response in cell-free reactions.

| Species | Description | Initial Condition | Unit |
| --- | --- | --- | --- |
| $Zn^{2+}$ | Zinc | Varied | μM |
| rZntR | mRNA of regulator ZntR | 0 | μM |
| ZntR | ZntR Protein | 0 | μM |
| ZntR* | Activated ZntR from zinc binding | 0 | μM |

TABLE S1-continued

Species and their initial conditions in the model of zinc-response in cell-free reactions.

| Species | Description | Initial Condition | Unit |
|---|---|---|---|
| rLacZ | mRNA of reporter LacZ | 0 | μM |
| LacZ | LacZ Protein | 0 | μM |
| CPRG | Substrate for LacZ | 1.00E+03 | μM |
| CPR | Colorimetric Output | 0 | μM |

TABLE S2

Zinc model parameters and estimated values.

| # | Parameter | Description | Initial Guesses | Estimated Values | Unit |
|---|---|---|---|---|---|
| 1 | $k_{bind}$ | Effective binding rate of Zinc and ZntR | 1.00E−03 (1, 2) | 3.54E−04 | $\mu M^{-2}s^{-1}$ |
| 2 | $\beta_1$ | Transcription rate of ZntR | 1.00E−03 (3) | 5.66E−03 | $\mu M s^{-1}$ |
| 3 | $d_{mRNA}$ | Degradation rate of mRNA | 1.50E−03 (3) | 1.08E−03 | $s^{-1}$ |
| 4 | $k_{tl}$ | Translational rate of proteins | 1.00E−03 (3) | 1.77E−03 | $s^{-1}$ |
| 5 | $\beta_2$ | Transcription rate of LacZ | 1.00E−03 (3) | 1.54E−03 | $\mu M s^{-1}$ |
| 6 | $K_{m1}$ | Activation coefficient of ZntR | 1.00E+02 (1) | 8.19E+01 | μM |
| 7 | $l_k$ | Leak coefficient of pZntA | 1.00E−03 | 1.26E−03 | unitless |
| 8 | $k_{cat}$ | Cleaving rate of LacZ | 1.00E+02 (2) | 5.14E+01 | $s^{-1}$ |
| 9 | $K_{m2}$ | Activation coefficient of LacZ | 1.00E+02 (2) | 1.91E+02 | μM |

TABLE S3

Equations used to model the zinc-response in cell-free reactions $$\frac{d[Zn^{2+}]}{dt} = -2k_{bind}[ZntR][Zn^{2+}]^2 \quad (4)$$

$$\frac{d[rZntR]}{dt} = \beta_1 - d_{mRNA}[rZntR] \quad (5)$$

$$\frac{d[ZntR]}{dt} = \frac{k_{tl}}{2}[rZntR] - k_{bind}[ZntR][Zn^{2+}]^2 \quad (6)$$

$$\frac{d[ZntR^*]}{dt} = k_{bind}[ZntR][Zn^{2+}]^2 \quad (7)$$

$$\frac{d[rLacZ]}{dt} = \beta_2\left(\frac{[ZntR^*]}{[ZntR^*] + K_{m1}} + l_k\right) - d_{mRNA}[rLacZ] \quad (8)$$

$$\frac{d[LacZ]}{dt} = k_{tl}[rLacZ] \quad (9)$$

$$\frac{d[CPRG]}{dt} = -k_{cat}[LacZ]\left(\frac{[CPRG]}{[CPRG] + K_{m2}}\right) \quad (10)$$

$$\frac{d[CPR]}{dt} = k_{cat}[LacZ]\left(\frac{[CPRG]}{[CPRG] + K_{m2}}\right) \quad (11)$$

The inventors' model makes the following simplifying assumptions:
1. Though ZntR is a homodimer, it is modeled as a single species that binds two zinc ions with mass action kinetics
2. Binding of zinc to ZntR is essentially irreversible
3. $k_{bind}$ is a lumped parameter of zinc binding to ZntR and the assumed constant percentage of zinc available in the cell free reaction (i.e., not bound to other proteins).
4. Protein degradation is negligible
5. Translation rates of all proteins are similar Sensitivity Analysis The inventors first performed a sensitivity analysis to identify which parameters could be estimated from experiments at which specific input (zinc concentration) regimes. The inventors calculated parameter sensitivity, starting from the literature parameter values, for in silico simulations at varying concentrations of zinc. This method created a time-varying sensitivity coefficient matrix Z for each experiment to analyze how each modeled species $x_i$ responds to perturbations in parameter $P_j$ for a simulation at a given concentration of zinc:

$$z_{ij} = \left.\frac{\partial x_i}{\partial p_j}\right|_t \quad (12)$$

i=1, 2, . . . , N, where N denotes the number of species
j=1, 2, . . . P, where P denotes the number of parameters Since the only measurable species in this experiment is the relative amount of CPR produced, the inventors focused on $Z_{CPR,j}(t)$ to determine which parameters can be estimated from experiments in a given input regime using the following procedure. A new matrix Q is defined where $Q_{ij} = z_{CPR,j}(t_i)$. The most sensitive parameter is found by locating the column in this temporal sensitivity matrix with the largest magnitude, as long as it is above a set threshold, which was $10^{-8}$. The most sensitive parameter was then marked as estimable, and a residual matrix was created by taking the difference between the matrix Q and the prediction of the full matrix Q using only the subset of columns that have already been marked as estimable. The magnitudes of the columns in that residual matrix are then used to determine whether any other remaining parameters are estimable. The same procedure was repeated on the residual matrix until the remaining parameters no longer pass the set threshold or until all parameters have been marked as estimable. The result was a determined set of parameters that will maximally influence the modeled trajectory for a given input regime. If any parameters were not marked as estimable, other zinc concentration simulations were considered (with parameters already marked estimable in previous experiments being set to zero in the sensitivity matrix) until all parameters were marked estimable in some experiment. The identification of which parameters can be estimated by which zinc concentration regimes is then used to guide the parameter estimation approach, yielding improved parameter estimates compared to standard parameter estimation.

Parameter Estimation

Model parameters were then estimated from each experiment by fitting the estimable parameters of each experiment to measured CPR concentrations at each measured time point. The objective function in the parameter estimation is:

$$\min(CPR_k^{exp,mean} - CPR_k^{sim}(\vec{p}))^2 \quad (13)$$

with $CPR_k^{exp,mean}$ denotes the mean value of the experimentally observed CPR concentration at time point $t_k$. $\vec{p}$ contains all of the estimable parameters in the experiment. $CPR_k^{sim}(\vec{p})$ denotes the model simulated CPR concentration at time $t_k$. For each experiment, optimal $\vec{p}$ were found using the MATLAB function fmincon with the constraints of $0.33\vec{p} \leq \vec{p} \leq 3.33\vec{p}$.

The inventors used parameter values sourced from the literature as the starting points for initial guesses for the parameter estimation. 100 sets of starting parameters were created by sampling from a uniform distribution±15% around each literature parameter value. Each set was then optimized by sequentially applying the fitting procedure above to experimental data, only fitting the identifiable parameters for a given experiment (zinc concentration). Parameters optimized from the previous experiment were used in place of initial guesses for fitting of subsequent parameters via additional experimental data. This procedure was repeated for each initial set of parameters to produce 100 sets of estimated parameters. The inventors then selected the set of estimated parameters that minimized the error compared to all of the experimental data, and used that as the starting point for the next round of optimization. These current guesses were used as the starting point for new initial guesses, by creating 100 sets of starting parameters by sampling from a uniform distribution±15% around each literature parameter value. This optimization process was iterated 10 times to generate the final optimal parameter set.

The inventors also attempted to simultaneously optimize all parameters for all experimental data, but based on the high dimensionality of the system and the characteristics of the fitness landscape, they found that the strategy described here returned better-fitting parameter values.

Test and Standard Reactions Mapping

The parameterized model was used to find the zinc saturation point, where increasing zinc concentration does not lead to an increase in CPR production. This saturation point was then used as the zinc input in simulating all standard reactions. When simulating the standard reactions, only the transcriptional rate of ZntR ($\beta_1$) was changed, to correspond to changing ZntR plasmid concentrations. $\beta_1$ is a lumped parameter that is the product of transcriptional activities and plasmid concentration. Assuming a linear relation between plasmid concentration and mRNA production, a transcriptional activity can be inferred from the knowledge of the actual plasmid concentration for a given set of experimental data and the inferred $\beta_1$ for that dataset. This transcriptional activity can then be used to move back and forth between inferred $\beta_1$ values and plasmid concentrations.

To find the optimal $\beta_1$ for each standard reaction, the MATLAB function fmincon with the same constraint described above was used to estimate $\beta_1$, using the experimentally determined ZntR plasmid concentration as the initial guess and minimizing the sum of squared error between simulated test and standard reactions as the objective function. The computationally predicted ZntR plasmid concentration was then back-calculated from the estimated $\beta_1$.

Parameter Perturbations

To identify the parameters that significantly affect the mapping of test and standard reactions, the inventors performed additional parameter sensitivity analysis using parameter perturbations (±75% of their estimated values) and calculated the sum of squared error between the test and standard reactions. The inventors found that 4 parameters strongly affect test and standard mapping at low zinc concentrations: the effective binding constant of zinc to ZntR ($k_{bind}$), transcriptional rate of ZntR WO, degradation rate of mRNA ($d_{mRNA}$), and translation rate of protein ($k_{tl}$). The inventors also found that the cleavage rate of CPRG to CPR ($k_{cat}$) strongly affects mapping at higher zinc concentrations.

Computational Model of Trigger Response and Standardization Approach

Model Equations and Assumptions

The inventors used the same ODE modeling approach to create to recapitulate the toehold switch-mediated response to added trigger RNA. Tables S4 and S5 list model species and parameters represented in the model, and Table S6 lists the equations used to model the toehold switch system

TABLE S4

Species and their initial conditions in the model of toehold switch circuit in cell-free reactions.

| Species | Description | Initial Condition | Unit |
|---|---|---|---|
| rTrigger | Trigger RNA | Varied | μM |
| rTrigger* | Correctly folded trigger RNA | 0 | μM |
| rSwitch | Switch mRNA encoding LacZ | 0 | μM |
| rSwitch* | Activated switch mRNA from trigger binding | 0 | μM |
| LacZ | LacZ Protein | 0 | μM |
| CPRG | Substrate for LacZ | 1.00E+03 | μM |
| CPR | Colorimetric Output | 0 | μM |

TABLE S5

Toehold Switch model parameters and estimated values.

| # | Parameter | Description | Initial Guesses | Estimated Values | Unit |
|---|---|---|---|---|---|
| 1 | $k_{bind}$ | Binding rate of Trigger to Switch | 1.00E+03 | 1.03E+03 | $\mu M^{-2} s^{-1}$ |
| 2 | $\beta$ | Transcription rate of Switch mRNA | 1.00E-03 (3) | 7.26E-04 | $\mu M s^{-1}$ |
| 3 | $d_{mRNA}$ | Degradation rate of mRNA | 1.50E-03 (3) | 2.06E-04 | $s^{-1}$ |
| 4 | $l_k$ | Leak coefficient of Switch mRNA | 1.00E-03 (3) | 6.33E-04 | unitless |
| 5 | $k_{tl}$ | Translation rate of LacZ | 1.00E-03 (3) | 9.29E-04 | $\mu M s^{-1}$ |

TABLE S5-continued

Toehold Switch model parameters and estimated values.

| # | Parameter | Description | Initial Guesses | Estimated Values | Unit |
|---|---|---|---|---|---|
| 6 | $k_{cat}$ | Cleaving rate of LacZ | 1.00E+02 (2) | 7.85E+01 | $\mu M s^{-1}$ |
| 7 | $K_m$ | Activation coefficient of LacZ | 1.00E+02 (2) | 8.28E+01 | $\mu M$ |
| 8 | $K_{sat}$ | Activation coefficient of Trigger | 1.00E+01 | 4.07E+00 | $\mu M$ |
| 9 | $r_m$ | Maturation rate of Trigger | 1.00E-04 (3) | 3.10E-04 | $\mu M s^{-1}$ |

TABLE S6

Equations used to model the toehold switch in cell-free reactions $$\frac{d[rTrigger]}{dt} = -d_{mRNA}[rTrigger] - r_m[rTrigger] \tag{14}$$

$$\frac{d[rTrigger^*]}{dt} = r_m[rTrigger] - d_{mRNA}[rTrigger^*] - k_{bind}[rTrigger^*][rSwitch] \tag{15}$$

$$\frac{d[rSwitch]}{dt} = \beta - d_{mRNA}[rSwitch] - k_{bind}[rTrigger^*][rSwitch] \tag{16}$$

$$\frac{d[rSwitch^*]}{dt} = k_{bind}[rTrigger^*][rSwitch] - d_{mRNA}[rSwitch^*] \tag{17}$$

$$\frac{d[LacZ]}{dt} = k_{tl}\left(\frac{[Switch^*]}{[Switch^*] + K_{sat}} + l_k\right) \tag{18}$$

$$\frac{d[CPRG]}{dt} = -k_{cat}[LacZ]\left(\frac{[CPRG]}{[CPRG] + K_m}\right) \tag{19}$$

$$\frac{d[CPR]}{dt} = k_{cat}[LacZ]\left(\frac{[CPRG]}{[CPRG] + K_m}\right) \tag{20}$$

The toehold switch model makes the following simplifying assumptions:
1. Trigger RNA must fold into the correct conformation to bind to Switch RNA
2. Binding of folded Trigger RNA to Switch mRNA is irreversible
3. Protein degradation is negligible
4. Previously estimated parameter values ($\beta$, $d_{mRNA}$, $k_{tl}$, $k_{cat}$, and $K_m$) need to be re-estimated due to the different lysate preparation method and energy buffer used Test and Standard Reactions Mapping All parameter values in the toehold switch model were found using the same sensitivity analysis and parameter estimation method used for the zinc model. The parameterized model was used to find the trigger saturation point. This saturation point was then used as the trigger RNA input in simulating all standard reactions. When simulating the standard reactions, only the transcriptional rate of the switch ($\beta$) was changed to correspond to changing switch plasmid concentrations.

To find the optimal $\beta$ in each standard reaction, the MATLAB function fmincon with the same constraint described above was used to estimate $\beta$, using the experimentally determined Switch plasmid concentration as the initial guess and minimizing the sum of squared error between simulated test and standard reactions as the objective function.

Parameter Perturbations

To identify the parameters that significantly affect the mapping of test and standard reactions, the inventors performed additional parameter sensitivity analysis using parameter perturbations (±75% of their estimated values) and calculated the sum of squared error between the test and standard reactions. The inventors found that 2 parameters strongly affect test and standard mapping across all concentrations of trigger RNA in test reactions: the maturation rate of trigger RNA to active form ($r_m$) and the transcriptional rate of the switch ($\beta$).

List of Embodiments

The following list of embodiments specifically contemplates that any of the dependent claims/embodiments can apply to any of the embodiments disclosed herein.
1. A method of generating a diagnostic tool for measuring an unknown amount of an analyte in a biological sample using a cell-free extract (CFE), the diagnostic tool comprising a plurality of reference points, each reference point being a distinct color and corresponding to a different amount of the analyte, the method comprising:
   determining a desired amount of a regulator of a reporter;
   determining a saturating amount of the analyte; and
   determining a desired reaction time,
   wherein the desired amount of the regulator of the reporter, the saturating amount of the analyte, and the desired reaction time are determined such that when the unknown amount of the analyte in the biological sample is combined with the CFE, and the desired amount of the regulator of the reporter for the desired reaction time, a colorimetric gene product is generated having a color corresponding to a color of a first reference point in the plurality of reference points containing the biological sample, the CFE, the saturating amount of analyte, and the desired amount of the regulator of the reporter, the first reference point associated with an amount of the analyte about equal to the unknown amount of analyte, wherein the method is configured to reduce or eliminate inter-sample variability.

2. The method of embodiment 1, further comprising providing the plurality of reference points.

3. The method of embodiment 1 or 2, wherein the step of determining the desired reaction time further comprises:

adding certain concentrations of the analyte to a plurality of reaction points, each of the plurality of reaction points containing the same amount of the regulator of the reporter, the biological sample, and the CFE;

analyzing color and/or absorbance of the plurality of reaction points over time;

plotting the color and/or absorbance of the plurality of reaction points over time versus the concentrations of the analyte; and determining which time point yields a color and/or absorbance output spanning a desired range of absorbances across the analyte concentration range.

4. The method of embodiments 1-3, wherein the step of determining the saturating amount of the analyte further comprises:

adding certain amounts of the analyte to a plurality of reaction points containing the same amount of the regulator of the reporter, the biological sample, and the CFE;

analyzing color and/or absorbance of the plurality of reaction points over a time course;

plotting the color and/or absorbance of the plurality of reaction points versus the reaction time; and determining which amounts of the analyte yield substantially similar color and/or absorbance output throughout the time course.

5. The method of embodiments 1-4, wherein determining the varying amounts of the regulator of the reporter further comprises:

adding certain amounts of the analyte to a plurality of reaction points containing a certain amount of the analyte, the biological sample, and the CFE;

analyzing color and/or absorbance of the plurality of reaction points over a time course;

plotting the color and/or absorbance of the plurality of reaction points versus the reaction time; and determining which amounts of the regulator of the reporter yield color and/or absorbance outputs throughout the time course that are substantially similar to the color and/or absorbance outputs throughout a time course of different amounts of analyte.

6. The method of embodiment 5, further comprising calculating the best-fit reaction for each amount of the regulator of the reporter to include in the series of the standard reference reactions, the calculating step comprising:

calculating the sum of squared error (SSE) minimization between each standard and test reaction at a series of time points spanning the determined reaction time, wherein the standard reaction that has the lowest SSE is determined to be the best-fit reaction for that amount of the regulator of the reporter.

7. The method of embodiments 1-6, wherein the biological sample is a biological fluid sample.

8. The method of embodiment 7, wherein the biological fluid sample is selected from the group consisting of blood, serum, plasma, urine, saliva, tears, mucus, lymph, interstitial fluid, cerebrospinal fluid, pus, breast milk, and amniotic fluid.

9. The method of embodiments 1-8, wherein the reporter is plasmid-based or is present on a linear fragment of DNA.

10. The method of embodiment 9, wherein the plasmid-based reporter comprises the regulator and a reporter gene operatively linked to a genetic element that is regulated by the regulator.

11. The method of embodiment 9, wherein the linear fragment of DNA comprises the regulator and a reporter gene operatively linked to a genetic element that is regulated by the regulator.

12. The method of embodiment 9, wherein the regulator comprises a transcription factor, a repressor, and an activator.

13. The method of embodiment 10 or 11, wherein the genetic element comprises a promoter, one or more regulatory protein binding sites, one or more repressor binding sites, and one or more transcription factor binding sites.

14. The method of embodiment 10 or 11, wherein the reporter gene produces a colorimetric gene product.

15. The method of embodiment 14, wherein the colorimetric gene product comprises a fluorescent protein, a luminescent protein, a colored protein, a protein that produces a detectable and quantifiable product, and a protein that can be quantified by measuring its absorbance at a wavelength.

16. The method of embodiments 1-15, wherein the analyte is zinc.

17. The method of embodiment 16, wherein the reporter comprises a first plasmid containing a transcriptional regulator ZntR and a second plasmid containing a reporter gene operatively linked to a ZntA promoter, wherein expression from the ZntA promoter is controlled by the amount of the transcriptional regulator ZntR.

18. The method of embodiments 1-15, wherein the analyte is RNA.

19. The method of embodiment 18, wherein the plasmid-based reporter comprises a first plasmid containing a toehold switch activated by a trigger RNA sequence that is operatively linked to a reporter gene, wherein expression of the reporter gene is controlled by the amount of the trigger RNA sequence.

20. A method for generating a range of visible colors in serum samples with unknown amounts of an analyte by addition of a small molecule, wherein the small molecule displaces an interfering molecule from one or more of a regulator, a reporter, and a molecule acted on by the reporter, the method comprising:

determining a desired amount of a regulator of a reporter;
determining a saturating amount of the analyte; and
determining a desired reaction time, wherein the desired amount of the regulator of the reporter, the saturating amount of the analyte, and the desired reaction time are determined such that when the unknown amount of the analyte is combined with the serum, and the desired amount of the regulator of the reporter for the desired reaction time, a colorimetric gene product is generated having a color corresponding to a color of a first reference point in the plurality of reference points containing the serum, the saturating amount of analyte, and the desired amount of the regulator of the reporter, the first reference point associated with an amount of the analyte about equal to the unknown amount of analyte, and wherein the method is configured to reduce or eliminate inter-sample variability.

21. The method of embodiment 20, wherein the interfering molecule comprises a protein, DNA, and RNA.

22. The method of embodiment 20 or 21, wherein the small molecule comprises a colorless compound that tightly interacts with the interfering molecule.

23. The method of embodiment 20-22, further comprising providing the plurality of reference points.

24. The method of embodiments 20-23, wherein the step of determining the desired reaction time further comprises:

adding certain concentrations of the analyte to a plurality of reaction points, each of the plurality of reaction points containing the same amount of the regulator of the reporter and the serum;

analyzing color and/or absorbance of the plurality of reaction points over time;

plotting the color and/or absorbance of the plurality of reaction points over time versus the concentrations of the analyte; and determining which time point yields a color and/or absorbance output spanning a desired range of absorbances across the analyte concentration range.

25. The method of embodiments 20-24, wherein the step of determining the saturating amount of the analyte further comprises:

adding certain amounts of the analyte to a plurality of reaction points containing the same amount of the regulator of the reporter and the serum;

analyzing color and/or absorbance of the plurality of reaction points over a time course;

plotting the color and/or absorbance of the plurality of reaction points versus the reaction time; and determining which amounts of the analyte yield substantially similar color and/or absorbance output throughout the time course.

26. The method of embodiments 20-25, wherein determining the varying amounts of the regulator of the reporter further comprises:

adding certain amounts of the analyte to a plurality of reaction points containing a certain amount of the analyte and the serum;

analyzing color and/or absorbance of the plurality of reaction points over a time course;

plotting the color and/or absorbance of the plurality of reaction points versus the reaction time; and determining which amounts of the regulator of the reporter yield color and/or absorbance outputs throughout the time course that are substantially similar to the color and/or absorbance outputs throughout a time course of different amounts of analyte.

27. The method of embodiment 26, further comprising calculating the best-fit reaction for each amount of the regulator of the reporter to include in the series of the standard reference reactions, the calculating step comprising:

calculating the sum of squared error (SSE) minimization between each standard and test reaction at a series of time points spanning the determined reaction time, wherein the standard reaction that has the lowest SSE is determined to be the best-fit reaction for that amount of the regulator of the reporter.

28. The method of embodiments 20-27, wherein the reporter is plasmid-based or is present on a linear fragment of DNA.

29. The method of embodiment 28, wherein the plasmid-based reporter comprises the regulator and a reporter gene operatively linked to a genetic element that is regulated by the regulator.

30. The method of embodiment 28, wherein the linear fragment of DNA comprises the regulator and a reporter gene operatively linked to a genetic element that is regulated by the regulator.

31. The method of embodiment 28, wherein the regulator comprises a transcription factor, a repressor, and an activator.

32. The method of embodiment 29 or 30, wherein the genetic element comprises a promoter, one or more regulatory protein binding sites, one or more repressor binding sites, and one or more transcription factor binding sites.

33. The method of embodiment 29 or 30, wherein the reporter gene produces a colorimetric gene product.

34. The method of embodiment 33, wherein the colorimetric gene product comprises a fluorescent protein, a luminescent protein, a colored protein, a protein that produces a detectable and quantifiable product, and a protein that can be quantified by measuring its absorbance at a wavelength.

35. A diagnostic tool for measuring an unknown amount of an analyte in a biological sample with a cell-free extract (CFE), the tool comprising:

a first reference point having a first distinct color corresponding to a first amount of the analyte;

a second reference point having a second distinct color corresponding to a second amount of the analyte; and a third reference point having a third distinct color corresponding to a third amount of the analyte, wherein the first distinct color is substantially similar to a colorimetric gene product generated when a biological sample with the first amount of the analyte is combined with a predetermined amount of the CFE, a regulator of a reporter and a predetermined saturation amount of the analyte for a predetermined reaction time, wherein the second distinct color is substantially similar to a colorimetric gene product generated when a biological sample with the second amount of the analyte is combined with the CFE, the predetermined amount of the regulator of a reporter and the predetermined saturation amount of the analyte for the predetermined reaction time, wherein the third distinct color is substantially similar to a colorimetric gene product generated when a biological sample with the third amount of the analyte is combined with the CFE, the predetermined amount of the regulator of a reporter and the predetermined saturation amount of the analyte for the predetermined reaction time, and wherein the diagnostic tool is configured to reduce or eliminate inter-sample variability.

36. The diagnostic tool of embodiment 35, further comprising providing the plurality of reference points.

37. The diagnostic tool of embodiment 35 or 36, wherein determining the predetermined reaction time further comprises:

adding certain concentrations of the analyte to a plurality of reaction points, each of the plurality of reaction points containing the same amount of the regulator of the reporter, the biological sample, and the CFE;

analyzing color and/or absorbance of the plurality of reaction points over time;

plotting the color and/or absorbance of the plurality of reaction points over time versus the concentrations of the analyte; and determining which time point yields a color and/or absorbance output spanning a desired range of absorbances across the analyte concentration range.

38. The diagnostic tool of embodiments 35-37, wherein determining the predetermined saturating amount of the analyte further comprises:

adding certain amounts of the analyte to a plurality of reaction points containing the same amount of the regulator of the reporter, the biological sample, and the CFE;

analyzing color and/or absorbance of the plurality of reaction points over a time course;

plotting the color and/or absorbance of the plurality of reaction points versus the reaction time; and determining which amounts of the analyte yield substantially similar color and/or absorbance output throughout the time course.

39. The diagnostic tool of embodiments 35-38, wherein determining the predetermined amount of the regulator of the reporter further comprises:

adding certain amounts of the regulator to a plurality of reaction points containing a certain amount of the analyte, the biological sample, and the CFE;

analyzing color and/or absorbance of the plurality of reaction points over a time course;

plotting the color and/or absorbance of the plurality of reaction points versus the reaction time; and determining which amounts of the regulator of the reporter yield color and/or absorbance outputs throughout the time course that are substantially similar to the color and/or absorbance outputs throughout a time course of different amounts of analyte.

40. The diagnostic tool of embodiment 39, further comprising calculating the best-fit reaction for each amount of the regulator of the reporter to include in the series of the standard reference reactions, the calculating step comprising:

calculating the sum of squared error (SSE) minimization between each standard and test reaction at a series of time points spanning the determined reaction time, wherein the standard reaction that has the lowest SSE is determined to be the best-fit reaction for that amount of the regulator of the reporter.

41. The diagnostic tool of embodiments 35-40, wherein the biological sample is a biological fluid sample.

42. The diagnostic tool of embodiment 41, wherein the biological fluid sample is selected from the group consisting of blood, serum, plasma, urine, saliva, tears, mucus, lymph, interstitial fluid, cerebrospinal fluid, pus, breast milk, and amniotic fluid.

43. The diagnostic tool of embodiments 35-42, wherein the reporter is plasmid-based or is present on a linear fragment of DNA.

44. The diagnostic tool of embodiment 43, wherein the plasmid-based reporter comprises the regulator and a reporter gene operatively linked to a genetic element that is regulated by the regulator.

45. The diagnostic tool of embodiment 43, wherein the linear fragment of DNA comprises the regulator and a reporter gene operatively linked to a genetic element that is regulated by the regulator.

46. The diagnostic tool of embodiment 43, wherein the regulator comprises a transcription factor, a repressor, and an activator.

47. The diagnostic tool of embodiment 44 or 45, wherein the genetic element comprises a promoter, one or more regulatory protein binding sites, one or more repressor binding sites, and one or more transcription factor binding sites.

48. The diagnostic tool of embodiment 44 or 45, wherein the reporter gene produces a colorimetric gene product.

49. The diagnostic tool of embodiment 48, wherein the colorimetric gene product comprises a fluorescent protein, a luminescent protein, a colored protein, a protein that produces a detectable and quantifiable product, and a protein that can be quantified by measuring its absorbance at a wavelength.

50. The diagnostic tool of embodiment 35-49, further comprising addition of a small molecule, wherein the small molecule displaces an interfering molecule from one or more of the regulator, the reporter, and a molecule acted on by the reporter.

51. A method of measuring an unknown amount of an analyte in a biological sample using a cell-free extract (CFE), the method comprising:

providing a diagnostic tool, the tool comprising a plurality of reference points, each reference point in the plurality of reference points being a distinct color and corresponding to a predetermined different amount of the analyte;

combining the biological sample, CFE, a predetermined saturating amount of the analyte, and a predetermined amount of a regulator of a reporter;

reacting the regulator of the reporter with the analyte for a predetermined reaction time to generate a colorimetric gene product;

determining a first reference point in the plurality of reference points having a color corresponding to the generated colorimetric gene product, wherein the predetermined different amount of the analyte corresponding to the first reference point is equal to the unknown amount of the analyte in the biological sample added to the CFE, and wherein the method is configured to reduce or eliminate inter-sample variability.

52. The method of embodiment 51, further comprising providing the plurality of reference points.

53. The method of embodiment 51 or 52, wherein determining the predetermined reaction time further comprises:

adding certain concentrations of the analyte to a plurality of reaction points, each of the plurality of reaction points containing the same amount of the regulator of the reporter, the biological sample, and the CFE;

analyzing color and/or absorbance of the plurality of reaction points over time;

plotting the color and/or absorbance of the plurality of reaction points over time versus the concentrations of the analyte; and determining which time point yields a color and/or absorbance output spanning a desired range of absorbances across the analyte concentration range.

54. The method of embodiments 51-53, wherein determining the predetermined saturating amount of the analyte further comprises:

adding certain amounts of the analyte to a plurality of reaction points containing the same amount of the regulator of the reporter, the biological sample, and the CFE;

analyzing color and/or absorbance of the plurality of reaction points over a time course;

plotting the color and/or absorbance of the plurality of reaction points versus the reaction time; and determining which amounts of the analyte yield substantially similar color and/or absorbance output throughout the time course.

55. The method of embodiments 51-54, wherein determining the predetermined amount of the regulator of the reporter further comprises:

adding certain amounts of the regulator to a plurality of reaction points containing a certain amount of the analyte, the biological sample, and the CFE;

analyzing color and/or absorbance of the plurality of reaction points over a time course;

plotting the color and/or absorbance of the plurality of reaction points versus the reaction time; and determining which amounts of the regulator of the reporter yield color and/or absorbance outputs throughout the time course that are substantially similar to the color and/or absorbance outputs throughout a time course of different amounts of analyte.

56. The method of embodiment 55, further comprising calculating the best-fit reaction for each amount of the regulator of the reporter to include in the series of the standard reference reactions, the calculating step comprising:

calculating the sum of squared error (SSE) minimization between each standard and test reaction at a series of time points spanning the determined reaction time, wherein the standard reaction that has the lowest SSE is determined to be the best-fit reaction for that amount of the regulator of the reporter.

57. The method of embodiments 51-56, wherein the biological sample is a biological fluid sample.

58. The method of embodiment 57, wherein the biological fluid sample is selected from the group consisting of blood, serum, plasma, urine, saliva, tears, mucus, lymph, interstitial fluid, cerebrospinal fluid, pus, breast milk, and amniotic fluid.

59. The method of embodiments 51-58, wherein the reporter is plasmid-based or is present on a linear fragment of DNA.

60. The method of embodiment 59, wherein the plasmid-based reporter comprises the regulator and a reporter gene operatively linked to a genetic element that is regulated by the regulator.

61. The method of embodiment 59, wherein the linear fragment of DNA comprises the regulator and a reporter gene operatively linked to a genetic element that is regulated by the regulator.

62. The method of embodiment 59, wherein the regulator comprises a transcription factor, a repressor, and an activator.

63. The method of embodiment 60 or 61, wherein the genetic element comprises a promoter, one or more regulatory protein binding sites, one or more repressor binding sites, and one or more transcription factor binding sites.

64. The method of embodiment 60 or 61, wherein the reporter gene produces a colorimetric gene product.

65. The method of embodiment 64, wherein the colorimetric gene product comprises a fluorescent protein, a luminescent protein, a colored protein, a protein that produces a detectable and quantifiable product, and a protein that can be quantified by measuring its absorbance at a wavelength.

66. The method of embodiments 51-65, further comprising addition of a small molecule, wherein the small molecule displaces an interfering molecule from one or more of the regulator, the reporter, and a molecule acted on by the reporter.

67. A method of generating a diagnostic tool for measuring an unknown amount of an analyte in an aqueous solution, the diagnostic tool comprising a plurality of reference points, each reference point being a distinct color and corresponding to a different amount of the analyte, the method comprising:

determining a desired amount of a regulator of a reporter;
determining a saturating amount of the analyte; and
determining a desired reaction time,
wherein the desired amount of the regulator of the reporter, the saturating amount of the analyte, and the desired reaction time are determined such that when the unknown amount of the analyte is combined with the aqueous solution, and the desired amount of the regulator of the reporter for the desired reaction time, a colorimetric gene product is generated having a color corresponding to a color of a first reference point in the plurality of reference points containing the aqueous solution, the saturating amount of analyte, and the desired amount of the regulator of the reporter, the first reference point associated with an amount of the analyte about equal to the unknown amount of analyte, and wherein the method is configured to reduce or eliminate inter-sample variability.

68. The method of embodiment 67, further comprising providing the plurality of reference points.

69. The method of embodiment 67 or 68, wherein the step of determining the desired reaction time further comprises:

adding certain concentrations of the analyte to a plurality of reaction points, each of the plurality of reaction points containing the same amount of the regulator of the reporter and the aqueous solution;

analyzing color and/or absorbance of the plurality of reaction points over time;

plotting the color and/or absorbance of the plurality of reaction points over time versus the concentrations of the analyte; and determining which time point yields a color and/or absorbance output spanning a desired range of absorbances across the analyte concentration range.

70. The method of embodiments 67-69, wherein the step of determining the saturating amount of the analyte further comprises:

adding certain amounts of the analyte to a plurality of reaction points containing the same amount of the regulator of the reporter and the aqueous solution;

analyzing color and/or absorbance of the plurality of reaction points over a time course;

plotting the color and/or absorbance of the plurality of reaction points versus the reaction time; and determining which amounts of the analyte yield substantially similar color and/or absorbance output throughout the time course.

71. The method of embodiments 67-70, wherein determining the varying amounts of the regulator of the reporter further comprises:

adding certain amounts of the analyte to a plurality of reaction points containing a certain amount of the analyte and the aqueous solution;

analyzing color and/or absorbance of the plurality of reaction points over a time course;

plotting the color and/or absorbance of the plurality of reaction points versus the reaction time; and determining which amounts of the regulator of the reporter yield color and/or absorbance outputs throughout the time course that are substantially similar to the color and/or absorbance outputs throughout a time course of different amounts of analyte.

72. The method of embodiment 71, further comprising calculating the best-fit reaction for each amount of the regulator of the reporter to include in the series of the standard reference reactions, the calculating step comprising:

calculating the sum of squared error (SSE) minimization between each standard and test reaction at a series of time points spanning the determined reaction time, wherein the standard reaction that has the lowest SSE is determined to be the best-fit reaction for that amount of the regulator of the reporter.

73. The method of embodiments 67-72, wherein the aqueous solution is water.

74. The method of embodiment 73, wherein the water is taken from a lake, an ocean, a river, a source of potable water, wastewater, rainwater runoff, or an industrial discharge, effluent, or waste stream.

75. The method of embodiments 67-74, wherein the reporter is plasmid-based or is present on a linear fragment of DNA.

76. The method of embodiment 75, wherein the plasmid-based reporter comprises the regulator and a reporter gene operatively linked to a genetic element that is regulated by the regulator.

77. The method of embodiment 75, wherein the linear fragment of DNA comprises the regulator and a reporter gene operatively linked to a genetic element that is regulated by the regulator.

78. The method of embodiment 75, wherein the regulator comprises a transcription factor, a repressor, and an activator.

79. The method of embodiment 76 or 77, wherein the genetic element comprises a promoter, one or more regulatory protein binding sites, one or more repressor binding sites, and one or more transcription factor binding sites.

78. The method of embodiment 76 or 77, wherein the reporter gene produces a colorimetric gene product.

79. The method of embodiment 78, wherein the colorimetric gene product comprises a fluorescent protein, a luminescent protein, a colored protein, a protein that produces a detectable and quantifiable product, and a protein that can be quantified by measuring its absorbance at a wavelength.

80. A method for generating a range of visible colors in aqueous samples with unknown amounts of an analyte by addition of a small molecule, wherein the small molecule displaces an interfering molecule from one or more of a regulator, a reporter, and a molecule acted on by the reporter, the method comprising:

determining a desired amount of a regulator of a reporter;
determining a saturating amount of the analyte; and
determining a desired reaction time,
wherein the desired amount of the regulator of the reporter, the saturating amount of the analyte, and the desired reaction time are determined such that when the unknown amount of the analyte is combined with the aqueous solution, and the desired amount of the regulator of the reporter for the desired reaction time, a colorimetric gene product is generated having a color corresponding to a color of a first reference point in the plurality of reference points containing the aqueous solution, the saturating amount of analyte, and the desired amount of the regulator of the reporter, the first reference point associated with an amount of the analyte about equal to the unknown amount of analyte, and
wherein the method is configured to reduce or eliminate inter-sample variability.

81. The method of embodiment 80, wherein the interfering molecule comprises a protein, DNA, and RNA.

82. The method of embodiment 80 or 81, wherein the small molecule comprises a colorless compound that tightly interacts with the interfering molecule.

83. The method of embodiments 80-82, further comprising providing the plurality of reference points.

84. The method of embodiments 80-83, wherein the step of determining the desired reaction time further comprises:

adding certain concentrations of the analyte to a plurality of reaction points, each of the plurality of reaction points containing the same amount of the regulator of the reporter and the aqueous solution;

analyzing color and/or absorbance of the plurality of reaction points over time;

plotting the color and/or absorbance of the plurality of reaction points over time versus the concentrations of the analyte; and determining which time point yields a color and/or absorbance output spanning a desired range of absorbances across the analyte concentration range.

85. The method of embodiments 80-84, wherein the step of determining the saturating amount of the analyte further comprises:

adding certain amounts of the analyte to a plurality of reaction points containing the same amount of the regulator of the reporter and the aqueous solution;

analyzing color and/or absorbance of the plurality of reaction points over a time course;

plotting the color and/or absorbance of the plurality of reaction points versus the reaction time; and determining which amounts of the analyte yield substantially similar color and/or absorbance output throughout the time course.

86. The method of embodiments 80-85, wherein determining the varying amounts of the regulator of the reporter further comprises:

adding certain amounts of the analyte to a plurality of reaction points containing a certain amount of the analyte and the aqueous solution;

analyzing color and/or absorbance of the plurality of reaction points over a time course;

plotting the color and/or absorbance of the plurality of reaction points versus the reaction time; and determining which amounts of the regulator of the reporter yield color and/or absorbance outputs throughout the time course that are substantially similar to the color and/or absorbance outputs throughout a time course of different amounts of analyte.

87. The method of embodiment 86, further comprising calculating the best-fit reaction for each amount of the regulator of the reporter to include in the series of the standard reference reactions, the calculating step comprising:

calculating the sum of squared error (SSE) minimization between each standard and test reaction at a series of time points spanning the determined reaction time, wherein the standard reaction that has the lowest SSE is determined to be the best-fit reaction for that amount of the regulator of the reporter.

88. The method of embodiments 80-87, wherein the aqueous solution is water.

89. The method of embodiment 88, wherein the water is taken from a lake, an ocean, a river, a source of potable water, wastewater, rainwater runoff, or an industrial discharge, effluent, or waste stream.

90. The method of embodiments 80-89, wherein the reporter is plasmid-based or is present on a linear fragment of DNA.

91. The method of embodiment 90, wherein the plasmid-based reporter comprises the regulator and a reporter gene operatively linked to a genetic element that is regulated by the regulator.

92. The method of embodiment 90, wherein the linear fragment of DNA comprises the regulator and a reporter gene operatively linked to a genetic element that is regulated by the regulator.

93. The method of embodiment 90, wherein the regulator comprises a transcription factor, a repressor, and an activator.

94. The method of embodiment 91 or 92, wherein the genetic element comprises a promoter, one or more regulatory protein binding sites, one or more repressor binding sites, and one or more transcription factor binding sites.

95. The method of embodiment 91 or 92, wherein the reporter gene produces a colorimetric gene product.

96. The method of embodiment 95, wherein the colorimetric gene product comprises a fluorescent protein, a luminescent protein, a colored protein, a protein that produces a detectable and quantifiable product, and a protein that can be quantified by measuring its absorbance at a wavelength.

97. A diagnostic tool for measuring an unknown amount of an analyte in an aqueous solution, the tool comprising:
 a first reference point having a first distinct color corresponding to a first amount of the analyte;
 a second reference point having a second distinct color corresponding to a second amount of the analyte; and
 a third reference point having a third distinct color corresponding to a third amount of the analyte,
 wherein the first distinct color is substantially similar to a colorimetric gene product generated when an aqueous solution with the first amount of the analyte is combined with a predetermined amount of a regulator of a reporter and a predetermined saturation amount of the analyte for a predetermined reaction time,
 wherein the second distinct color is substantially similar to a colorimetric gene product generated when an aqueous solution with the second amount of the analyte is combined with the predetermined amount of the regulator of a reporter and the predetermined saturation amount of the analyte for the predetermined reaction time,
 wherein the third distinct color is substantially similar to a colorimetric gene product generated when an aqueous solution with the third amount of the analyte is combined with the predetermined amount of the regulator of a reporter and the predetermined saturation amount of the analyte for the predetermined reaction time, and
 wherein the tool is configured to reduce or eliminate inter-sample variability.

98. The diagnostic tool of embodiment 97, further comprising providing the plurality of reference points.

99. The diagnostic tool of embodiment 97 or 98, wherein determining the predetermined reaction time further comprises:
 adding certain concentrations of the analyte to a plurality of reaction points, each of the plurality of reaction points containing the same amount of the regulator of the reporter and the aqueous solution;
 analyzing color and/or absorbance of the plurality of reaction points over time;
 plotting the color and/or absorbance of the plurality of reaction points over time versus the concentrations of the analyte; and
 determining which time point yields a color and/or absorbance output spanning a desired range of absorbances across the analyte concentration range.

100. The diagnostic tool of embodiments 97-99, wherein determining the predetermined saturating amount of the analyte further comprises:
 adding certain amounts of the analyte to a plurality of reaction points containing the same amount of the regulator of the reporter and the aqueous solution;
 analyzing color and/or absorbance of the plurality of reaction points over a time course;
 plotting the color and/or absorbance of the plurality of reaction points versus the reaction time; and
 determining which amounts of the analyte yield substantially similar color and/or absorbance output throughout the time course.

101. The diagnostic tool of embodiments 97-100, wherein determining the predetermined amount of the regulator of the reporter further comprises:
 adding certain amounts of the regulator to a plurality of reaction points containing a certain amount of the analyte and the aqueous solution;
 analyzing color and/or absorbance of the plurality of reaction points over a time course;
 plotting the color and/or absorbance of the plurality of reaction points versus the reaction time; and
 determining which amounts of the regulator of the reporter yield color and/or absorbance outputs throughout the time course that are substantially similar to the color and/or absorbance outputs throughout a time course of different amounts of analyte.

102. The diagnostic tool of embodiment 101, further comprising calculating the best-fit reaction for each amount of the regulator of the reporter to include in the series of the standard reference reactions, the calculating step comprising:
 calculating the sum of squared error (SSE) minimization between each standard and test reaction at a series of time points spanning the determined reaction time, wherein the standard reaction that has the lowest SSE is determined to be the best-fit reaction for that amount of the regulator of the reporter.

103. The diagnostic tool of embodiments 97-102, wherein the aqueous solution is water.

104. The diagnostic tool of embodiment 103, wherein the water is taken from a lake, an ocean, a river, a source of potable water, wastewater, rainwater runoff, or an industrial discharge, effluent, or waste stream.

105. The diagnostic tool of embodiments 97-104, wherein the reporter is plasmid-based or is present on a linear fragment of DNA.

106. The diagnostic tool of embodiment 105, wherein the plasmid-based reporter comprises the regulator and a reporter gene operatively linked to a genetic element that is regulated by the regulator.

107. The diagnostic tool of embodiment 105, wherein the linear fragment of DNA comprises the regulator and a reporter gene operatively linked to a genetic element that is regulated by the regulator.

108. The diagnostic tool of embodiment 105, wherein the regulator comprises a transcription factor, a repressor, and an activator.

109. The diagnostic tool of embodiment 106 or 107, wherein the genetic element comprises a promoter, one or more regulatory protein binding sites, one or more repressor binding sites, and one or more transcription factor binding sites.

110. The diagnostic tool of embodiment 106 or 107, wherein the reporter gene produces a colorimetric gene product.

111. The diagnostic tool of embodiment 110, wherein the colorimetric gene product comprises a fluorescent protein, a luminescent protein, a colored protein, a protein that produces a detectable and quantifiable product, and a protein that can be quantified by measuring its absorbance at a wavelength.

112. The diagnostic tool of embodiments 97-111, further comprising addition of a small molecule, wherein the small molecule displaces an interfering molecule from one or more of the regulator, the reporter, and a molecule acted on by the reporter.

113. A method of measuring an unknown amount of an analyte in an aqueous solution, the method comprising:

provrding a diagnostic tool, the tool comprising a plurality of reference points, each reference point in the plurality of reference points being a distinct color and corresponding to a predetermined different amount of the analyte;

combining the aqueous solution, a predetermined saturating amount of the analyte, and a predetermined amount of a regulator of a reporter;

reacting the regulator of the reporter with the analyte for a predetermined reaction time to generate a colorimetric gene product;

determining a first reference point in the plurality of reference points having a color corresponding to the generated colorimetric gene product, wherein the predetermined different amount of the analyte corresponding to the first reference point is equal to the unknown amount of the analyte in the aqueous solution, and wherein the method is configured to reduce or eliminate inter-sample variability.

114. The method of embodiment 113, further comprising providing the plurality of reference points.

115. The method of embodiment 113 or 114, wherein determining the predetermined reaction time further comprises:

adding certain concentrations of the analyte to a plurality of reaction points, each of the plurality of reaction points containing the same amount of the regulator of the reporter and the aqueous solution;

analyzing color and/or absorbance of the plurality of reaction points over time;

plotting the color and/or absorbance of the plurality of reaction points over time versus the concentrations of the analyte; and determining which time point yields a color and/or absorbance output spanning a desired range of absorbances across the analyte concentration range.

116. The method of embodiments 113-115, wherein determining the predetermined saturating amount of the analyte further comprises:

adding certain amounts of the analyte to a plurality of reaction points containing the same amount of the regulator of the reporter and the aqueous solution;

analyzing color and/or absorbance of the plurality of reaction points over a time course;

plotting the color and/or absorbance of the plurality of reaction points versus the reaction time; and determining which amounts of the analyte yield substantially similar color and/or absorbance output throughout the time course.

117. The method of embodiments 113-116, wherein determining the predetermined amount of the regulator of the reporter further comprises:

adding certain amounts of the regulator to a plurality of reaction points containing a certain amount of the analyte and the aqueous solution;

analyzing color and/or absorbance of the plurality of reaction points over a time course;

plotting the color and/or absorbance of the plurality of reaction points versus the reaction time; and determining which amounts of the regulator of the reporter yield color and/or absorbance outputs throughout the time course that are substantially similar to the color and/or absorbance outputs throughout a time course of different amounts of analyte.

118. The method of embodiment 117, further comprising calculating the best-fit reaction for each amount of the regulator of the reporter to include in the series of the standard reference reactions, the calculating step comprising:

calculating the sum of squared error (SSE) minimization between each standard and test reaction at a series of time points spanning the determined reaction time, wherein the standard reaction that has the lowest SSE is determined to be the best-fit reaction for that amount of the regulator of the reporter.

119. The method of embodiments 113-118, wherein the aqueous solution is water.

120. The method of embodiment 119, wherein the water is taken from a lake, an ocean, a river, a source of potable water, wastewater, rainwater runoff, or an industrial discharge, effluent, or waste stream.

121. The method of embodiments 113-120, wherein the reporter is plasmid-based or is present on a linear fragment of DNA.

122. The method of embodiment 121, wherein the plasmid-based reporter comprises the regulator and a reporter gene operatively linked to a genetic element that is regulated by the regulator.

123. The method of embodiment 121, wherein the linear fragment of DNA comprises the regulator and a reporter gene operatively linked to a genetic element that is regulated by the regulator.

124. The method of embodiment 121, wherein the regulator comprises a transcription factor, a repressor, and an activator.

125. The method of embodiment 122 or 123, wherein the genetic element comprises a promoter, one or more regulatory protein binding sites, one or more repressor binding sites, and one or more transcription factor binding sites.

126. The method of embodiment 122 or 123, wherein the reporter gene produces a colorimetric gene product.

127. The method of embodiment 126, wherein the colorimetric gene product comprises a fluorescent protein, a luminescent protein, a colored protein, a protein that produces a detectable and quantifiable product, and a protein that can be quantified by measuring its absorbance at a wavelength.

128. The method of embodiments 113-127, further comprising addition of a small molecule, wherein the small molecule displaces an interfering molecule from one or more of the regulator, the reporter, and a molecule acted on by the reporter.

While several possible embodiments are disclosed above, embodiments of the present invention are not so limited. These exemplary embodiments are not intended to be exhaustive or to unnecessarily limit the scope of the invention, but instead were chosen and described in order to explain the principles of the present invention so that others skilled in the art may practice the invention. Indeed, various modifications of the invention in addition to those described herein will become apparent to those skilled in the art from the foregoing description. Such modifications are intended to fall within the scope of the appended claims. Further, the terminology employed herein is used for the purpose of describing exemplary embodiments only and the terminology is not intended to be limiting since the scope of the various embodiments of the present invention will be limited only by the appended claims and equivalents thereof. The scope of the invention is therefore indicated by the following claims, rather than the foregoing description and above-discussed embodiments, and all changes that come within the meaning and range of equivalents thereof are intended to be embraced therein.

What is claimed is:

1. A method comprising:
   determining a desired amount of a regulator of a reporter;
   determining a saturating amount of an analyte; and
   determining a desired reaction time;
   wherein the desired amount of the regulator of the reporter, the saturating amount of the analyte, and the desired reaction time are determined such that when an unknown amount of the analyte is combined with a sample and the desired amount of the regulator of the reporter for the desired reaction time, a colorimetric gene product is generated having a color corresponding to a color of a first reference point in a plurality of reference points containing the sample, the saturating amount of the analyte, and the desired amount of the regulator of the reporter, the first reference point associated with an amount of the analyte at least substantially equal to the unknown amount of the analyte; and
   wherein the method is configured to reduce or eliminate inter-sample variability.

2. The method of claim 1, wherein:
   the sample is selected from the group consisting of:
   a biological sample and a cell-free extract (CFE); and
   an aqueous solution;
   and the method is a method of generating a diagnostic tool for measuring the unknown amount of the analyte in the sample, the diagnostic tool comprising the plurality of the reference points, each reference point being a distinct color and corresponding to a different amount of the analyte; or
   the sample is selected from the group consisting of:
   a serum sample; and
   an aqueous solution;
   and the method is a method for generating a range of visible colors in samples with unknown amounts of the analyte by addition of a small molecule, wherein the small molecule displaces an interfering molecule from one or more of the regulator, the reporter, and a molecule acted on by the reporter.

3. The method of claim 2, wherein determining the desired reaction time comprises:
   adding certain concentrations of the analyte to a plurality of reaction points, each of the plurality of reaction points containing the same amount of the regulator of the reporter and the sample;
   analyzing color and/or absorbance of the plurality of reaction points over time;
   plotting the color and/or absorbance of the plurality of reaction points over time versus the concentrations of the analyte; and
   determining which time point yields a color and/or absorbance output spanning a desired range of absorbances across the analyte concentration range.

4. The method of claim 2, wherein determining the saturating amount of the analyte comprises:
   adding certain amounts of the analyte to a plurality of reaction points containing the same amount of the regulator of the reporter and the sample;
   analyzing color and/or absorbance of the plurality of reaction points over a time course;
   plotting the color and/or absorbance of the plurality of reaction points versus the reaction time; and
   determining which amounts of the analyte yield substantially similar color and/or absorbance output throughout the time course.

5. The method of claim 2, wherein determining the desired amount of the regulator of the reporter comprises:
   adding certain amounts of the analyte to a plurality of reaction points containing a certain amount of the analyte and the sample;
   analyzing color and/or absorbance of the plurality of reaction points over a time course;
   plotting the color and/or absorbance of the plurality of reaction points versus the reaction time; and
   determining which amounts of the regulator of the reporter yield color and/or absorbance outputs throughout the time course that are substantially similar to the color and/or absorbance outputs throughout a time course of different amounts of analyte.

6. The method of claim 5 further comprising calculating a best-fit reaction for each amount of the regulator of the reporter to include in the series of the standard reference reactions, the calculating step comprising:
   calculating a sum of squared error (SSE) minimization between each standard and test reaction at a series of time points spanning the determined reaction time; and
   wherein the standard reaction that has the lowest SSE is determined to be the best-fit reaction for that amount of the regulator of the reporter.

7. The method of claim 1, wherein the sample is a biological fluid sample.

8. The method of claim 7, wherein the biological fluid sample is selected from the group consisting of blood, serum, plasma, urine, saliva, tears, mucus, lymph, interstitial fluid, cerebrospinal fluid, pus, breast milk, and amniotic fluid.

9. The method of claim 2, wherein the reporter is plasmid-based or is present on a linear fragment of DNA.

10. The method of claim 2, wherein the reporter is plasmid-based and comprises the regulator and a reporter gene operatively linked to a genetic element that is regulated by the regulator.

11. The method of claim 2, wherein the reporter is present on a linear fragment of DNA comprising the regulator and a reporter gene operatively linked to a genetic element that is regulated by the regulator.

12. The method of claim 9, wherein the regulator comprises a transcription factor, a repressor, and an activator.

13. The method of claim 10, wherein the genetic element comprises a promoter, one or more regulatory protein binding sites, one or more repressor binding sites, and one or more transcription factor binding sites.

14. The method of claim 10, wherein the reporter gene produces the colorimetric gene product.

15. The method of claim 14, wherein the colorimetric gene product is selected from the group consisting of a fluorescent protein, a luminescent protein, a colored protein, a protein that produces a detectable and quantifiable product, and a protein that can be quantified by measuring its absorbance at a wavelength.

16. The method of claim 1, wherein the analyte is zinc.

17. The method of claim 16, wherein the reporter comprises a first plasmid containing a transcriptional regulator ZntR and a second plasmid containing a reporter gene operatively linked to a ZntA promoter; and
   wherein expression from the ZntA promoter is controlled by the amount of the transcriptional regulator ZntR.

18. The method of claim 1, wherein the analyte is RNA.

19. The method of claim 18, wherein a plasmid-based reporter comprises a first plasmid containing a toehold switch activated by a trigger RNA sequence that is operatively linked to a reporter gene; and wherein expression of the reporter gene is controlled by the amount of the trigger RNA sequence.

20. The method of claim 2, wherein the interfering molecule is selected from the group consisting of a protein, DNA, and RNA.

21. The method of claim 2, wherein the small molecule comprises a colorless compound that tightly interacts with the interfering molecule.

22. The method of claim 2, wherein the aqueous solution is water.

23. The method of claim 22, wherein the water is taken from a lake, an ocean, a river, a source of potable water, wastewater, rainwater runoff, or an industrial discharge, effluent, or waste stream.

24. A method of measuring an unknown amount of an analyte in a biological sample comprising:
   combining the biological sample with the unknown amount of analyte with an amount of cell-free extract (CFE) and an amount of a regulator of a reporter for a reaction time; and
   measuring the unknown amount of the analyte in the biological sample by comparing a generated colorimetric gene product from the combining that has a color corresponding to a color of a first reference point;
   wherein the first reference point has a color corresponding to an amount of the analyte at least substantially equal to the unknown amount of analyte; and
   wherein the method is configured to reduce or eliminate inter-sample variability.

25. The method of claim 24 further comprising:
   determining the amount of the regulator of the reporter;
   determining a saturating amount of the analyte; and
   determining the reaction time;
   wherein the first reference point is one among a plurality of reference points, each reference point being a distinct color and corresponding to a different amount of the analyte; and
   wherein the determined amount of the regulator of the reporter, the determined saturating amount of the analyte, and the determined reaction time are calculated such that when the unknown amount of the analyte is combined with the biological sample, the CFE, and the determined amount of the regulator of the reporter for the determined reaction time, the colorimetric gene product is generated having the color corresponding to the color of the first reference point.

* * * * *